United States Patent
Adiri et al.

(10) Patent No.: US 11,250,944 B2
(45) Date of Patent: Feb. 15, 2022

(54) UNIQUELY CODED COLOR BOARDS FOR ANALYZING IMAGES

(71) Applicant: HEALTHY.IO LTD., Tel Aviv (IL)

(72) Inventors: Yonatan Adiri, Tel Aviv (IL); Ron Zohar, Tel Aviv (IL); Ido Omer, Barcelona (ES)

(73) Assignee: HEALTHY.IO LTD., Tel Aviv (IL)

( * ) Notice: Subject to any disclaimer, the term of this patent is extended or adjusted under 35 U.S.C. 154(b) by 138 days.

(21) Appl. No.: 16/727,293

(22) Filed: Dec. 26, 2019

(65) Prior Publication Data

US 2020/0211228 A1 Jul. 2, 2020

Related U.S. Application Data

(60) Provisional application No. 62/787,402, filed on Jan. 2, 2019, provisional application No. 62/812,354, filed
(Continued)

(51) Int. Cl.
*G06K 9/00* (2006.01)
*G16H 30/40* (2018.01)
(Continued)

(52) U.S. Cl.
CPC ........... *G16H 30/40* (2018.01); *A61B 5/1034* (2013.01); *A61B 5/445* (2013.01); *G01N 1/12* (2013.01);
(Continued)

(58) Field of Classification Search
None
See application file for complete search history.

(56) References Cited

U.S. PATENT DOCUMENTS

| 5,408,535 A | 4/1995 | Howard, III et al. |
| 6,285,454 B1 | 9/2001 | Douglas et al. |
| (Continued) | | |

FOREIGN PATENT DOCUMENTS

| DE | 102010011838 A1 | 9/2011 |
| EP | 2646809 | 8/2018 |
| (Continued) | | |

OTHER PUBLICATIONS

U.S. Appl. No. 14/283,208.
(Continued)

*Primary Examiner* — Wei Wen Yang
(74) *Attorney, Agent, or Firm* — Finnegan, Henderson, Farabow, Garrett & Dunner, LLP

(57) ABSTRACT

Systems and methods for a color board for use in reagent strip testing are disclosed. One implementation may include a color board surface, a first colored reference element printed on the color board surface, and a second colored reference element printed on the color board surface. The color board may also include a test region on the color board surface configured to receive at least one reagent pad. The color board may also include a unique code, and the code may reflect specific chromatic properties associated with each of the first colored reference element and the second color reference element at a time of printing. The unique code may be machine readable to enable a machine to later normalize a comparison color, for determining chromatic properties of the at least one reagent pad.

25 Claims, 31 Drawing Sheets
(5 of 31 Drawing Sheet(s) Filed in Color)

Related U.S. Application Data on Mar. 1, 2019, provisional application No. 62/812,365, filed on Mar. 1, 2019, provisional application No. 62/812,373, filed on Mar. 1, 2019, provisional application No. 62/814,922, filed on Mar. 7, 2019, provisional application No. 62/814,925, filed on Mar. 7, 2019.

(51) Int. Cl.

| | | |
|---|---|---|
| G16H 40/20 | (2018.01) | |
| G16H 10/60 | (2018.01) | |
| G01N 33/70 | (2006.01) | |
| G01N 33/483 | (2006.01) | |
| G06Q 40/08 | (2012.01) | |
| G06T 7/00 | (2017.01) | |
| G01N 1/12 | (2006.01) | |
| G01N 21/78 | (2006.01) | |
| G01N 33/487 | (2006.01) | |
| G01N 33/493 | (2006.01) | |
| G01N 33/52 | (2006.01) | |
| G01N 33/68 | (2006.01) | |
| G16H 10/40 | (2018.01) | |
| G16H 30/20 | (2018.01) | |
| G01N 33/50 | (2006.01) | |
| H04L 29/06 | (2006.01) | |
| H04W 4/12 | (2009.01) | |
| H04W 12/06 | (2021.01) | |
| G06T 7/90 | (2017.01) | |
| G16H 70/00 | (2018.01) | |
| G06F 16/583 | (2019.01) | |
| A61B 5/103 | (2006.01) | |
| A61B 5/00 | (2006.01) | |
| G06Q 20/38 | (2012.01) | |
| G06T 7/73 | (2017.01) | |
| G06T 7/11 | (2017.01) | |
| G16H 15/00 | (2018.01) | |
| G01N 1/28 | (2006.01) | |

(52) U.S. Cl.
CPC ......... *G01N 21/78* (2013.01); *G01N 33/4833* (2013.01); *G01N 33/48778* (2013.01); *G01N 33/493* (2013.01); *G01N 33/5094* (2013.01); *G01N 33/52* (2013.01); *G01N 33/6803* (2013.01); *G01N 33/6827* (2013.01); *G01N 33/70* (2013.01); *G06F 16/5838* (2019.01); *G06Q 20/385* (2013.01); *G06Q 40/08* (2013.01); *G06T 7/0012* (2013.01); *G06T 7/0014* (2013.01); *G06T 7/0016* (2013.01); *G06T 7/11* (2017.01); *G06T 7/74* (2017.01); *G06T 7/90* (2017.01); *G16H 10/40* (2018.01); *G16H 10/60* (2018.01); *G16H 30/20* (2018.01); *G16H 40/20* (2018.01); *G16H 70/00* (2018.01); *H04L 63/126* (2013.01); *H04W 4/12* (2013.01); *H04W 12/06* (2013.01); *G01N 2001/2826* (2013.01); *G06T 2207/10024* (2013.01); *G06T 2207/20112* (2013.01); *G06T 2207/30004* (2013.01); *G16H 15/00* (2018.01)

(56) References Cited

U.S. PATENT DOCUMENTS

| | | |
|---|---|---|
| D720,864 S | 1/2015 | Behar et al. |
| D735,879 S | 8/2015 | Behar et al. |
| 9,285,323 B2 | 3/2016 | Burg et al. |
| 9,311,520 B2 | 4/2016 | Burg et al. |
| D758,608 S | 6/2016 | Behar et al. |
| 9,528,941 B2 | 12/2016 | Burg et al. |
| 9,607,380 B2 | 3/2017 | Burg et al. |
| D783,838 S | 4/2017 | Zhao et al. |
| 9,690,904 B1 | 6/2017 | Zizi |
| 9,808,206 B1 | 11/2017 | Zhao et al. |
| 9,818,193 B2 | 11/2017 | Smart |
| 9,863,811 B2 | 1/2018 | Burg |
| 9,903,857 B2 | 2/2018 | Polwart et al. |
| D831,197 S | 10/2018 | Scruggs et al. |
| 10,143,425 B1 | 12/2018 | Zhao et al. |
| 10,267,743 B2 | 4/2019 | Burg et al. |
| 2005/0157304 A1 | 7/2005 | Xiao et al. |
| 2006/0292040 A1 | 12/2006 | Wickstead et al. |
| 2012/0106811 A1 | 5/2012 | Chen et al. |
| 2012/0178101 A1 | 7/2012 | Bae et al. |
| 2012/0282154 A1 | 11/2012 | Slowey et al. |
| 2014/0242612 A1 | 8/2014 | Wang et al. |
| 2014/0257058 A1 | 9/2014 | Clarysse et al. |
| 2015/0044098 A1 | 2/2015 | Smart et al. |
| 2015/0313484 A1 | 11/2015 | Burg et al. |
| 2017/0098137 A1* | 4/2017 | Burg .................. G01N 21/78 |
| 2017/0258340 A1 | 9/2017 | Przybyszewski et al. |
| 2018/0136140 A1* | 5/2018 | Brendsel ........... G01N 21/8483 |
| 2018/0252585 A1 | 9/2018 | Burg |
| 2019/0073763 A1* | 3/2019 | Li .................... G01N 33/48792 |
| 2019/0298183 A1 | 10/2019 | Burg et al. |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0350535 A1 | 11/2019 | Zhao et al. |
| 2020/0196962 A1 | 6/2020 | Zhao et al. |
| 2020/0225166 A1 | 7/2020 | Burg et al. |
| 2020/0286600 A1 | 9/2020 | DeBrouwer et al. |

FOREIGN PATENT DOCUMENTS

| | | |
|---|---|---|
| EP | 3470825 | 4/2019 |
| KR | 1020100008840 A | 1/2010 |
| KR | 1020110024747 A | 3/2011 |
| WO | WO 2007/079843 A2 | 7/2007 |
| WO | WO 2013066642 | 5/2013 |
| WO | WO 2013116253 | 8/2013 |
| WO | WO 2013116316 | 8/2013 |
| WO | WO 2014025415 | 2/2014 |
| WO | WO 2015134820 | 9/2015 |
| WO | WO 2015171667 | 11/2015 |
| WO | WO 2016025935 | 2/2016 |
| WO | WO 2017127778 | 7/2017 |
| WO | WO 2017156501 | 9/2017 |

OTHER PUBLICATIONS

U.S. Appl. No. 14/283,210.
U.S. Appl. No. 14/283,211.
U.S. Appl. No. 14/283,213.
U.S. Appl. No. 14/641,303.
U.S. Appl. No. 16/215,623.
U.S. Appl. No. 15/812,452.
U.S. Appl. No. 15/390,714.
U.S. Appl. No. 14/675,719.
U.S. Appl. No. 29/491,524.

* cited by examiner

UNIQUELY CODED COLOR BOARDS FOR ANALYZING IMAGES

CROSS REFERENCES TO RELATED APPLICATIONS

This application claims the benefit of priority of U.S. Provisional Patent Application No. 62/787,402, filed on Jan. 2, 2019, U.S. Provisional Patent Application No. 62/812,354, filed on Mar. 1, 2019, U.S. Provisional Patent Application No. 62/812,365, filed on Mar. 1, 2019, U.S. Provisional Patent Application No. 62/812,373, filed on filed on Mar. 1, 2019, U.S. Provisional Patent Application No. 62/814,922, filed on Mar. 7, 2019, and U.S. Provisional Patent Application No. 62/814,925, filed on Mar. 7, 2019, all of which are incorporated herein by reference in their entirety.

BACKGROUND

I. Technical Field

The present disclosure relates generally to the field of image processing for medical purposes. More specifically, the present disclosure relates to systems, methods, and devices for using image analysis for evaluating medical conditions.

II. Background Information

Computer vision may be used in medical testing to determine quantitative and qualitative clinical data. Traditionally, regulatory-approved clinical devices use dedicated hardware such as pre-calibrated scanners that operate in well-known and monitored capturing and illumination conditions, together with classifiers that operate based on the calibrated images derived by the scanners.

In recent years, smartphones have become personal mobile computers with high processing power, wireless Internet access, and high-resolution camera capabilities. However, turning a smartphone into a regulatory-approved clinical device is challenging for at least three main reasons. First, there may be a lack of quality uniformity of the smartphones' cameras. This can occur, for a number of reasons, including the fact that the settings and imaging of each brand and model of smartphone may differ from one to the next. Even within a particular model, there may be slight variations in acquired images. Second, when using smartphones across a host of non-uniformly lit environments, local illumination conditions can lead to varying results. Third, non-medical professionals who operate smartphones may have difficulty following strict operation procedures.

The disclosed embodiments are directed to providing new and improved ways for using personal communications devices for medical testing.

SUMMARY

Embodiments consistent with the present disclosure provide systems, methods, and devices for capturing and analyzing images for evaluating medical conditions. In one example, consistent with the disclosed embodiments, an exemplary system may receive an image depicting a tissue feature with multiple segments of differing colors and may use the image to determine the state of the tissue feature. In a second example, consistent with the disclosed embodiments, an exemplary system may receive an image depicting a dipstick having one or more reagent pads and may determine an extent of a chemical reaction on the one or more reagent pads.

Consistent with disclosed embodiments, systems and methods for a color board for use in reagent strip testing are disclosed. For example, consistent with one embodiment a disclosed system may include a color board surface, a first colored reference element printed on the color board surface, and a second colored reference element printed on the color board surface. The color board may also include a test region on the color board surface configured to receive at least one reagent pad. The color board may also include a unique code, and the code may reflect specific chromatic properties associated with each of the first colored reference element and the second color reference element at a time of printing. The unique code may be machine readable to enable a machine to later normalize a comparison color, for determining chromatic properties of the at least one reagent pad.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. The patent or application file contains at least one drawing executed in color. Copies of this patent or patent application publication with color drawings will be provided by the Office upon request and payment of the necessary fee. In the drawings.

DETAILED DESCRIPTION

Figure 1A:
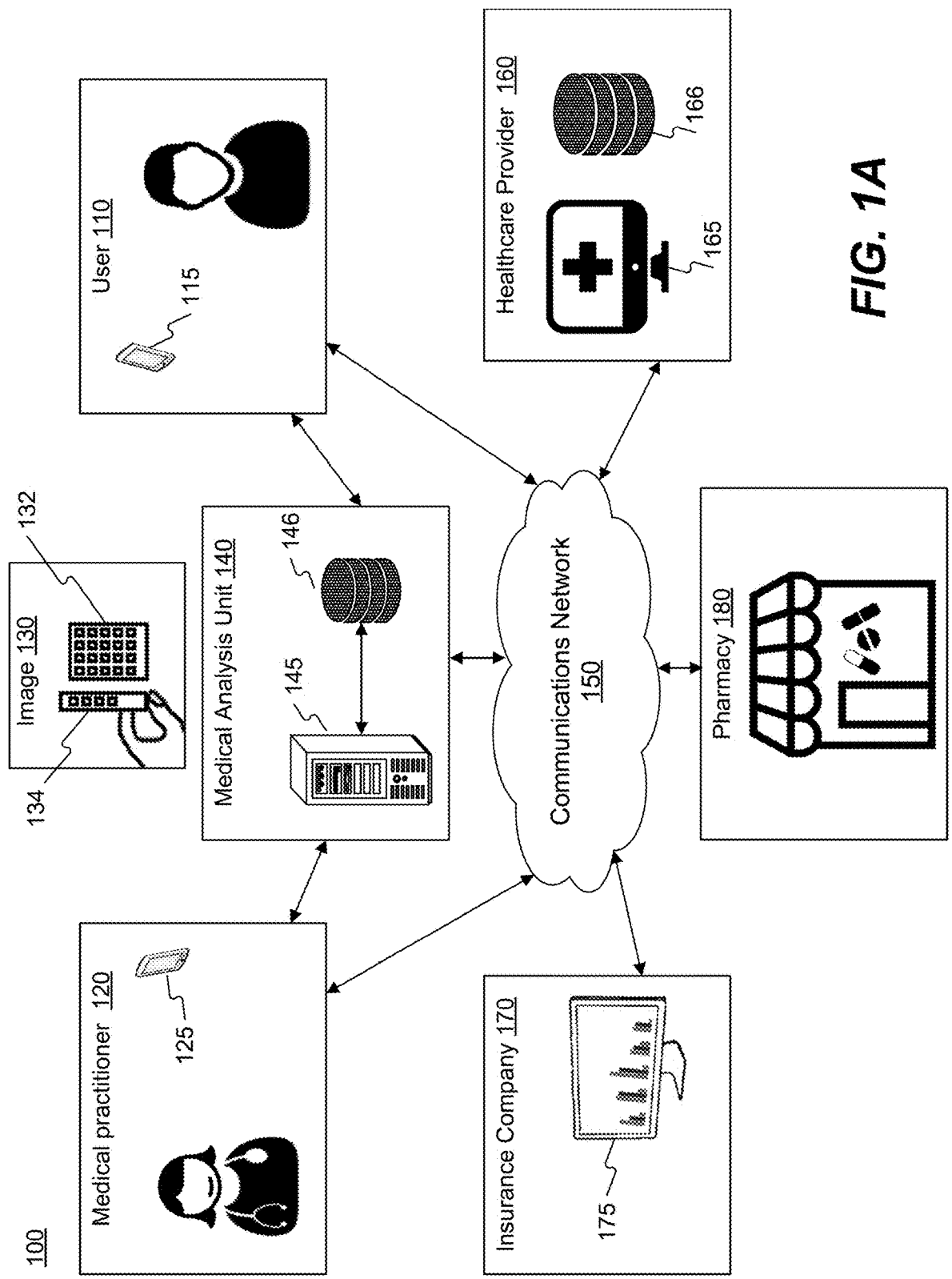
FIG. 1A is a schematic illustration of an exemplary system that uses image data captured by mobile communications devices for medical testing, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples, but is inclusive of general principles described herein in addition to the general principles encompassed by the appended claims.

The present disclosure is directed to systems and methods for processing images captured by an image sensor. As used herein, the term "image sensor" refers to any device capable of detecting and converting optical signals in the near-infrared, infrared, visible, and ultraviolet spectrums into electrical signals. Examples of image sensors may include digital cameras, phone cameras, semiconductor charge-coupled devices (CCD), active pixel sensors in complementary metal-oxide-semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct a 3D image. The image data acquired by the image sensor may be transmitted by wired or wireless transmission to a remote server.

Consistent with the present disclosure, the image sensor may be part of a camera included in a mobile communications device. The term "mobile communications device" refers to any portable device with image capturing capabilities that can communicate with a remote server over a wireless network. Examples of mobile communications devices include, smartphones, tablets, smartwatches, smart glasses, wearable sensors and other wearable devices, wireless communication chipsets, user equipment (UE), personal digital assistants, laptop computers, and any other portable pieces of communications equipment. It is noted that the terms "handheld mobile communications device," "handheld mobile device," "mobile communications device," and "mobile device" may be used interchangeably herein and may refer to any of the variety of devices listed above.

Embodiments of the present disclosure further include analyzing images to identify a colorized surface in proximity to a medical analysis region. As used herein, the term "colorized surface" may broadly refer to any surface having planar or nonplanar properties. The colorized surface may cover or encapsulate at least a portion of a 2D object (such as a sheet of paper) or at least a portion of a 3D object (such as a box or a body part). The colorized surface may include a plurality of reference elements for enabling light and color calibration. In some embodiments, the colorized surface may be printed on a sticker or a plaster (e.g., adhesive bandage), for example, the colorized surface illustrated in FIG. 4A. In other embodiments, the colorized surface may be printed or otherwise presented on a board, cardstock, plastic or any other medium adapted to serve as a reference. The colorized surface may be incorporated into the packaging of a test kit, for example. One non-limiting example of a colorized surface is illustrated in FIG. 4B. The image correction enabled by the colorized surface may be used to enable a color correction of an image of an object depicted in the medical analysis region. As used herein, the term "medical analysis region" may be an area on or near the surface distinct from the colorized portion of the surface used for color correction where an object for examination may be placed. The medical analysis region may be of uniform color or varied color so long as other portions of the colorized surface may be used as references for color correction. In a preferred embodiment, the colorized surface may include an un-colorized or uniformly colorized region demarcated for object placement. Such a distinct region may be larger than the object to be received thereon. In other embodiments, the medical analysis region may not be demarcated, permitting the user to independently select a location of object placement, so long as enough of the colorized surface remains unblocked for reference purposes during image analysis.

In some embodiments, the examined object is a skin or other tissue or anatomical feature, and the medical analysis region may include any part of the patient's body depicted in the image. In another embodiment, the examined object may be a dipstick, and the color of the medical analysis region may be significantly darker or lighter than a majority of the colorized surface. For example, the medical analysis region maybe at least 50% darker than the colorized surface. It is noted that the terms "medical analysis region," "dipstick placement region," and "test region," may be used interchangeably herein to refer to the same area.

Consistent with the present disclosure, the colorized surface may enable processing of the image to determine the colors of the examined object, irrespective of local illumination conditions. The term "irrespective of local illumination conditions" refers to the output of an image analysis process in which the suggested system rectifies the colors of the examined object to remove at least some effects of local illumination. Effects of local illumination conditions to be removed, may include one or more of reflections, shades, light temperature (e.g., soft white, cool white, daylight), and any other condition that may impact the detection of object color. Additionally, the colorized surface may also enable processing of the image to determine the colors of the examined object, irrespective of specific image capturing effects associated with the image capturing device. Examples of the different effects associated with the image capturing process that may be removed are described below.

In some embodiments, an image correction factor may be generated based on the determined local illumination conditions and/or image capturing parameters. The image correction factor may be used to remove one or more local illumination variations and to determine illumination invariant colors of the examined object. The image correction factor may be used to remove image capturing process effects to determine capturing process invariant colors of the examined object. In one example, the invariant colors may be used to determine an extent of a chemical reaction on a reagent pad. In another example, the illumination invariant colors may be used to determine a skin condition, such as a condition of a wound. In yet another example, the invariant colors may be used to determine a condition of a tissue, such as skin, oral mucosa, nasal mocosa, and so forth. In an additional example, the invariant colors may be used to determine properties of biological material, such as a stool sample, a urine sample, a phlegm sample, a blood sample, a wax sample, and so forth.

The term "confidence level" refers to any indication, numeric or otherwise, of a level (e.g., within a predetermined range) indicative of an amount of confidence the system has that the determined colors of the examined object are the colors of the examined object irrespective of local illumination conditions and/or image capturing settings effects. For example, the confidence level may have a value between 1 and 10. Alternatively, the confidence level may be expressed as a percentage or any other numerical or non-numerical indication. In some cases, the system may compare the confidence level to a threshold. The term "threshold" as used herein denotes a reference value, a level, a point, or a range of values. In operation, when a confidence level of a measurement exceeds a threshold (or below it depending on a particular use case), the system may follow a first course of action and, when the confidence level is below it (or above it depending on a particular use case), the system may follow a second course of action. The value of the threshold may be predetermined for each type of examined object or may be dynamically selected based on different considerations.

Reference is now made to FIG. 1A, which shows an example of a system 100 that uses image analysis to complete a medical examination. System 100 may be computer-based and may include computer system components, desktop computers, workstations, tablets, handheld computing devices, memory devices, and/or internal network(s) connecting the components. System 100 may include or be connected to various network computing resources (e.g., servers, routers, switches, network connections, storage devices, etc.) for supporting services provided by system 100.

Consistent with the present disclosure, system 100 may enable user 110 to complete a medical examination. In addition, system 100 may enable a medical practitioner 120 to participate in the medical examination using a mobile communications device 125. The disclosure below that describes the functionalities of mobile communications device 115 similarly describes the functionalities of mobile communications device 125. In one embodiment, medical practitioner 120 may be a nurse that captures images of an object associated with user 110. In another embodiment, medical practitioner 120 may be a physician of user 110 who receives the test results of the medical examination. In the example illustrated in FIG. 1A, user 110 may use mobile communications device 115 to capture an image 130 that includes a colorized surface 132 and an object to be examined 134. Image data associated with image 130 may be transmitted to a medical analysis unit 140 for medical testing (directly or via a communication network). Medical analysis unit 140 may include a server 145 coupled to one or more physical or virtual storage devices such as a data structure 146. System 100 may also include or be connected to a communications network 150 that facilitates communications and data exchange between different system components and the different entities associated with system 100, such as, healthcare provider 160, insurance company 170, and pharmacy 180.

According to embodiments of the present disclosure, medical analysis unit 140 may exchange data with a variety of communication devices associated with the different entities associated with system 100. The term "communication device" is intended to include all possible types of devices capable of exchanging data using communications network 150. In some examples, the communication device may include a smartphone, a tablet, a mobile station, a personal digital assistant, a desktop, a laptop, an IoT device, a dedicated terminal, a server, a cloud, and any other device that enables data communications. In one implementation, medical analysis unit 140 may receive image data from mobile communications device 115, and cause mobile communications device 115 to provide user 110 with data derived from analysis of examined object 134. In another implementation, medical analysis unit 140 may transmit data to a communications device 165 of healthcare provider 160 for updating an electronic medical record (EMR) of user 110 stored in data structure 166. In another implementation, medical analysis unit 140 may receive information from a communications device 175 of insurance company 170. The received information may identify a group of individuals associated with a first insurance status. Thereafter, medical analysis unit 140 may initiate medical examinations to determine if there is a likelihood that the group of individuals is entitled to a second insurance status different from the first insurance status. In yet another implementation, medical analysis unit 140 may transmit a medicine prescription to pharmacy 180 for treating user 110 based on the test result derived from image data captured by mobile communications device 115.

Embodiments of the present disclosure may include, access, or otherwise utilize one or more data structures, such as a database. As uses herein the term "data structure" may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML data structure, an RDBMS data structure, an SQL data structure or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, SharePoint, Sybase, Oracle and Neo4J. Data structures, where suitable, may also include document management systems. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Consistent with the present disclosure, server 145 may access data structure 146 to determine, for example, specific chromatic properties associated with colorized surface 132 at the time of printing of the colorized surface 132. Data structures 146 and data structure 166 may utilize a volatile or non-volatile, magnetic, semiconductor, tape, optical, removable, non-removable, other type of storage device or tangible or non-transitory computer-readable medium, or any medium or mechanism for storing information. Data structure 146 (and data structure 166 mutatis mutandis) may be part of server 145 or separate from server 145 as shown. When data structure 146 is not part of server 145, server 145 may exchange data with data structure 146 via a communication link. Data structure 146 may include one or more memory devices that store data and instructions used to perform one or more features of the disclosed embodiments. In one embodiment, data structure 146 may include any a plurality of suitable data structures, ranging from small data structures hosted on a workstation to large data structures distributed among data centers. Data structure 146 may also include any combination of one or more data structures controlled by memory controller devices (e.g., server(s), etc.) or software.

Consistent with the present disclosure, communications network 150 may be any type of network (including infrastructure) that supports communications, exchanges information, and/or facilitates the exchange of information between the components of system 100. For example, communications network 150 may include or be part of the Internet, a Local Area Network, wireless network (e.g., a Wi-Fi/302.11 network), or other suitable connections. In other embodiments, one or more components of system 100 may communicate directly through dedicated communication links, such as, for example, a telephone network, an extranet, an intranet, the Internet, satellite communications, off-line communications, wireless communications, transponder communications, a local area network (LAN), a wide area network (WAN), a virtual private network (VPN), or any other mechanism or combinations of mechanism that enable data transmission.

The components and arrangements of system 100 shown in FIG. 1A are not intended to be exemplary only and are not intended to limit the disclosed embodiments, as the system components used to implement the disclosed processes and features may vary.

Figure 1B:
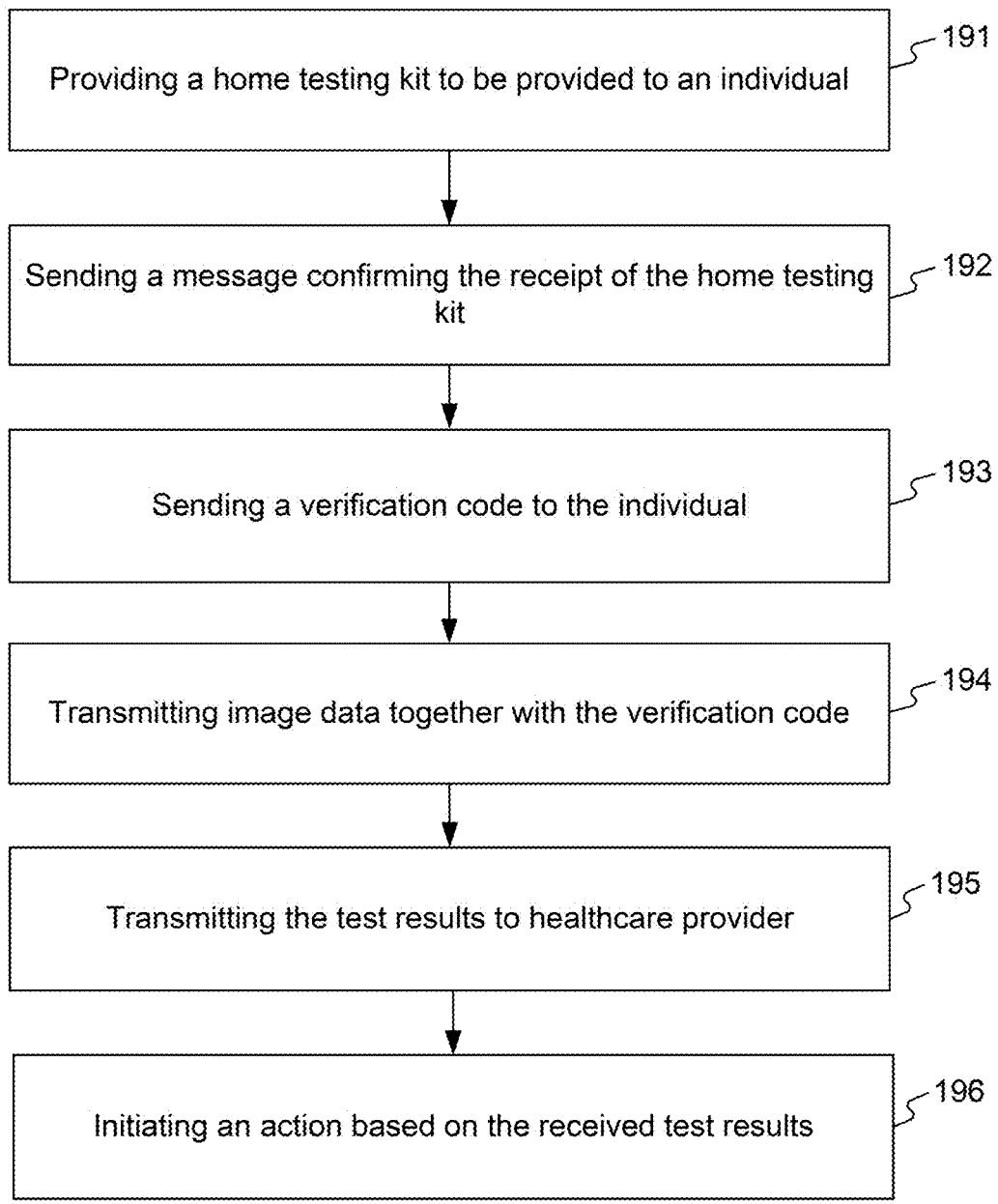
FIG. 1B is a flowchart of an exemplary process for completing a medical examination, consistent with the present disclosure.
Figure 1C:
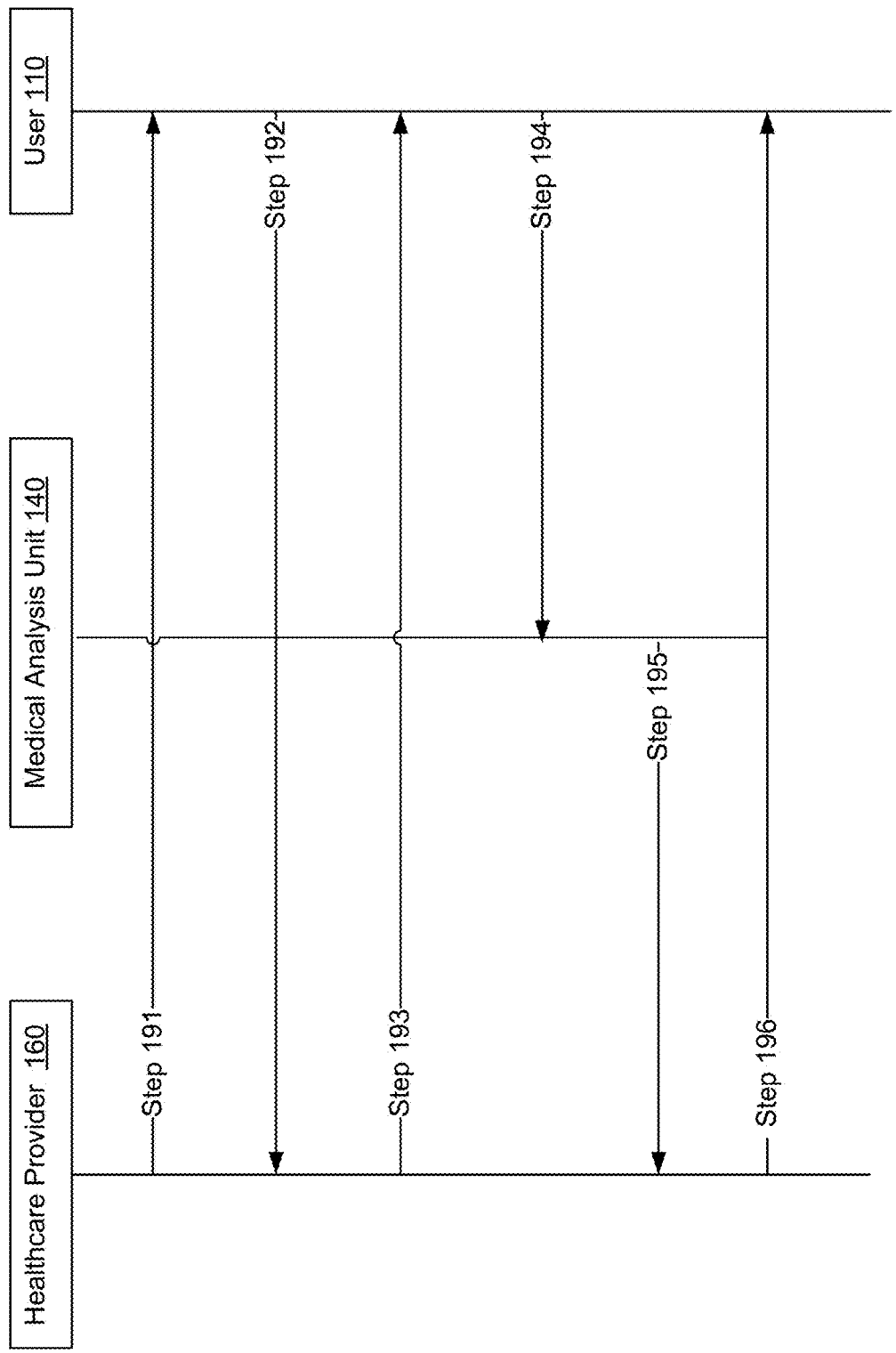
FIG. 1C is an exemplary flow diagram illustrating communications exchanges between different entities implementing the process of FIG. 1B.

FIG. 1B is a flowchart of an exemplary process for completing a medical examination according to embodiments of the present disclosure. In some embodiments, the exemplary process is executed by different components of system 100. For example, healthcare provider 160, medical analysis unit 140, and user 110. In one embodiment, any action performed by server 145 may be performed by any combination of mobile communications device 115, mobile communications device 125, communications device 165, and communications device 175. FIG. 1C illustrates how the exemplary process is implemented by healthcare provider 160, medical analysis unit 140, and user's mobile communications device 115.

Example process 190 starts when healthcare provider 160 causes a home testing kit to be physically provided to user 110 (step 191). Consistent with the present disclosure, causing the home testing kit to be physically provided to user 110 may include shipping the test kit to user 110, sending an instruction to a third party to ship a test kit to user 110, physically providing user 110 with a test kit, or conveying a test to user 110 in any other way. For example, shipping instructions may be generated, a pick up order may be placed with a shipping company, or the testing kit may be deposited for pickup by a courier. In some cases, healthcare provider 160 may cause home testing kits to be delivered to a group of individuals identified through information from insurance company 170. In other cases, healthcare provider 160 may cause home testing kits to be delivered to user 110 in response to a request from medical practitioner 120 or as the result of a request from user 110. Alternatively, healthcare provider 160 may automatically cause home testing kits to be delivered to user 110 based on information about user 110 stored in data structure 166. In one example, a physician may have previously prescribed annual testing for user 110, or user 110 might have met some triggering time-based criteria or health-based criteria that triggers an indication that user 110 should receive the test kit. In another example, an operator (such as a healthcare provider 160, insurance company 170, etc.) may conduct a query on data structure 166 to identify users that meet the selected criteria, and may cause delivery of home testing kits to at least some of the identified users.

Process 190 may continue when user 110 sends a message confirming the receipt of the home testing kit (step 192). In some embodiments, user 110 may send the message directly to healthcare provider 160. In other embodiments, user 110 may send the message using a dedicated application associated with medical analysis unit 140, and the message may be conveyed to healthcare provider 160. The message may be text or voice based, or may occur as a button pushed or box checked in response to a prompt on a user interface.

Alternatively, the message may simply be the scanning or entry of a code. Thereafter, healthcare provider 160 may send a verification code to user 110 (step 193). According to one embodiment, the verification code may be sent in a text message directly to user 110 after receiving the confirmation message, or may be provided through a user interface of an application accessed via a device of user 110. As an alternative to an exchange of electronic messages in order to obtaining the verification code, the verification code may be physically provided with the home testing kit in step 191. In such example, step 192 and step 193 may be excluded from process 190.

Process 190 may continue when user 110 follows instructions associated with the specific medical examination, uses mobile communications device 115 to capture image 130, and transmits image data together with (or in a manner that causes it to be associated with) the verification code to medical analysis unit 140 (step 194). The image data transmitted to image analysis unit 140 may include image 130, a cropped image with examined object 134, a processed version of image 130 (e.g., one where the color of at least part of the pixels of image 130 was corrected based on colorized surface 132), or data derived from image 130. In a one aspect of the disclosure, examined object 134 may be a skin feature. According to another aspect of the disclosure, examined object 134 may include a reagent, such as a dipstick with one or more reagent pads.

Process 190 may continue when medical analysis unit 140 determines test results associated with a state of examined object 134, possibly taking into account local illumination conditions and/or image capturing settings effects. In other words, medical analysis unit 140 may inspect the image of examined object 134 after the effects of the local illumination conditions and/or of the effects of the image capturing settings are removed. In another example, medical analysis unit 140 may inspect the image of examined object 134 with a function that takes into account local illumination conditions and/or image capturing settings effects. When examined object 134 is a dipstick, determining its state may include determining an extent of a chemical reaction on a least one reagent pad of the dipstick. When examined object 134 is a skin feature, determining the object's state may include determining its condition, for example relative to a previous record of the skin feature. In a first example, when the skin feature is a wound, medical analysis unit 140 may determine from the image data its healing progress. In a second example, when the skin feature is a mole, medical analysis unit 140 may determine from the image data the likelihood that the mole changed in size or that it has an increased risk of being cancerous. Thereafter, medical analysis unit 140 may transmit the test results to healthcare provider 160 (step 195), and/or to other entities (such as user 110, medical practitioner 120, insurance company 170, pharmacy 180, and so forth).

Process 190 may continue when healthcare provider 160 initiates an action based on the received test results. In one embodiment, initiating an action based on the received test results may include presenting the test results to medical practitioner 120 (e.g., the user's physician). In another embodiment, initiating an action based on the received test results may include updating an electronic medic record (EMR) of user 110. In another embodiment, initiating an action based on the received test results may include generating a prescription and automatically (or semi-automatically) forwarding it to pharmacy 180. In another embodiment, initiating an action based on the received test results may include sending medical information to user 110 (step 196) or permitting medical analysis unit 140 to send medical information to user 110. The medical information transmitted to user 110 may include the test results, an invitation to schedule an appointment, a prescription, an indication that the user may be eligible for a different insurance coverage, or any other action that results from the test.

FIG. 1C is a message flow diagram illustrating communications exchanges between different entities implementing the process of FIG. 1B. It is to be understood that the process may be modified consistent with embodiments disclosed herein.

Figure 2:
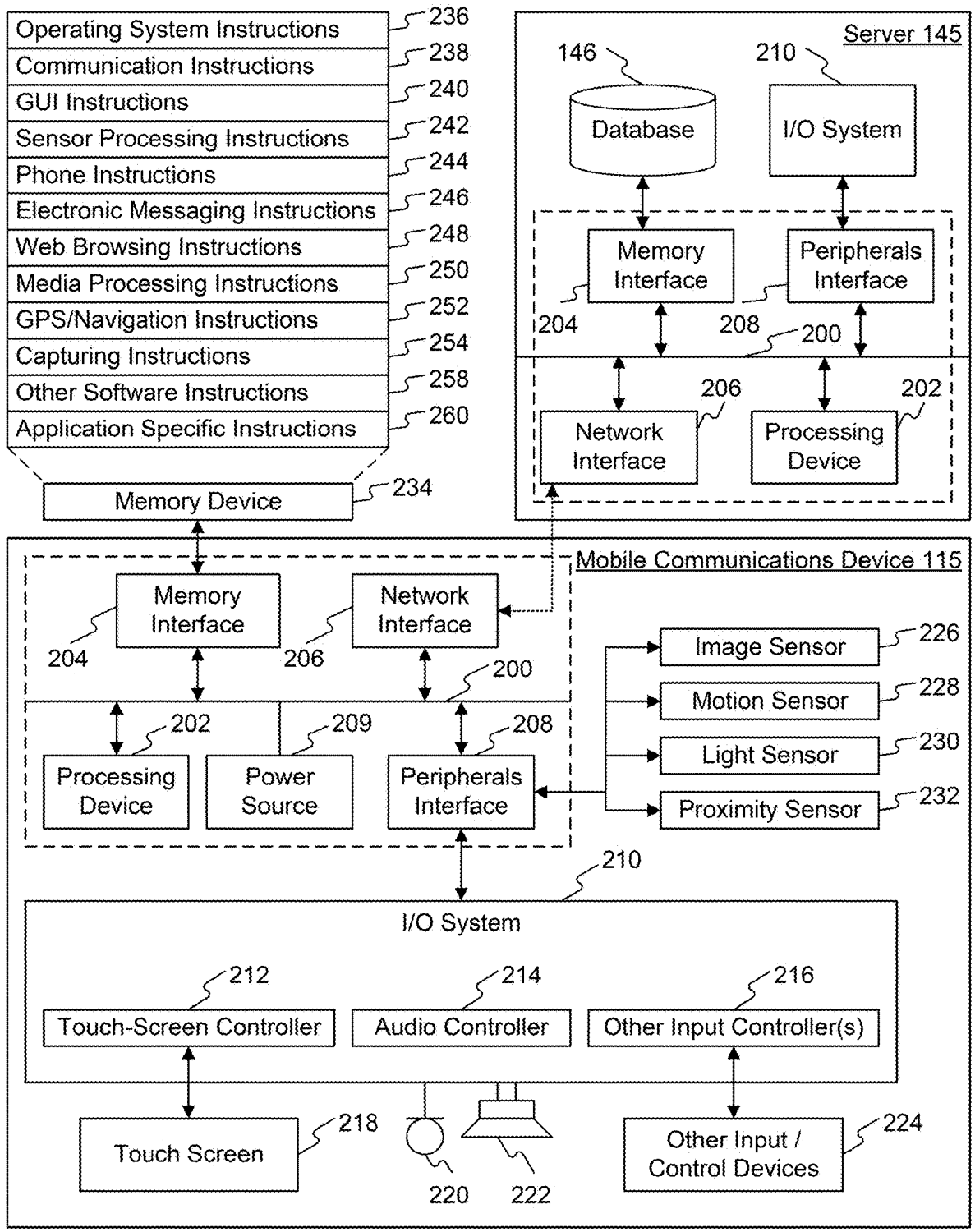
FIG. 2 is a block diagram illustrating some of the components of the system of FIG. 1A, consistent with the present disclosure.

FIG. 2 is an exemplary block diagram of configurations of server 145 and mobile communications device 115. In one embodiment, server 145 and mobile communications device 115 directly or indirectly accesses a bus 200 (or other communication mechanism) that interconnects subsystems and components for transferring information within server 145 and/or mobile communications device 115. For example, bus 200 may interconnect a processing device 202, a memory interface 204, a network interface 206, a peripherals interface 208 connected to I/O system 210, and power source 209.

Processing device 202, shown in FIG. 2, may include at least one processor configured to execute computer programs, applications, methods, processes, or other software to perform embodiments described in the present disclosure. For example, the processing device may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing device may include at least one processor configured to perform functions of the disclosed methods such as a microprocessor manufactured by Intel™. The processing device may include a single core or multiple core processors executing parallel processes simultaneously. In one example, the processing device may be a single core processor configured with virtual processing technologies. The processing device may implement virtual machine technologies or other technologies to provide the ability to execute, control, run, manipulate, store, etc., multiple software processes, applications, programs, etc. In another example, the processing device may include a multiple-core processor arrangement (e.g., dual, quad core, etc.) configured to provide parallel processing functionalities to allow a device associated with the processing device to execute multiple processes simultaneously. It is appreciated that other types of processor arrangements could be implemented to provide the capabilities disclosed herein.

In some embodiments, processing device 202 may use memory interface 204 to access data and a software product stored on a memory device or a non-transitory computer-readable medium. For example, server 145 may use memory interface 204 to access data structure 146. As used herein, a non-transitory computer-readable storage medium refers to any type of physical memory on which information or data readable by at least one processor can be stored. Examples include random access memory (RAM), read-only memory (ROM), volatile memory, nonvolatile memory, hard drives, CD ROMs, DVDs, flash drives, disks, any other optical data storage medium, any physical medium with patterns of holes, a RAM, a PROM, and EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within mobile communications device 115, server 145, or at a remote location. Additionally, one or more computer-readable storage mediums can be utilized in implementing a computer-implemented method. The term "computer-readable storage medium" should be understood to include tangible items and exclude carrier waves and transient signals.

Both mobile communications device 115 and server 145 may include network interface 206 coupled to bus 200. Network interface 206 may provide two-way data communications to a network, such as network 150. In FIG. 2, the wireless communication between mobile communications device 115 and server 145 is represented by a dashed arrow. In one embodiment, network interface 206 may include an integrated services digital network (ISDN) card, cellular modem, satellite modem, or a modem to provide a data communication connection over the Internet. As another example, network interface 206 may include a wireless local area network (WLAN) card. In another embodiment, network interface 206 may include an Ethernet port connected to radio frequency receivers and transmitters and/or optical (e.g., infrared) receivers and transmitters. The specific design and implementation of network interface 206 may depend on the communications network(s) over which mobile communications device 115 and server 145 are intended to operate. For example, in some embodiments, mobile communications device 115 may include network interface 206 designed to operate over a GSM network, a GPRS network, an EDGE network, a Wi-Fi or WiMAX network, and a Bluetooth® network. In any such implementation, network interface 206 may be configured to send and receive electrical, electromagnetic or optical signals that carry digital data streams representing various types of information.

Both mobile communications device 115 and server 145 may also include peripherals interface 208 coupled to bus 200. Peripherals interface 208 may be connected to sensors, devices, and subsystems to facilitate multiple functionalities. In one embodiment, peripherals interface 208 may be connected to I/O system 210 configured to receive signals or input from devices and to provide signals or output to one or more devices that allow data to be received and/or transmitted by mobile communications device 115 and server 145. In one example, I/O system 210 may include a touch screen controller 212, audio controller 214, and/or other input controller(s) 216. Touch screen controller 212 may be coupled to a touch screen 218. Touch screen 218 and touch screen controller 212 may, for example, detect contact, movement or break thereof using any of a plurality of touch sensitivity technologies, including but not limited to capacitive, resistive, infrared, and surface acoustic wave technologies as well as other proximity sensor arrays or other elements for determining one or more points of contact with the touch screen 218. Touch screen 218 may also, for example, be used to implement virtual or soft buttons and/or a keyboard. While a touch screen 218 is shown in FIG. 2, I/O system 210 may include a display screen (e.g., CRT or LCD) in place of touch screen 218. Audio controller 214 may be coupled to a microphone 220 and a speaker 222 to facilitate voice-enabled functions, such as voice recognition, voice replication, digital recording, and telephony functions. The other input controller(s) 216 may be coupled to other input/control devices 224, such as one or more buttons, rocker switches, thumbwheel, infrared port, USB port, and/or a pointer device such as a stylus.

With regard to mobile communications device 115, peripherals interface 208 may also be connected to an image sensor 226, a motion sensor 228, a light sensor 230, and/or a proximity sensor 232 to facilitate image capturing, orientation, lighting, and proximity functions. Other sensors (not shown) may also be connected to the peripherals interface 208, such as a temperature sensor, a biometric sensor, or other sensing devices to facilitate related functionalities. In addition, a GPS receiver may also be integrated with, or connected to, mobile communications device 115, such as GPS receivers typically integrated into mobile communications devices. Alternatively, GPS software may permit a mobile communications device to access AN external GPS receiver (e.g., connecting via a serial port or Bluetooth).

Consistent with the present disclosure, mobile communications device 115 may use memory interface 204 to access memory device 234. Memory device 234 may include high-speed random-access memory and/or non-volatile memory such as one or more magnetic disk storage devices, one or more optical storage devices, and/or flash memory (e.g., NAND, NOR). Memory device 234 may store an operating system 236, such as DARWIN, RTXC, LINUX, iOS, UNIX, OSX, WINDOWS, or an embedded operating system such as VxWorks. The operating system 236 may include instructions for handling basic system services and for performing hardware-dependent tasks. In some implementations, the operating system 236 may be a kernel (e.g., UNIX kernel).

Memory device 234 may also store communication instructions 238 to facilitate communicating with one or more additional devices, one or more computers and/or one or more servers. Memory device 234 may include: graphical user interface instructions 240 to facilitate graphic user interface processing; sensor processing instructions 242 to facilitate sensor-related processing and functions; phone instructions 244 to facilitate phone-related processes and functions; electronic messaging instructions 246 to facilitate electronic-messaging related processes and functions; web browsing instructions 248 to facilitate web browsing-related processes and functions; media processing instructions 250 to facilitate media processing-related processes and functions; GPS/navigation instructions 252 to facilitate GPS and navigation-related processes and instructions; capturing instructions 254 to facilitate processes and functions related to image sensor 226; and/or other software instructions 258 to facilitate other processes and functions. Memory device 234 may also include application specific instructions 260 to facilitate a process for guiding user 110 on the steps of the medical testing. For example, application specific instructions 260 may cause display of a massage indicative of image insufficiency for medical testing.

Each of the above identified instructions and applications may correspond to a set of instructions for performing one or more functions described above. These instructions need not be implemented as separate software programs, procedures, or modules. Memory device 234 may include additional instructions or fewer instructions. Furthermore, various functions of mobile communications device 115 may be implemented in hardware and/or in software, including in one or more signal processing and/or application specific integrated circuits. For example, mobile communications device 115 may execute an image processing algorithm to identify objects in a received image. In addition, the components and arrangements shown in FIG. 2 are not intended to limit the disclosed embodiments. As will be appreciated by a person skilled in the art having the benefit of this disclosure, numerous variations and/or modifications may be made to the depicted configuration of server 145. For example, not all components may be essential for the operation of server 145 in all cases. Any component may be located in any appropriate part of server 145, and the components may be rearranged into a variety of configurations while providing the functionality of the disclosed embodiments. For example, some servers may not include all of the elements in I/O system 210.

Figure 3:
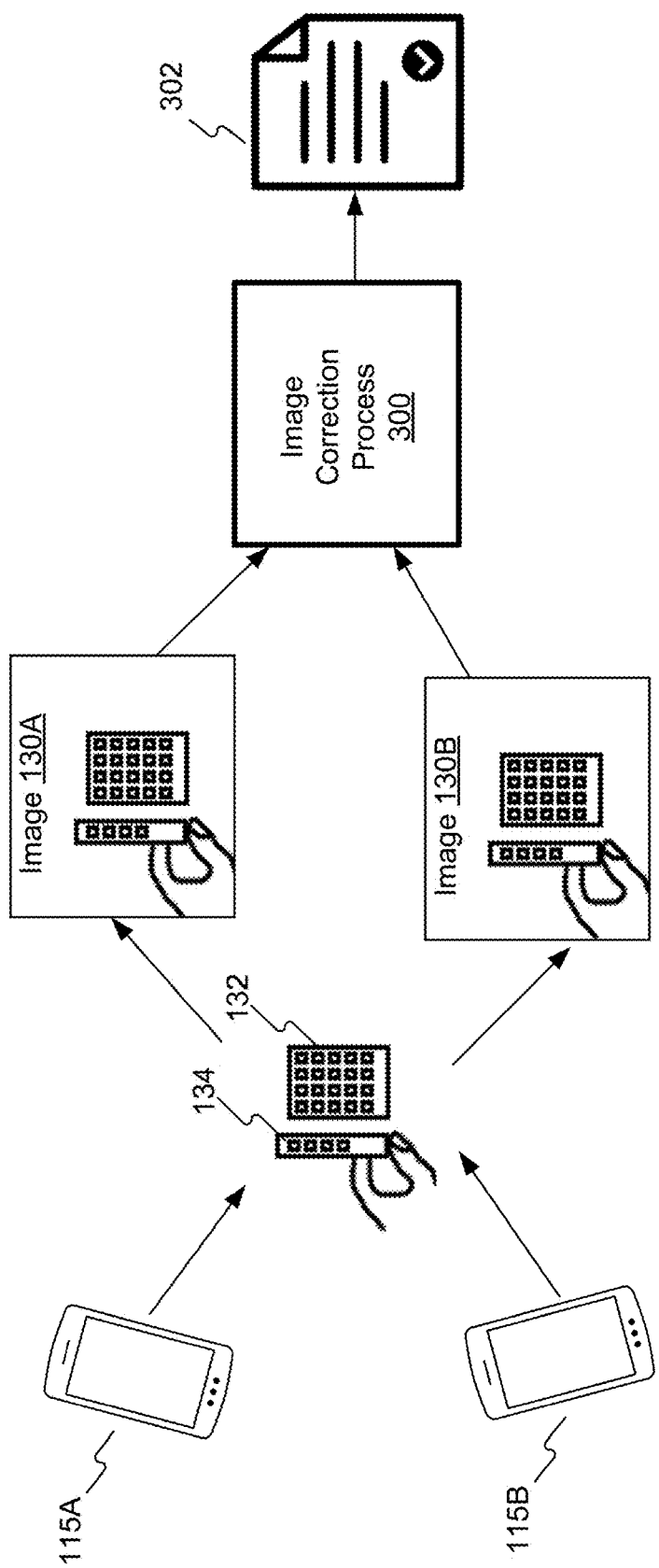
FIG. 3 is a schematic illustration of how two different mobile communications devices can obtain the same test results, consistent with the present disclosure.

As mentioned above, one of the challenges of turning a smartphone into a regulatory-approved clinical device is the lack of uniformity of image capture capabilities of smartphones. FIG. 3 illustrates two communication devices 115 capturing the same object. When a first mobile communications device 115A captures examined object 134 in proximity to colorized surface 132, a first image 130A is acquired. When a second mobile communications device 115B captures examined object 134 in proximity to colorized surface 132, a second image 130B is acquired. First image 130A may be different from second image 130B due to differences between the incorporated image sensors, differences in lighting conditions from different perspectives, and/or differences in image sensor settings. For example, first image 130A may be different from second image 130B because first mobile communications device 115A has different white balance settings and different color correction profiles than second mobile communications device 115B. The white balance settings may be associated with how communication devices 115 determines the white point for the image and if any tint should be applied to the other colors. The color correction profile may be associated with how communication devices 115 process color saturation, black levels, highlights, and the contrast of colors in the image. In another example, first image 130A may be different from second image 130B because first mobile communications device 115A has different hardware (such as image sensor resolution, dimensions, filters, color filters, lenses, crop factor, sensitivity, and so forth). In yet another example, first image 130A may be different from second image 130B because first mobile communications device 115A has different camera configuration (such as exposure time, shutter speed, aperture, ISO, and so forth).

Consistent with the present disclosure, each of image 130A and image 130B may undergo an image correction process 300. Image correction process 300 may include one or more steps to remove (or to compensate for) local illumination effects and image capturing settings effects. The local illumination effects may result from the type of light source used to light the object, the distance of the object from the light source, a viewing angle of the object, position of the object, ambient light conditions, flash usage, exposure time, and so forth. The image capturing settings effects result from the type of image sensor 226 used to capture the object, image resolution, frame rate, gain, ISO, shutter speed, stereo base, lens, focus, zoom, color correction profile, and so forth. In some embodiments of the disclosure, correcting captured image 130 may include reversing any of the tone mapping, color enhancement, white balance, and contrast enhancing of image 130. In addition, correcting image 130 may include simulate standard illumination conditions and reduce shading and specular effects.

Image correction process 300 is enabled through the use of colorized surface 132. Specifically, the qualities of one or more color swaths on colorized surface 132 may be known in advance. To the extent differences are detected between the actual colors of colorized surface 132 and an image such as image 130A or image 130B, the system may calculate a correction factor necessary to rectify and such differences, and then apply that correction factor to the captured image of object 134.

Image correction process 300 may correct each of image 130A and image 130B differently. For example, image correction process 300 may include increasing the red color in image 130A and adding brightness to image 130B. After images 130A and 130B separately undergo image correction process 300, system 100 may independently determine test results 302 from each of image 130A and image 130B. In accordance with the present disclosure, even though image 130A may be different from image 130B, test results 302 will be the same because both images captured the same known colorized surface 132 whose colorization is known in advance, and which may be used as a basis for generating different correction factors for the varying differences. In some embodiments, system 100 may correct captured image 130A/130B using metadata associated with the mobile communications device that captured image 130. In other embodiments, system 100 may correct captured image 130 without using any information about the mobile communications device that captured image 130.

Figure 4A:
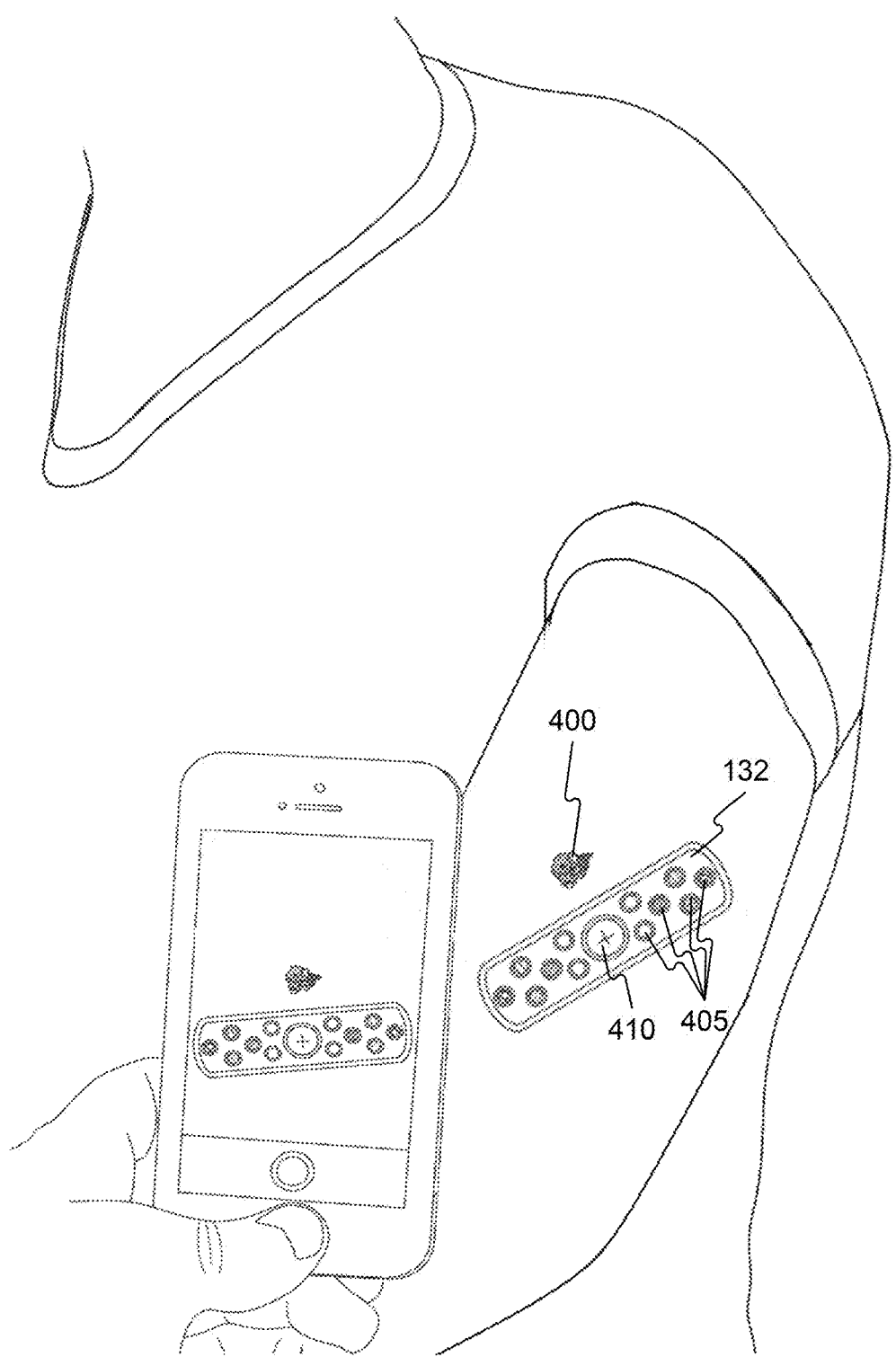
FIG. 4A is an illustration of one aspect of the disclosure where the examined object is a tissue feature.
Figure 4B:
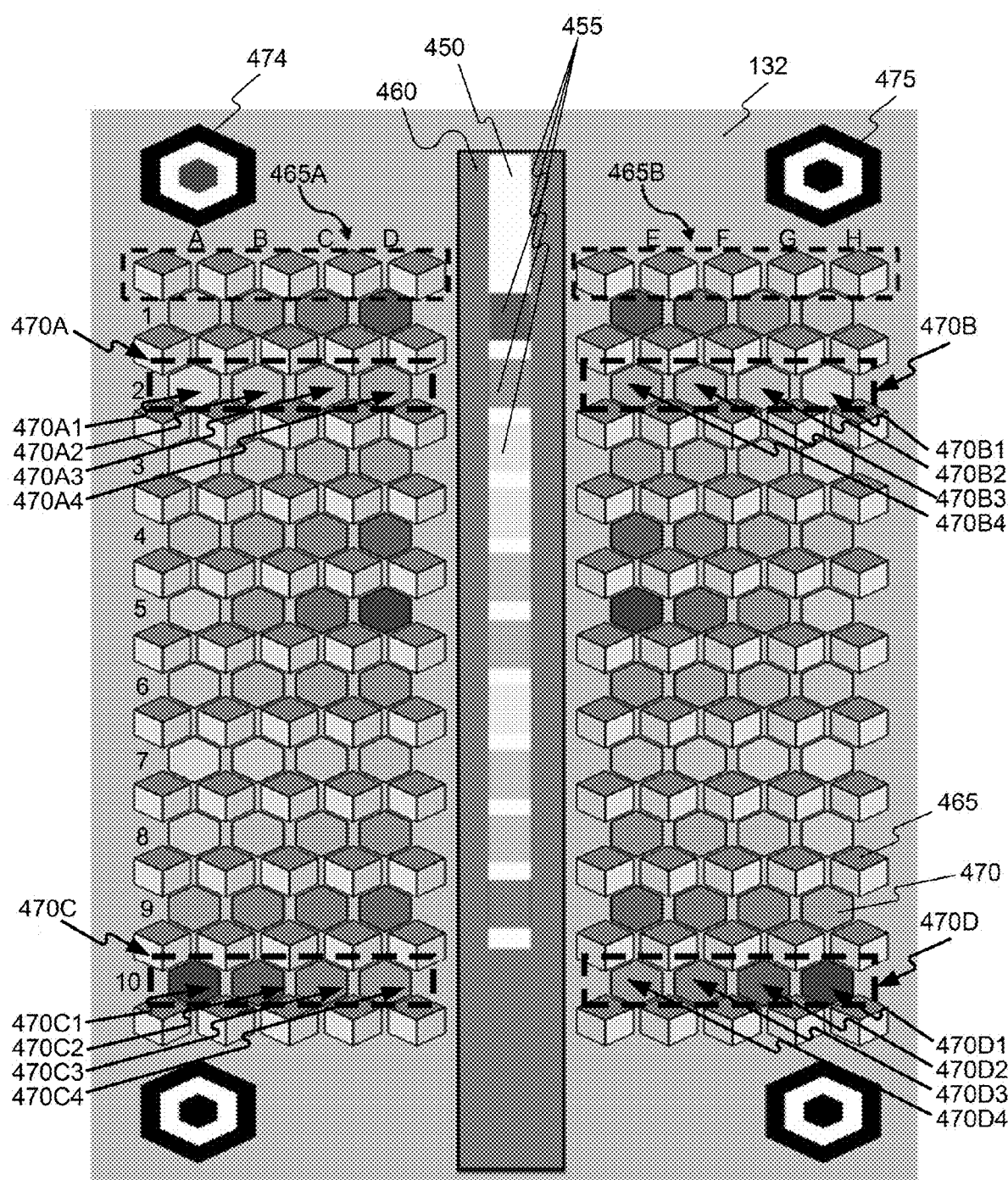
FIG. 4B is an illustration of another aspect of the disclosure where the examined object is a dipstick.

FIG. 4A depicts one embodiment where the examined object is a skin feature 400. Consistent with this aspect, system 100 is configured to measure the distribution of colors of skin feature 400 by comparing them to the colors on colorized surface 132. The colors on colorized surface 132 may be selected to include an at least some of the expected range of colors of the examined object under various illumination and capturing conditions. It may also include a range of colors from which a correction factor may be generated. As illustrated in FIG. 4A, colorized surface 132 may include a plurality of colored reference elements 405 and may be attachable onto a skin area next to skin feature 400. In certain embodiments, colorized surface 132 may have different forms adapted to a medical condition of user 110 or an expected form and characteristics of skin feature 400. In addition, colorized surface 132 may have different forms adapted to the expected capturing parameters (e.g., to capturing geometry). For example, colorized surface 132 may be round, elongated, curved, have one or more openings therein to accommodate skin feature 400, etc.

Consistent with the present disclosure, colorized surface 132 may have one or more colored reference elements 405 used for calibrating illumination and capturing conditions rather than or in addition to relating to colored reference elements 405 associated with the expected colors in skin feature 400. When skin feature 400 and colorized surface 132 are captured in a single image, system 100 may determine the true colors of captured skin feature 400 by correcting image 130. In some embodiments, colorized surface 132 may also include one or more positioning marks 410 that may be used for image processing purposes and/or for positioning colorized surface 132 accurately with respect to skin feature 400. Moreover, positioning marks 410 may provide a reference of a known dimension that may be used to estimate a size, orientation, and/or a form of skin feature 400. In certain embodiments, dimensional marks 410 may be used (e.g., by image analysis unit 140) to correct captured image 130 with respect to dimensions and forms and to derive an analysis of size and/or form of skin feature 400 and possibly of other image features. For example, image analysis unit 140 may compute the color constancy to determine whether two pixels have the same color in the real world regardless of illumination conditions and/or camera parameters.

In some embodiments, system 100 may provide two dimensional measurements of different sections of skin feature 400 associated with a same color, such as size and shape characteristics (symmetry, boundary length etc.). In additional embodiments, system 100 may track skin feature parameters over time by repeatedly capturing the same skin feature over time. In this regard, the dimensional mark may assist in determining variations over time. In one example, skin feature 400 may include scar tissue or a rash that may be monitored daily to track healing progress. In another example, skin feature 400 may be captured weekly or even monthly for monitoring potentially cancerous features or developments. When collecting such data over a period of time, an additional step may be added for verifying that the correction of image 130 is consistent across the time period in which the data was collected. Correcting image 130 may further include taking into account illumination conditions and capturing parameters associated with previously captured images. Additional details on the first aspect of the disclosure are described in Applicant's U.S. Pat. No. 10,362,984, which is incorporated herein by reference in its entirety.

FIG. 4B provides an example of a colorized surface for use with a dipstick 450 having at least one reagent pad 455. The terms "reagent pads" and "colored test reagent pads" may be used interchangeably herein to refer to the testing areas on a dipstick. As shown, colorized surface 132 may include a dipstick placement region 460 and a plurality of calibration elements. The calibration elements may have been selected to correspond to the type of dipstick 450. Specifically, the calibration elements may include a plurality of grey elements 465, and a plurality of colored reference elements 470. Colorized surface 132 may also be provided with high contrast elements 475 for enabling fast binary large object based (BLOB) colorized surface rectification on mobile communications device 115 (illustrated, by way of example only, in FIGS. 1A, 2, 3, and 6).

Consistent with the present disclosure, colorized surface 132 may include a plurality of grey elements 465 that exhibit various shades of gray for improved gamma correction. Colorized surface 132 may also include a plurality of colored reference elements 470 that may be selected to represent at least some of the expected range of colors of the examined object under various possible illumination conditions and various image processing capabilities of possible image capturing devices. The colored reference elements 470 may be surrounded by borders for minimizing over smoothing of certain colors by some camera models. In addition, to assist image processing, the color of dipstick placement region 460 may be more than 25%, 50%, or 75% darker than (or brighter than) the colors of plurality of colored reference elements. Alternatively, the color of dipstick placement region 460 may be more than 25%, 50%, or 75% visibly different in other ways from the colors of the plurality of colored reference elements.

The non-limiting example of colorized surface 132 depicted in FIG. 4B shows calibration elements 465 and 470 with geometrical shapes that differ from the geometrical shapes of the reagent pads on dipstick 450. The geometrical shapes may be selected to enable differentiation between reagent pads 455 and calibration elements 465 and 470 on colorized surface 132. Specifically, colorized surface 132 may include a plurality of cube-like grey elements 465 having three sides, each having a different shade of grey; and a plurality of hexagon-shaped colored reference elements 470 used as reference values for image color correction. On the depicted colorized surface 132, at least two groups of grey elements (e.g., group of grey elements 465A and group of grey elements 465B) and at least two groups of colored reference elements (e.g., group of colored reference elements 470A and group of colored reference elements 470B) may be located on opposing sides of dipstick placement region 460.

Consistent with embodiments of the present disclosure, colorized surface 132 may include at least two groups with the same color scheme and the same shade scheme. The term "the same color scheme" means that the groups may have a combination of elements with the same one or more color families but not necessarily presented in the same order. Hue is well known in the art and may be defined as the angle of the color when mapped into a color space (hue ranges from 0-360 degrees), and the term "color family" may depend on a desired level of accuracy, and may refer to colors within a hue range of about 4 to 8 degrees, within a hue range of about 1 to 2 degrees, within a hue range of about 10 to 20 arc minutes, and so forth. Similarly, the term "the same shade scheme" means that the groups may have a combination of elements with the same level of shade but not necessarily presented in the same order. Colors that vary by shade have a different level of darkness, but otherwise share a similar hue and relative chroma. When the shade is defined in a scale of 1 to 50, the same level of shade may refer to two elements having a shade value that varies by ±1, by ±0.1, by ±0.01, and so forth, depending on a desired level of accuracy.

As mentioned above, the plurality of colored reference elements 470 on colorized surface 132 may represent at least some of the expected range of colors of the examined object (for example, after going through different chemical processes, under various possible illumination conditions, and under various image processing capabilities of differing image capture devices). On the colorized surface depicted in FIG. 4B, the letters A-H and the numbers 1-10 are added for discussion purposes, to demarcate an 8×10 matrix of colored reference elements 470. The following table provides example values for the plurality of colored reference elements 470 in the form of color codes. Each color code is a six-digit code used in HTML, CSS, SVG, and other computing applications to represent the specific color used in the corresponding colored reference element.

|   | A | B | C | D | E | F | G | H |
|---|---|---|---|---|---|---|---|---|
| 1 | cfbf6a | 9c986f | 5c876c | 246c6a | 246c6a | 5c876c | 9c986f | cfbf6a |
| 2 | d5d2ce | dbafb7 | dd9ea4 | d98a98 | d98a98 | dd9ea4 | dbafb7 | d5d2ce |
| 3 | d3cdcd | d9b0b9 | cea099 | d28c84 | d28c84 | cea099 | d9b0b9 | d3cdcd |
| 4 | bfb99c | ae9d9d | 9a7e8b | 7b506d | 7b506d | 9a7e8b | ae9d9d | bfb99c |
| 5 | d7d473 | a59762 | 5f736c | 204d58 | 204d58 | 5f736c | a59762 | d7d473 |
| 6 | d4ca7b | c5b172 | a8a478 | 949575 | 949575 | a8a478 | c5b172 | d4ca7b |
| 7 | dbd8d5 | ddc9bf | e0b9af | e3ac9a | e3ac9a | e0b9af | ddc9bf | dbd8d5 |
| 8 | cacac6 | c4bcaf | b4a7ba | 9f8ba0 | 9f8ba0 | b4a7ba | c4bcaf | cacac6 |

-continued

|   | A | B | C | D | E | F | G | H |
|---|---|---|---|---|---|---|---|---|
| 9 | d0976b | ae7880 | 7e7e91 | 536c98 | 536c98 | 7e7e91 | ae7880 | d0976b |
| 10 | 294e57 | 62623f | a08640 | dd8d24 | dd8d24 | a08640 | 62623f | 294e57 |

In one embodiment, dipstick 450 may include a number of reagent pads 455, and colorized surface 132 may include at least the same number of groups of colored reference elements with the same color scheme and the same shade scheme (e.g., multiple groups of differing shades and a same color such as groups 470A and 470B). In another embodiment, at least one group of colored reference elements may be used in calculating a normalized value (such as a normalized color) for a first reagent pad and at least one other group of colored reference elements may be used in calculating a normalized value (such as a normalized color) for a second reagent pad. In addition, different groups of colored reference elements may be used for detecting different reactions in a single reagent pad or in different reagent pads. In one embodiment, one or more groups of colored reference elements may be used in calculating a normalized value (such as a normalized color) for both the first reagent pad and the second reagent pad.

In the colorized surface illustrated in FIG. 4B, groups 465A and 465B serve as a first example of two groups that share the same color scheme and the same shade scheme. Each of groups 465A and 465B has five elements of a single color (in this example, gray color), and with all the elements in each group sharing the same three shades. Groups 470A and 470B serve as a second example of two groups with the same color scheme and the same shade scheme. Both groups 470A and 470B have four elements in differing shades of exactly or substantially a single color (in this example, pink). In this example, group 470B is a mirror image of group 470A. Specifically, 470A1 has the same level of shade as 470B1, 470A2 has the same level of shade as 470B2, 470A3 has the same level of shade as 470B3, and 470A4 has the same level of shade as 470B4. In some embodiments, colorized surface 132 may include at least two colored reference elements of differing shades of a same color. The at least two colored reference elements may be located adjacent each other and on a same side of dipstick placement region 460 (for example, colored reference elements 470A2 and 470A3); or be located on opposing sides of dipstick placement region 460 (for example, colored reference elements 470A2 and 470B3).

Groups 470C and 470D serve as a third example to two groups sharing the same color scheme and the same shade scheme. Both groups 470C and 470D have four elements with the same four differing colors and exactly or substantially a single shade. Specifically, 470C1 is of the same color family as 470D1, 470C2 is of the same color family as 470D2, 470C3 is of the same color family as 470D3, and 470C4 is of the same color family as 470D4.

The plurality of calibration elements associated with colorized surface 132 may have an axis of reflection symmetry in the middle of dipstick placement region 460. However, other colorized surfaces may have different types of symmetry (e.g., rotational symmetry, or translational symmetry), with different symmetry axes, or no symmetry at all. Consistent with the present disclosure, colorized surface 132 may include a plurality of pairs of colored reference elements. Members of a pair of colored reference elements may share substantially a same color (for example, same color family, exactly or approximately the same distribution of color components with different magnitude, etc.) and share substantially a same shade (i.e., same level of shade). When colorized surface 132 has a certain type of symmetry, the members of each pair of colored reference elements are substantially indistinguishable from each other. In one embodiment, the first and the second colored reference elements of a pair of colored reference elements may be detected in a captured image on opposing sides of colorized surface 132. In the depicted example, dipstick placement region 460 may be positioned between the pairs colored reference elements. For example, 470A1 and 470B1 may form a first pair of colored reference elements, 470A2 and 470B2 may form a second pair of colored reference elements, 470A3 and 470B3 may form a third pair of colored reference elements, and 470A4 and 470B4 may form a fourth pair of colored reference elements.

As shown in FIG. 4B, colorized surface 132 may include at least ten pairs of colored reference elements 470. Alternative embodiments may include more or less pairs. For example, alternative embodiments may include at least twenty pairs of colored reference elements 470, at least thirty pairs of colored reference elements 470, or even more. As is described in succeeding paragraphs, the pairs of colored reference elements may be used to provide a color baseline for comparison with the reagent pads. For example, unless for the relative position of the color board with respect to the image sensor, and different illumination conditions at the locations of the two or more reference elements, two or more reference elements that share a same color and shade would be expected by the system to appear identically in a captured image, or may be expected to have particular appearances based on their relative positions, given that the positions are known in advance. (i.e., coordinates of each reference element within the color board are known, for example with respect to other elements of the color board, such as position markers 474 and 475.) Moreover, if a reference element color is known in advance as is the case with the colored surface whose colors may be precisely controlled during printing, any differences determined through image capture may be corrected by the system in order to ensure that an accurate reading is achieved. (i.e., a correction factor may be applied to the reagent pad to correct for differences between expected colors and shades of captured reference elements and the colors actually detected as the result of image capture). Therefore, when two or more reference elements that share a same color and shade appear different in the captured image, the difference between them may be attributed to the relative position of the color board with respect to the image sensor and/or to the different illumination conditions at the locations of the two or more reference elements. Based on the known coordinates of the two or more reference elements, this measured effect may be interpolated and/or extrapolated to estimate the effect of the relative position of the color board with respect to the image sensor and/or of the different illumination conditions at a selected location, such as a location of a reagent pad. Moreover, in some embodiments, the relative position of different regions (such as a region of a reference element, a region of a reagent pad, etc.) with respect to the image sensor may be determined (for example using geometrical pose estimation algorithms, using a machine learning model trained to determine the relative position of the color board, etc.), and the interpolation and/or extrapolation may be further based on the determined relative positions of the two or more reference elements and the reagent pad.

Generally, colorized surface 132 may include more colored reference elements 470 than an expected number of reagent pads 455 on dipstick 450. In the illustrated example, dipstick 450 includes ten reagent pads 455, and colorized surface 132 includes eighty colored reference elements 470. Consistent with the present disclosure, the number of colored reference elements 470 on colorized surface 132 may be at least two times, four times, six times, or more than the number of reagent pads 455 on dipstick 450. Additional details pertaining to this disclosure are described in Applicant's U.S. Pat. No. 10,068,329, which is incorporated herein by reference in its entirety.

Figure 5A:
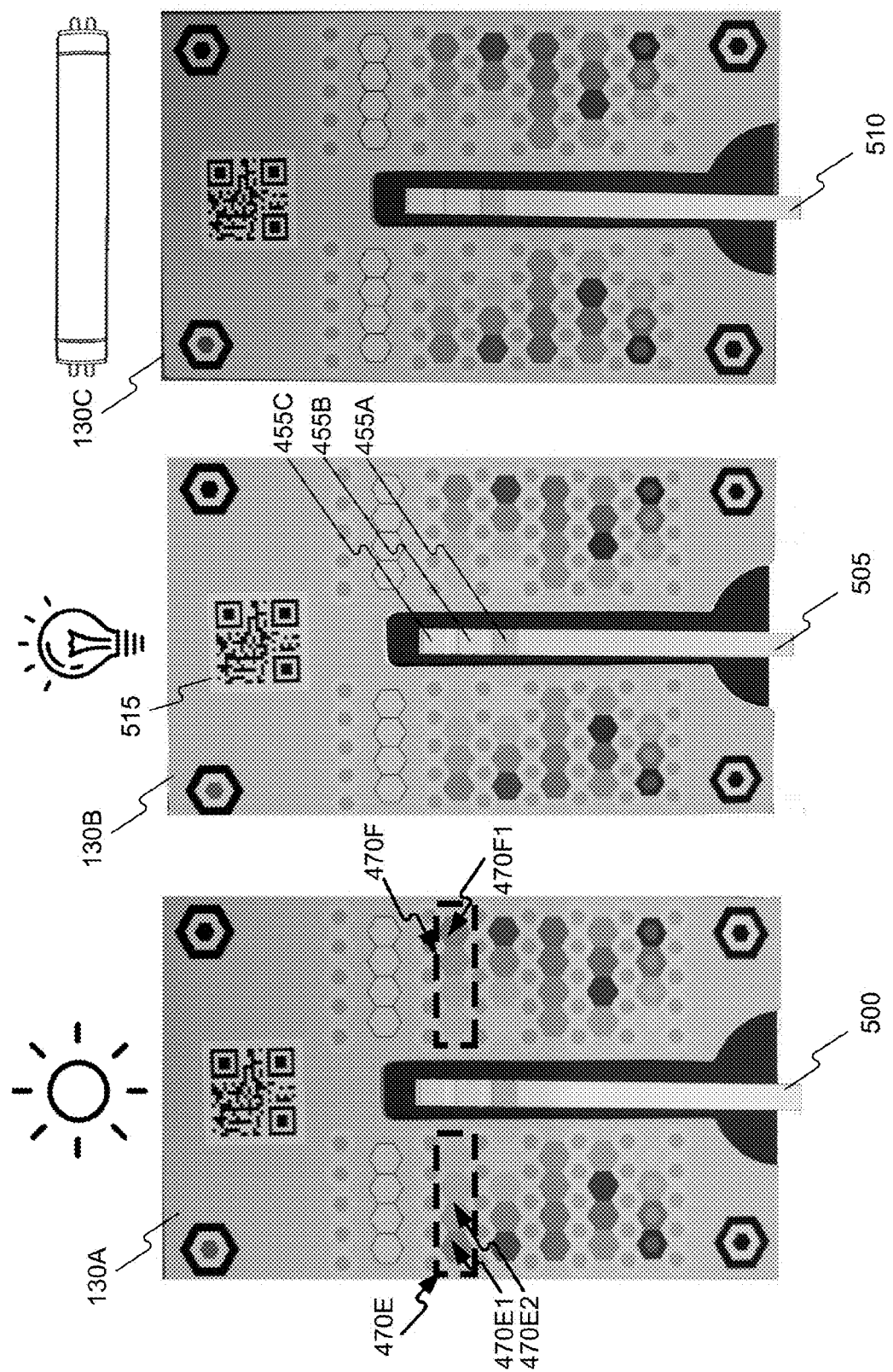
FIG. 5A depicts three images of a same reagent captured in different illumination conditions.

FIG. 5A depicts three images 130 of a dipstick for diagnosing a Urinary Tract Infection (UTI). The UTI dipstick includes three reagent pads, a first reagent pad 455A for measuring blood in the urine, a second reagent pad 455B for measuring Nitrite in the urine, and a third reagent pad 455C for measuring Leukocytes in the urine. Each one of the images was captured under different illumination conditions. Specifically, image 130A includes a depiction 500 of a UTI dipstick that was captured under daylight, image 130B includes a depiction 505 of a UTI dipstick that was captured under tungsten bulb light, and image 130C includes a depiction 510 of a UTI dipstick that was captured under fluorescent light. As shown in the figure, images 130A, 130B, and 130C vary in color due to the differing lighting conditions. The color boards depicted in FIG. 5A also includes a unique QR code 515 that may reflect specific chromatic properties associated with at least some of the plurality of colored reference elements at a time of printing. The unique QR code may be machine readable to enable a processing device (e.g., server 145) to later normalize a comparison color, for determining chromatic properties of at least one of the examined objects.

As mentioned above, the colorized surface enables processing of the image to determine the colors of the examined object (e.g., the UTI dipstick), irrespective of local illumination conditions and image capturing settings effects. In other words, the system may allow for accurate diagnostic results, across various lighting conditions, across various image capture settings, and across various image capture devices. To determine the colors of the examined object, each colored reference elements may be associated with a known color (for example, lightness, chroma, saturation, CYMK values, RGB values, and so forth). In one example, the known color may be determined by the type of the colorized surface. In another example, the known color may be obtained using method 1100 and/or using step 1106 as described below. The appearance of the colored reference element in an image (e.g., image 130) may be analyzed to determine the perceived color of the colored reference element in the image (for example, brightness, colorfulness, saturation, CYMK values, RGB values, and so forth). The known color may be compared with the perceived color to determine the effects of local illumination conditions and/or the effects of image capturing settings on the perceived color. For example, brightness and colorfulness (or a function thereof) may be compared with the lightness and chroma (or a function thereof). Consistent with the present disclosure, the determined effects of the local illumination conditions and/or the determined effects of the image capturing settings on the perceived color may be measured as a transformation function, as a parameter to a transformation function, as a magnitude of the effect, and so forth. In one embodiment, the determined effects on the perceived color at two or more colored reference elements positioned at known locations may be extrapolated and/or interpolated to estimate the effects of the local illumination conditions and/or the effects of the image capturing settings on a perceived color of a colored reference element positioned at a different location. For example, extrapolation and/or interpolation algorithms may be used to determine the effects of the local illumination conditions and/or the effects of the image capturing settings on a perceived color of a colored reference element positioned at a known location. Some non-limiting examples of such extrapolation and/or interpolation algorithms may include linear, polynomial, conic, piecewise constant, spline, and so forth.

Consistent with the present disclosure, a machine learning model may be trained using training examples to estimate the effects of the local illumination conditions and/or the effects of the image capturing settings on perceived colors of selected colored reference elements from images of colored reference elements. The trained machine learning model may be used to estimate the effects on a perceived color of a selected colored reference element from the appearance of a plurality of colored reference elements in reference image data. The trained machine learning model may also be used for calculating normalized colors of selected colored reference elements from reference image data and/or estimate the normalized color of a selected element from the reference image data. In one embodiment, the training examples may include image data of a plurality of colored reference elements and a selected colored reference element, together with an indication of the effects of the local illumination conditions and/or the effects of the image capturing process on a perceived color of the selected colored reference element. In another embodiment, the training examples may include image data of a plurality of colored reference elements and a selected colored reference element, together with an indication of the desired normalized color of the selected colored reference element.

In one implementation, the estimated effects of the local illumination conditions and/or the estimated effects of the image capturing settings on a perceived color of a selected color reference element may be used to reverse the effects to obtain a normalized appearance of the selected color reference element. For example, the estimated effects may be in a form of a function, and an inverse of the function may be applied to the appearance of the selected color reference element to obtain the normalized appearance of the selected color reference element. In another example, the estimated effects may be in a form of a factor, and the factor may be used to calculate the normalized appearance of the selected color reference element from the appearance of the color reference selected element.

FIG. 5A also depicts a version of colorized surface 132 different from the version of colorized surface 132 depicted in FIG. 4B. Consistent with the present disclosure, the calibration elements of a colorized surface may have been selected to correspond to the type of dipstick being examined. Specifically, this version of colorized surface may include calibration elements (i.e., the grey elements and the colored reference elements) with visual characteristics associated with UTI dipsticks. For example, the number of colored reference elements may be forty not eighty, the color families of colored reference elements may differ, the gray elements may be hexagonal, the colored reference elements may not be surrounded by borders, and any other feature or color may be changed so long as the intended function described herein is achieved. Thus, FIG. 4B is but one example of a colorized surface that may to be used to determine an extent of a chemical reaction on a UTI dipstick irrespective of local illumination conditions and/or irrespective of effects of image capturing settings. The exemplary version of colorized surface 132 illustrated in FIG. 4B may, as illustrated, include a plurality of colored reference elements of differing shades; the number of colored reference elements may be greater than the number of reagent pads on the examined dipstick; the colorized surface may include a plurality of groups of colored reference elements in differing shades of a same color (e.g., 470E and 470F); the colorized surface may include at least two colored reference elements of differing shades of a same color located adjacent each other and on a same side of a reagent examination region (e.g., 470E1 and 470E2); and the colorized surface may include at least two colored reference elements of a same shade of a same color located on an opposing sides of a reagent examination region (e.g., 470E1 and 470F1). Alternatively, these particular illustrated details may vary across embodiments, so long as the described functionality is achieved.

Figure 5B:
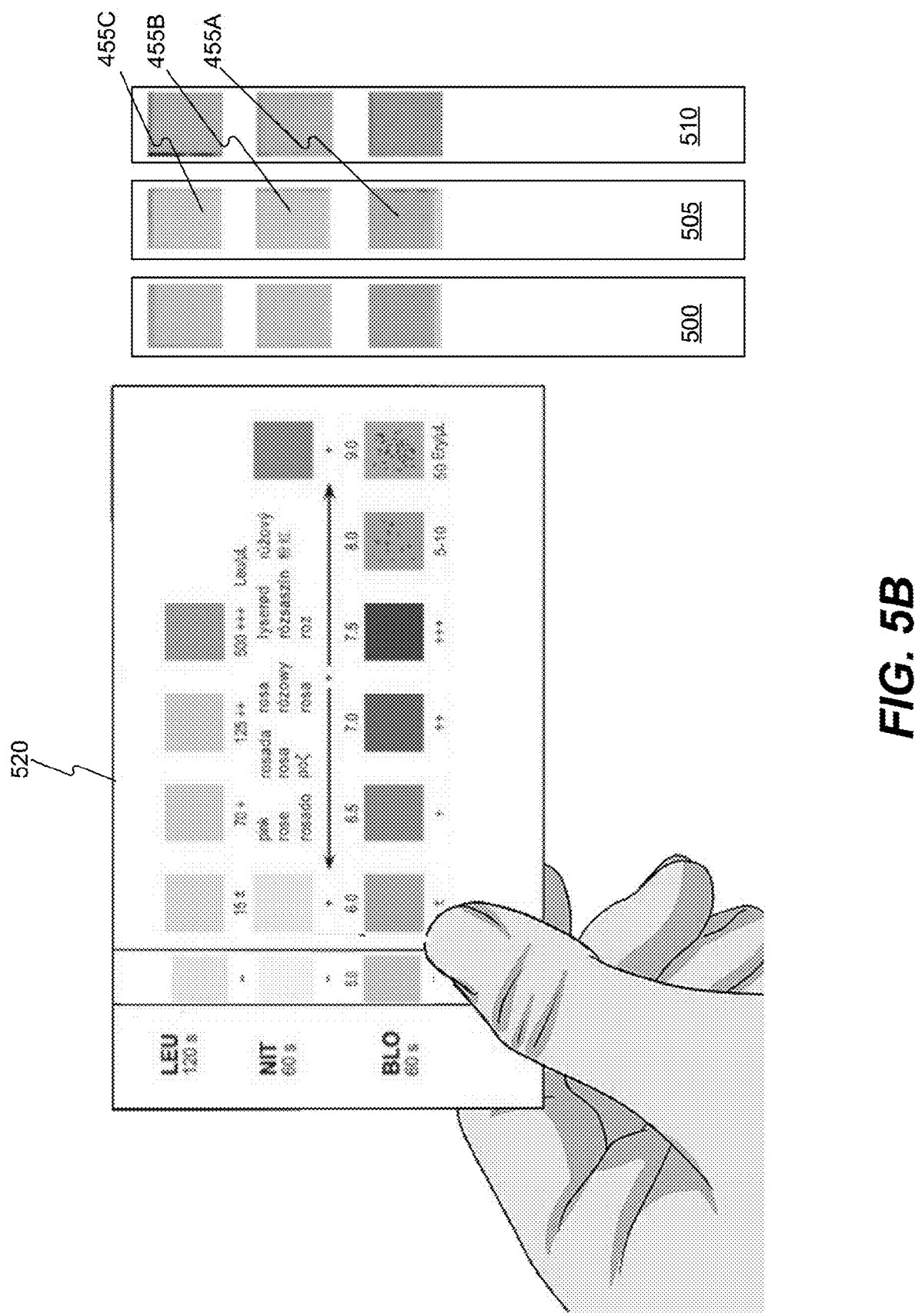
FIG. 5B is an illustration of a color mapping chart associated with the reagent shown in FIG. 5A.

FIG. 5B depicts color mapping chart 520 next to the reagent test strip pads 500, 505, and 510 depicted as they might appear in differing lighting conditions. As mentioned above, UTI dipsticks may include three reagent pads (indicated as 455A, 455B, and 455C on reagent test strip 505). In other examples, UTI dipsticks may include less or more reagent pads. In this example, first reagent pad 455A may be used to measure blood in the urine based on the pseudoperoxidase activity of hemoglobin, which catalyzes the reaction of 3,3',5,5'-Tetramethylbenzidine with buffered organic hydroperoxide. The resulting color of first reagent pad 455A should range from greenish-yellow to greenish-blue and then to dark blue. Second reagent pad 455B may be used to measure Nitrite in the urine based on the reaction of the p-arsanilic acid and nitrite, derived from a dietary nitrate in the presence of bacteria in the urine to form a diazonium compound. The diazonium compound reacts with N-(1-naphthyl)-ethylenediamine in an acidic medium. The resulting color of second reagent pad 455B should be pink. Third reagent pad 455C may be used to detect Leukocytes (white blood cells) by revealing the presence of granulocyte esterases. The esterases cleave a derivatized pyrazole amino acid ester to liberate derivatized hydroxy pyrazole. This pyrazole then reacts with a diazonium salt. The resulting color of third reagent pad 455C should be purple. In other examples, UTI dipsticks may further include additional reagent pads, for example for bilirubin, glucose, ketone, pH value, protein, specific gravity, urobilinogen, and so forth.

When reviewing reagent dipsticks 500, 505, and 510 with reference to color mapping chart 520 in FIG. 5B, the significance of analyzing results irrespective of local illumination conditions may be understood. For example, any degree of pink color in second reagent pad 455B is considered positive and typically means that the user has a urinary tract bacterial infection. If system 100 was unable to correct for distortions based on lighting conditions, the colors of second reagent pad 455B, for example would provide an indication of no UTI, when, in fact, as reflected on dip stick 500, a UTI exists.

Figure 6:
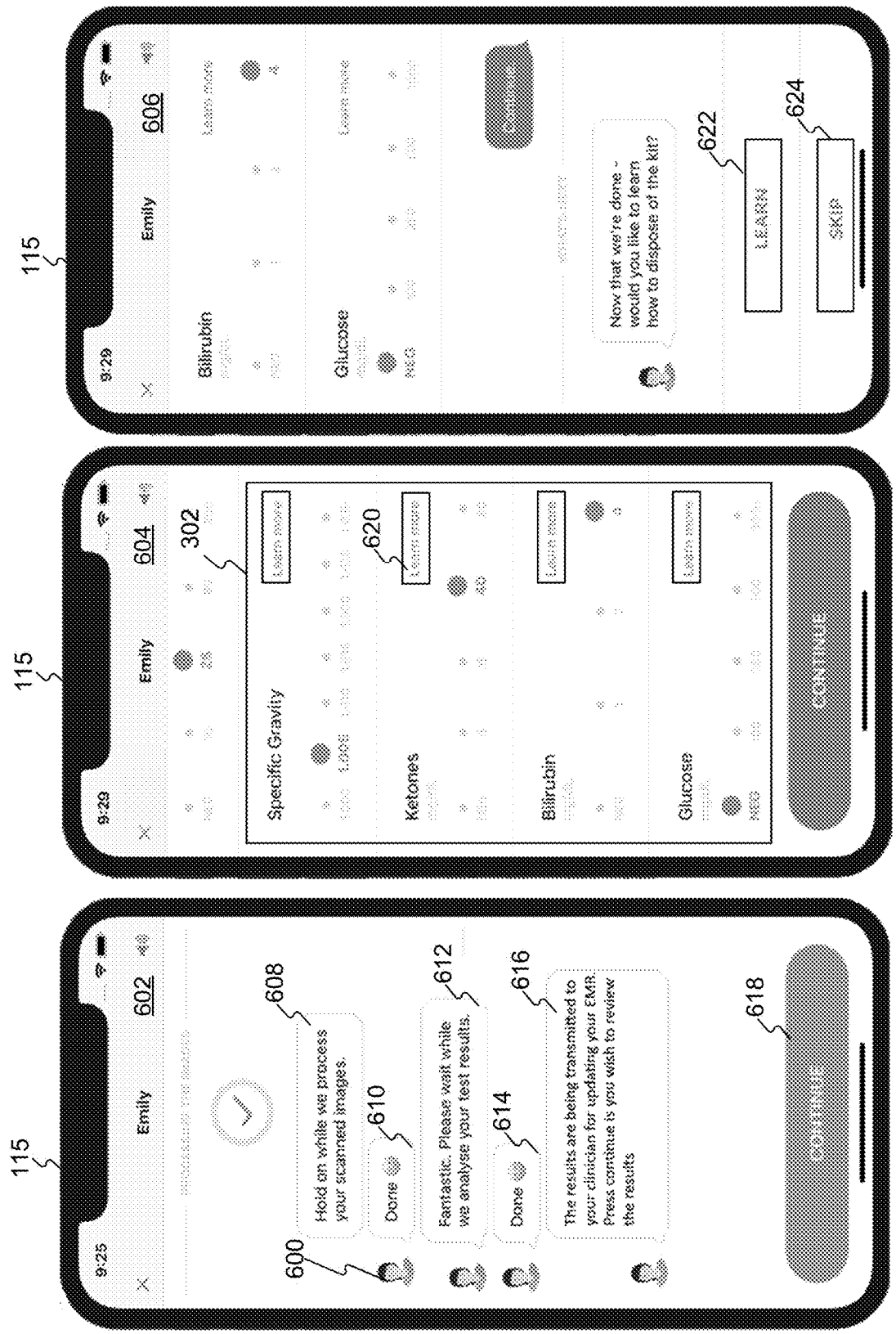
FIG. 6 depicts three screenshots illustrating an exemplary graphical user interface (GUI) for guiding a user through a medical testing process, in accordance with embodiments of the present disclosure.

FIG. 6 depicts three screenshots illustrating a graphical user interface (GUI) for guiding user 110 (FIG. 1A) through an exemplary process of medical testing. The screenshots are associated with a non-limiting example of an interactive guidance application and may be displayed on mobile communications device 115. The illustrated interactive guidance application may be designed to appear as a conversation with a chatbot 600. In one embodiment, the behavior of chatbot 600 may be defined by a determined experience level of user 110 (e.g., first time user or a returned user). For example, during a conversation with user 110, an interpretation engine on the chatbot server (e.g., server 145) may determine the experience level of user 110 and navigate the conversation data structure to fit the user's experience level (e.g., more steps provided for first time users). Alternatively, system 100 may determine the experience level of user 110 by retrieving information from a database. Screenshots 602, 604, and 606 illustrate a conversation with a user that received a home testing kit.

Screenshot 602 depicts how the interactive guidance application may provide one or more messages indicative of the progress of the testing, by for example, providing messages 608-614. Screenshot 602 also depicts how chatbot 600 may provide user 110 with an indication that the testing of the dipstick is complete, for example through message 614 or message 616. Consistent with some embodiments of the present disclosure, the test results may be automatically transmitted to healthcare provider 160 (e.g., as indicated in message 616). User 110 may interact with chatbot 600 through an input device (e.g., a keyboard, a touch screen, or microphone). For example, interactive guidance application includes a "continue" button 618 for receiving feedback from user 110.

Screenshot 604 depicts how the interactive guidance application may provide user 110 data based on the determined extent of the chemical reaction on the reagent pads of the examined dipstick. For example, interactive guidance application may present to user 110 test results 302. In one example, each section in test results 302 may correspond with a reagent pad on the examined dipstick. In another example, a section in test results 302 may correspond to a result based on two or more reagent pads. In one embodiment, next to each section, interactive guidance application may present a "learn more" button 620. Upon selection of the "learn more" button 620, interactive guidance application may provide additional information on the medical meaning of the test results. Screenshot 606 depicts chatbot 600 asking user 110 if he/she would like to learn how to dispose of the home kit. User 110 may answer by selecting the "learn" button 622 or the "skip" button 624. In addition, chatbot 600 may provide a notification (not shown) that includes an instruction to recapture an image of the dipstick, for example after determining that the dipstick was improperly placed in dipstick placement region 460. Also, in response to a determination that local illumination conditions are insufficient for completing the image analysis, chatbot 600 may also instruct user 110 to change at least one illumination aspect and recapture an image of the dipstick.

Figure 7:
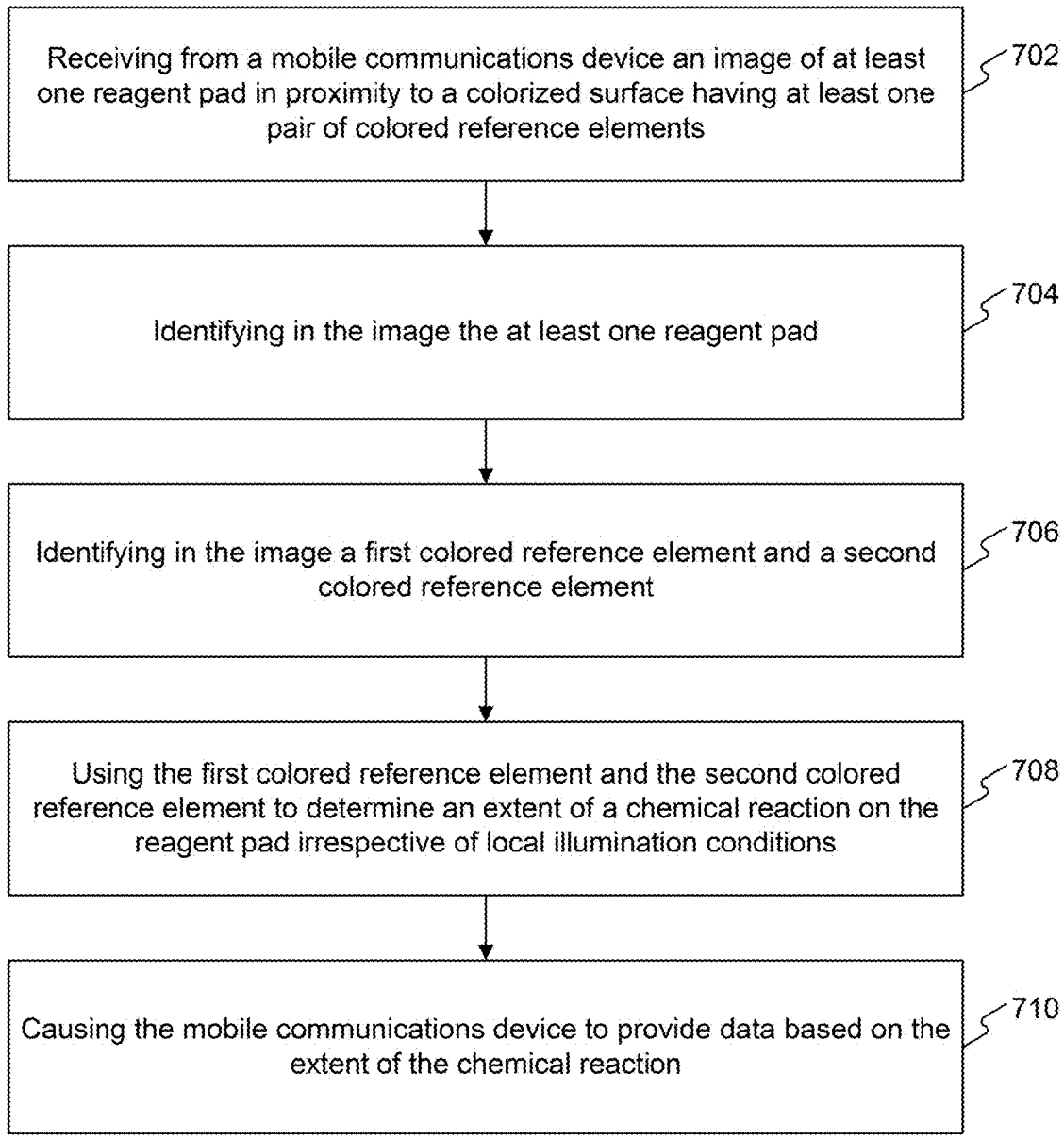
FIG. 7 is a flowchart of an exemplary process for analyzing visible chemical reactions, in accordance with some embodiments of the present disclosure.

FIG. 7 is a flowchart of an example method 700 for analyzing visible chemical reactions executed by a processing device of system 100, according to embodiments of the present disclosure. The processing device of system 100 may include a processor within a mobile communications device (e.g., mobile communications devices 115 and 125) or a processor within a server (e.g., server 145) remote from the mobile communications device. For purposes of illustration, in the following description reference is made to certain components of system 100. It will be appreciated, however, that other implementations are possible and that any combination of components or devices may be utilized to implement the exemplary method. It will also be readily appreciated that the illustrated method can be altered to modify the order of steps, delete steps, or further include additional steps.

Disclosed embodiments may include receiving from an image sensor associated with a mobile communications device an image of a reagent pad in proximity to a colorized surface having at least one pair of colored reference elements designed to be used together to determine an extent of a reaction on the reagent pad. As discussed earlier, various types of image sensors/mobile communications devices may be used capture various forms of color references elements adjacent a reagent pad. By way of example only, at step 702 in FIG. 7, a processing device (e.g., processing device 202) may receive from a mobile communications device image data depicting at least one reagent pad in proximity to a colorized surface. The at least one reagent pad (e.g., reagent pad 455) may include a plurality of reagent pads located on a dipstick (e.g., dipstick 450). The at least one reagent pad may be used for urinalysis, or any other test indicated by a color reagent reaction. The colorized surface may have at least one pair of colored reference elements designed to be used together to determine the extent of a reaction on the at least one reagent pad. Consistent with the present disclosure, the image data includes an image (e.g., image 130) captured by an image sensor (e.g., image sensor 226) associated with a mobile communications device (e.g., mobile communications device 115).

Disclosed embodiments may include identifying in an image a reagent pad. This may be achieved by many alternative forms of image analysis, where the reagent pad is located within a broader image. For example, at step 704, the processing device may identify in the image the at least one reagent pad. In one example, an object detection algorithm may be used to detect the dipstick in the image, and the reagent pads may be identified based on their positions on the dipstick. In another example, a machine learning model may be trained using training examples to identify reagent pads in images, and the trained machine learning model may be used to analyze the image and identify the reagent pad. In some embodiments, the processing device may also identify in the image a plurality of position markers (e.g., high contrast elements 475) distinguished from the at least one pair of colored reference elements (e.g., colored reference elements 470). According to an embodiment, among the plurality of position markers, at least one position marker includes a color that differs from a color of two or more other position markers. In the examples illustrated in FIG. 4B, position marker 474 has a color scheme that includes a black outer hexagon surrounding a white hexagon, which itself surrounds a red inner hexagon. In contrast, marker 475 replaces the red inner hexagon with a black inner hexagon. After identifying the plurality of position markers, the processing device may analyze the image using the plurality of position markers to determine that an orientation of the at least one reagent pad is an undesired orientation; for example, the dipstick may be placed upside down on dipstick placement region 460. In response to the determination that the orientation of the at least one reagent pad is at an undesired orientation, the processing device may provide a notification to a user. The notification may include an instruction to recapture an image of the dipstick and/or a suggestion on how to reposition the orientation of the at least one reagent pad.

Disclosed embodiments may include identifying in the image a first colored reference element and identifying in the image a second colored reference element. This identification may occur through any type of image analysis, and the reference elements may be shaped, colored, and located according to a designer's preference. In one example, an object detection algorithm may be used to detect the color board in the image, and the color reference elements may be identified based on their positions on the color board. In another example, pattern recognition algorithms may be used to detect known patterns on a color board (such as position markers 474 and 475), and the color reference elements may be identified based on their relative positions to the detected patterns. In yet another example, a machine learning model may be trained using training examples to identify color reference elements in images, and the trained machine learning model may be used to analyze the image and identify the color reference elements. By way of example only, at step 706, the processing device may identify in the image a first colored reference element and a second colored reference element. In one embodiment, the first and the second colored reference elements of the at least one pair are arranged in the image on opposing sides of the colorized surface.

A colorized surface consistent with one embodiment of the present disclosure may include at least ten pairs of colored reference elements. Identifying in the image the first colored reference element and the second colored reference element may also include identifying in a captured image, differences between the first colored reference element and the second colored reference element. Although the first and the second colored reference elements may have been printed with the same color and the same shade, local illumination conditions may cause depictions of the first colored reference element and the second colored reference element to differ in color and/or shade in the captured image. Consistent with the present disclosure, the known colors of the at least one pair of colored reference elements may be compared with the perceived colors in the captured image, to determine the effects of local illumination conditions and/or the effects of image capturing settings on the at least one reagent. For example, when members of the at least one pair of colored reference elements are arranged on opposing sides of the colorized surface, the system may determine which side is closer to a light source and use the visual changes between members of a pair of colored reference elements to calculate a correction factor for correcting the color of the at least reagent pad.

Disclosed embodiments may include using the first colored reference element and the second colored reference element to determine an extent of a chemical reaction on the reagent pad irrespective of local illumination conditions. As described earlier, the reference elements may be used to correct for local illumination conditions, for the relative position of the colored reference element with respect to the image sensor, and/or for the image sensor settings. By way of example only, at step 708, the processing device may use the first colored reference element and the second colored reference element to determine an extent of a chemical reaction on the reagent pad irrespective of local illumination conditions, irrespective of the relative position of the colored reference element with respect to the image sensor, and/or irrespective of effects of image capturing settings. In one embodiment, the processing device may identify illumination parameters indicative of the local illumination conditions based on the at least one pair of colored reference elements. Examples of illumination parameters may include the type of illumination source (such as sunlight, LED, neon, incandescent light bulbs, etc.), the frequency of illumination source (for example, of a neon), the location of illumination source, the number of illumination sources, and other parameters that may affect the local illumination conditions. For example, a machine learning model may be trained using training example to identify illumination parameters from images of color boards, and the trained machine learning model may be used to analyze an image of a color board to identify the illumination parameters. An example of such training example may include an image of a color board captured under particular illumination parameters, together with an indication of the illumination parameters. Thereafter, the processing device may determine the extent of the chemical reaction on the reagent pad irrespective of local illumination conditions based on the identified illumination parameters. In other words, by correcting for the local illumination conditions, the processing device may determine the extent of reaction irrespective of those conditions. For example, a machine learning model may be trained using training example to determine the extent of the chemical reaction on reagent pads from images of reagent pads and illumination parameters, and the trained machine learning model may be used to analyze an image of a reagent pad using identified illumination parameters (for example using the illumination parameters identified as described above) to determine the extent of the chemical reaction on the reagent pad irrespective of local illumination conditions. An example of such training example may include an image of a reagent pad with corresponding illumination parameters, together with the desired extent of the chemical reaction on the reagent pad to be determined. In another embodiment, the processing device may determine image capturing parameters indicative of the effects of the image capturing settings, based on the at least one pair of colored reference elements. In other words, since cameras or models of cameras may perceive a scene differently based on preset or user-selected settings, the processing device may correct for those settings and thereafter determine the extent of a reaction irrespective of those settings.

Additionally, the processing device may calculate a normalized reagent test color based on the first colored reference element and the second colored reference element. Calculating the normalized reagent test color may include rectifying the colors of the at least one reagent pad to remove effects of local illumination, to remove effects of the relative position of the colored reference element with respect to the image sensor, and/or to remove effects of image capturing settings. In one example, a machine learning model may be trained using training examples to calculate normalized reagent test colors from the color of the reagent pads and colors of reference elements in captured images. The trained machine learning model may be used to calculate the normalized reagent test color from the color of the reagent pad, the color of the first colored reference element, and the color of the second colored reference element in an image. An example of such training example may include a triplet of the color of the reagent pad, the color of the first colored reference element, and the color of the second colored reference element in an image, together with the desired normalized reagent test color to be determined. When the at least one reagent pad includes a plurality of reagent pads, the processing device may use the normalized reagent test color associated with a first reagent pad to determine the normalized reagent test color of a second reagent pad. Thereafter, the processing device may determine the extent of the chemical reaction on the at least one reagent pad irrespective of local illumination conditions based on the normalized reagent test color. In some cases, when the at least one reagent pad includes a plurality of reagent pads, the processing device may use one or more normalized reagent test colors to determine a uniform color for pixels associated with each of the depiction of plurality of reagent pads. Thereafter, the processing device may determine the extent of the chemical reaction on each of the plurality of reagent pads based on the uniform color associated with each of the plurality of reagent pads.

Disclosed embodiments may include causing the mobile communications device to provide data based on the extent of the chemical reaction. The data which may be provided to either the user and/or transmitted to another over a network, may include either a test result, an indicator of a test result, or an instruction related to the extent of a chemical reaction. By way of example only, at step 710, the processing device may cause the mobile communications device to provide data based on the extent of the chemical reaction. The data provided based on the extent of the chemical reaction may include medical data associated with a plurality of differing urinary properties. For example, the medical data may include the test results (e.g., test results 302), which may include a conclusion (e.g., positive for UTI) or some indicator from which test results may be derived (e.g., a value). Alternatively, the data provided based on the extent of the chemical reaction may include an indication to contact the user's physician. In one embodiment, causing the mobile communications device to provide the data may include causing the mobile communications device to transmit the data to a medical entity associated with a user of the mobile communications device. For example, the medical entity associated with a user may be the user's doctor. In another embodiment, causing the mobile communications device to provide the data may include causing the mobile communications device to display the data on a screen associated with the mobile communications device.

Figure 8:
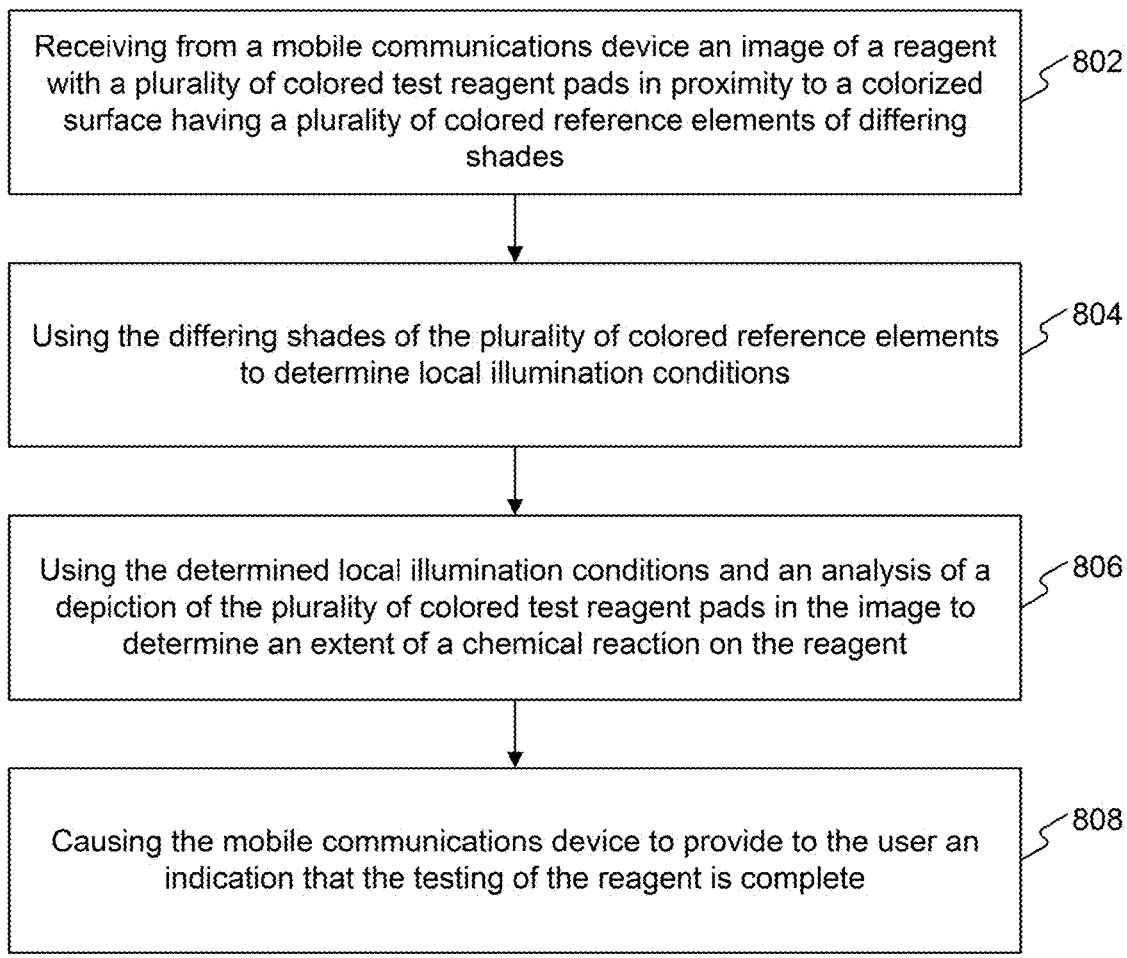
FIG. 8 is a flowchart of an exemplary process for testing visible chemical reactions of a reagent, in accordance with some embodiments of the present disclosure.

FIG. 8 is a flowchart of another exemplary method 800 for testing visible chemical reactions of a reagent pad that may be executed, for example, by a processing device of system 100, according to embodiments of the present disclosure. The processing device of system 100 may be a processor within a mobile communications device (e.g., mobile communications devices 115 and 125) or a processor within a server (e.g., server 145) remote from the mobile communications device. For purposes of illustration, in the following description reference is made to certain components of system 100. It will be appreciated, however, that other implementations are possible and that any combination of components or devices may be utilized to implement the exemplary method. It will also be readily appreciated that the illustrated method can be altered to modify the order of steps, delete steps, or further include additional steps.

At step 802, a processing device (e.g., processing device 202) may receive from a mobile communications device an image of a reagent (e.g., dipstick 450) with a plurality of colored test reagent pads (e.g., reagent pad 455) in proximity to a colorized surface (e.g., colorized surface 132). The colorized surface may have a plurality of colored reference elements (e.g., colored reference elements 470) of differing shades. Consistent with the present disclosure, the image (e.g., image 130) was captured by an image sensor (e.g., image sensor 226) associated with a mobile communications device (e.g., mobile communications devices 115).

At step 804, the processing device may use the differing shades of the plurality of colored reference elements to determine local illumination conditions and/or effects of image capturing settings. As discussed above with reference to FIG. 4B, the colorized surface may include more colored reference elements than a number of colored test element pads on the reagent. In one embodiment, the colorized surface may include at least two colored reference elements with a same color and a same shade and at least three, at least four, or at least five reference elements with differing shades of a same color. Consistent with the present disclosure, the known levels of shade of the plurality of colored reference elements may be compared with the perceived colors in a captured image to determine the effects of local illumination conditions and/or the effects of image capturing settings on the at least one reagent. For example, when the plurality of colored reference elements are arranged adjacent one to another, the system may determine a brightness map of colored reference elements to calculate a correction factor for correcting the level of shade of a depiction of at least colored test reagent pad. In one example, a machine learning model may be trained using training examples to determine correction factors for correcting levels of shade of depictions of reagent pad in images from results of comparisons of the known levels and measured levels of shades of reference elements in the images. The trained machine learning model may be used to analyze the comparison of the known and measured level of shades of reference elements in an image to determine the correction factor for correcting a level of shade of a depiction of a reagent pad in the image. An example of such training example may include a result of a comparison of the known levels and measured levels of shades of reference elements in an image, together with the desired correction factor to be determined. Further, in some examples, the system may use the calculated correction factor to correct the level of shade of a depiction of at least colored test reagent pad, for example by multiplying one or more color components of one or more pixels of the depiction of the reagent pad by the correction factor, by multiplying one or more color components of a representative color of the depiction of the reagent pad by the correction factor, by adding the correction factor to one or more color components of one or more pixels of the depiction of the reagent pad, by adding the correction factor to one or more color components of a representative color of the depiction of the reagent pad, and so forth. In some embodiments, in response to first determined local illumination conditions, the processing device may instruct the user to change at least one illumination aspect and recapture an image of the of the reagent. For example, the processing device may indicate that local illumination conditions are too dark for completing the test. However, in response to second determined local illumination conditions, the processing device may forgo instructing the user to change the at least one illumination aspect.

At step 806, the processing device may use the determined local illumination conditions and/or the determined effects of the image capturing settings together with an analysis of a depiction of the plurality of colored test reagent pads in the image to determine an extent of a chemical reaction on the reagent. Consistent with the present disclosure, determining the extent of a chemical reaction may include color calibration of the plurality of colored test reagent pads in the image based on the local illumination conditions and/or the determined effects of the image capturing settings. In one example, color calibration may include rectifying the received image by changing colors of pixels associated with a least one colored test element of the reagent pad based on the determined local illumination conditions and/or the determined effects of the image capturing settings. By way of example, in response to a first set of determined local illumination conditions and a first depiction of the plurality of colored test reagent pads in the image, the processing device may determine a first extent of the chemical reaction on the reagent; and in response to a second set of determined local illumination conditions and the first depiction of the plurality of colored test reagent pads in the image, the processing device may determine a second extent of the chemical reaction on the reagent. The second extent of the chemical reaction may differ from the first extent of the chemical reaction. In another example, in response to a first set of determined effects of the image capturing settings on the image, the processing device may determine a first extent of the chemical reaction on the reagent; and in response to a second set of determined effects of the image capturing settings on the image, the processing device may determine a second extent of the chemical reaction on the reagent. The second extent of the chemical reaction may differ from the first extent of the chemical reaction.

In some embodiments, the processing device may generate a set of correction factors based on the determined local illumination conditions and/or the determined effects of the image capturing settings. The set of correction factors may include a specific correction factor for each of the plurality of colored test reagent pads or a general correction factor for all of the plurality of colored test reagent pads. The set of correction factors may include a combination of correction factors associated with the determined local illumination conditions and correction factors associated with the determined effects of the image capturing settings. The processing device may use the set of correction factors and an analysis of a depiction of the plurality of colored test reagent pads in the image to determine an extent of a chemical reaction on the reagent irrespective of local illumination conditions and irrespective of effects of the image capturing settings. In one example, the colors of the reference elements depicted in the image and the known colors of the reference elements may be used to determine the correction factors, for example using any color calibration algorithm. For example, such correction factor may include sensor response curves of the camera used to capture the image for different colors, and the sensor response curves may be used to determine the actual color of a reagent pad from the color of the reagent pad depicted in the image.

At step 808, the processing device may cause the mobile communications device to provide to the user an indication that the testing of the reagent is complete. In one embodiment, providing the user with an indication that the testing of the reagent is complete includes providing data indicative of the extent of the chemical reaction. Additionally or alternatively, providing the user with an indication that the testing of the reagent is complete includes providing a message indicative of progress of the testing. Consistent with the present disclosure, the processing device may determine that the reagent is improperly placed in the region for placement of the reagent (e.g., dipstick placement region 460) and provide an associated notification to a user. In some cases, the notification may include an instruction to recapture an image of the reagent within a time period, e.g., within two minutes.

Figure 9:
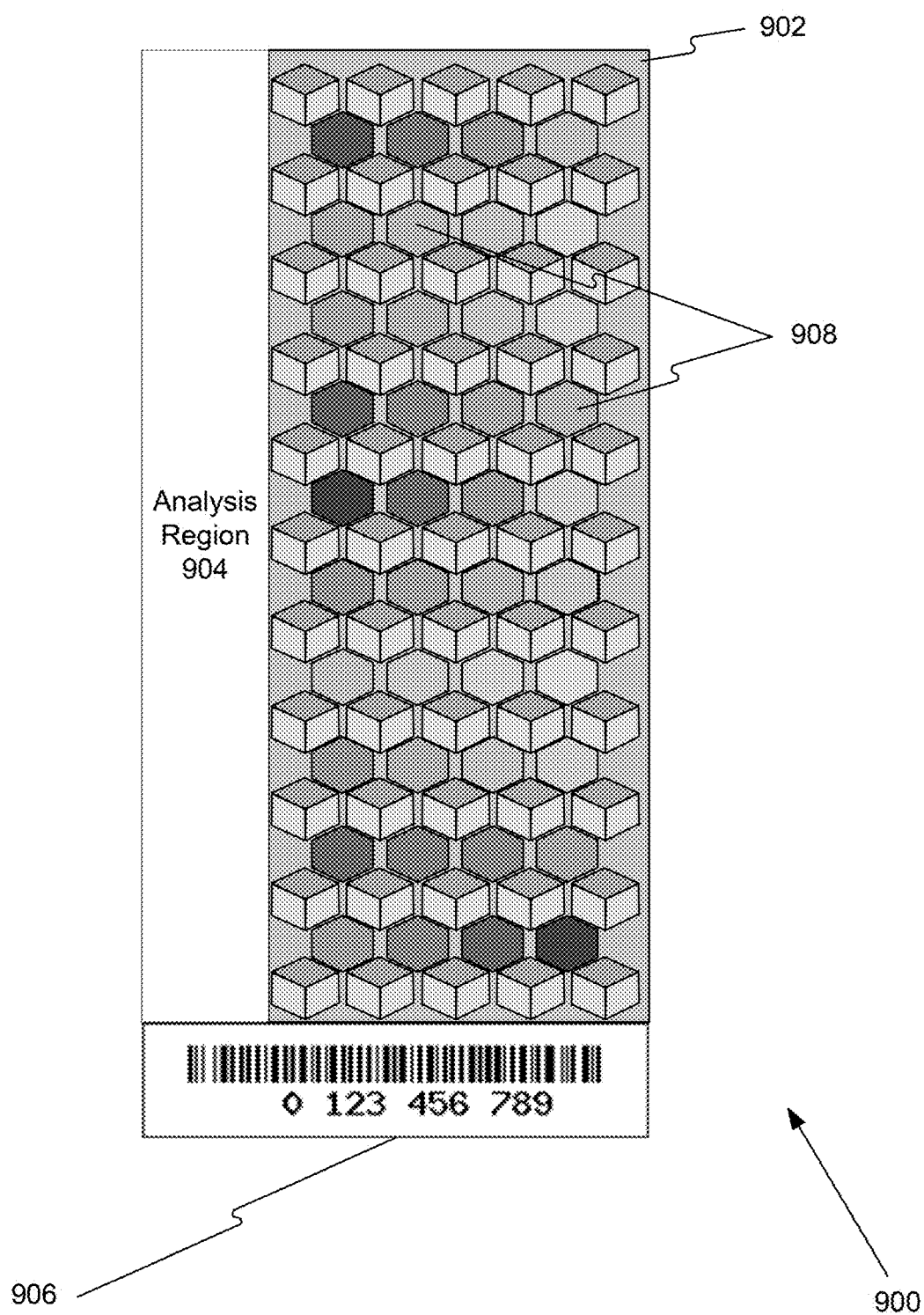
FIG. 9 is an illustration of a color board, consistent with the present disclosure.

FIG. 9 depicts an exemplary color board 900, which may be used in reagent strip testing. Color board 900 may be, for example, a surface that displays various colors, areas, symbols, patterns, etc. Such a surface may be made of any combination of suitable materials for displaying colors, including but without limitation, paper, cardboard, plastic, cloth, wood, and/or fibers. Color board 900 may include a colorized surface 902, having a number of reference elements thereon. Some of these reference elements may be colored, such as colored reference elements 908, which may be a part of a group of colored reference elements, such as 470A and/or 470B, discussed with respect to FIG. 4B. In some embodiments, multiple color reference elements 908 may share substantially the same color and/or hue. For example, one color reference element 908 may have a similar hue but a different chroma value relative to another color reference element 908. As another example, one color reference element 908 may have a similar hue but a different chroma value relative to another color reference element 908. Color elements sharing substantially the same color may be adjacent to each other on color board 900 (e.g., on the same row within colorized surface 902). Other reference elements may be cube-like grey elements, which may be used for color correction, among other purposes. These grey elements may be the same as or similar to the grey elements discussed with respect to FIG. 4B.

FIG. 9 provides but one example. The number and arrangement of elements on a color board can be configured in any number of ways. For example, while color board 900 presents an analysis region 104 on one side of all reference elements, the color board could be constructed with reference elements on both sides of the analysis region 904, or even above and/or below analysis region 904. As another example, color board 900 may include an analysis region 904 shaped similarly to the shape of a test object, which may be surrounded by a colorized surface 902. Color board 900 may also have multiple analysis regions or multiple unique codes 906, which may enable a machine to read information associated with different data.

In some embodiments, analysis region 904 may be configured to receive a reagent pad. For example, analysis region 904 may be similar in size to a reagent pad and/or may include a printed outline of a reagent pad (e.g., to guide placement of the reagent pad within analysis region 904). Analysis region 904 may also be made of a combination of materials suited to receive a reagent pad. For example, analysis region 904 may comprise materials for holding or guiding a reagent pad, such as plastic (e.g., plastic having snaps for securing a reagent pad to analysis region 904), statically charged material, magnets, etc. Analysis region 904 may also be configured in similar manners to receive a test object other than a reagent pad, such as a dipstick, liquid, photograph (e.g., of a wound), part of a human body (e.g., a portion of wounded skin), and/or any object presented for analysis with color board 900. In some embodiments, analysis region 904 may be transparent or may be negative space, in order to appropriately accommodate a test object (e.g., part of a human body).

Disclosed embodiments may include a unique code on the color board, the code reflecting specific chromatic properties associated with each of the first colored element and the second colored element at the time of printing, and wherein the code is machine readable to enable a machine to later normalize a comparison color, for determining chromatic properties of the at least one reagent pad. The unique code may include one or more of numbers, an alphanumeric characters, a barcode, a QR code, a visual pattern, a pattern of punches, a pattern of embossing, a non-visual machine readable indicator such as an electronic tag, (Near Field, RFID) and/or any unique visual indicator. Such a code is unique in that it is correlated to the specific colors on the color board with which it is associated. If many color boards are printed with precisely the same colors, multiple boards may share a common unique code. The unique code may also be unique to any combination of the color board, a geographical region, a production line, a creator of the color board, a health care provider, a type of desired medical test and/or any of the items discussed in the examples below.

By way of example only, color board 900 in FIG. 9, may include a unique code 906. In some embodiments, unique code 906 may reflect specific chromatic properties associated with any number of colored reference elements 908 at the time of a printing of color board 900 and/or colorized surface 902. In some embodiments, these chromatic properties may include variations in colors of any number of colored reference elements 908. For example, a chromatic property may be a variation in the hue of a colored reference element 908. Variations in color may be expressed relative to another colored reference element 908, or relative to a reference that is not on color board 900. In some embodiments, unique code 906 may appear on a test object (e.g., a dipstick) rather than on color board 900.

Unique code 906 may be machine readable to enable a machine to normalize a comparison color. Unique code 906 may include any combination of a number, an alphanumeric sequence, a barcode, a QR code, a unique visual pattern, a unique pattern of punches, a unique pattern of embossing, and/or any unique visual indicator. In some embodiments, unique code 906 may be unique to any combination of the color board, a geographical region, a production line, a creator of the color board, a health care provider, a type of desired medical test (urinalysis to determine pregnancy, urinalysis to determine a bladder infection, a spit test to determine a mouth infection, etc.), attributes of a user of the color board 900, specific chromatic properties, a range of chromatic properties, and the like. In some embodiments, unique code 906 may be configured to enable a machine to determine a detail regarding a testing kit with which color board 900 is associated. In some embodiments, such a detail may be used during the execution of testing of a reagent pad (e.g., a reagent pad analyzed using color reference elements 908). For example, such a detail may include a geographical region, a health maintenance organization (HMO), a service provider, an identification of a doctor, an identification of a patient, and/or doctor order information. Based on any combination of details, including a single detail, analysis results may be tailored to include or exclude specific information (e.g., doctor order information may indicate that a particular analysis should be performed on a reagent pad).

Unique code 906 may also be configured to enable a machine to determine information related to a previous use of color board 900. Such previous use information may include how many times color board 900 was previously used, when a previous use of color board 900 took place, a type of use, a type of analysis provided, etc. For example, a machine may read unique code 906 and determine, based on stored data (e.g., stored in a database), that a machine previously read unique code 906 and/or that analysis related to color board 900 was provided (e.g., based on a previously received image of color board 900). This previous use information may be used to determine if color board 900 was used more than a particular number of times (e.g., three times), or if color board 900 was used outside a particular time window (e.g., whether color board 900 was used within a week of a first use).

Chromatic properties may include, but are not limited to, red-blue-green values, saturation, contrast, tint, shade, hue, value, and/or chroma. Chromatic properties may also be expressed a difference between chromatic properties of different elements (e.g., a reagent pad and colored reference elements 908). In some embodiments, chromatic properties may be discernable from unique code 906 itself (i.e., unique code 906 indicates parameterized values of chromatic properties). In some embodiments, chromatic properties may be determined by comparing unique code 906 to data stored in a data structure, either in addition to or as an alternative to being discernable from unique code 906 itself. For example, unique code 906 may include a unique identification number (e.g., an alphanumeric sequence) that corresponds to data including chromatic properties (e.g., chromatic properties associated with a color board 900 of unique code 906).

Figure 10:
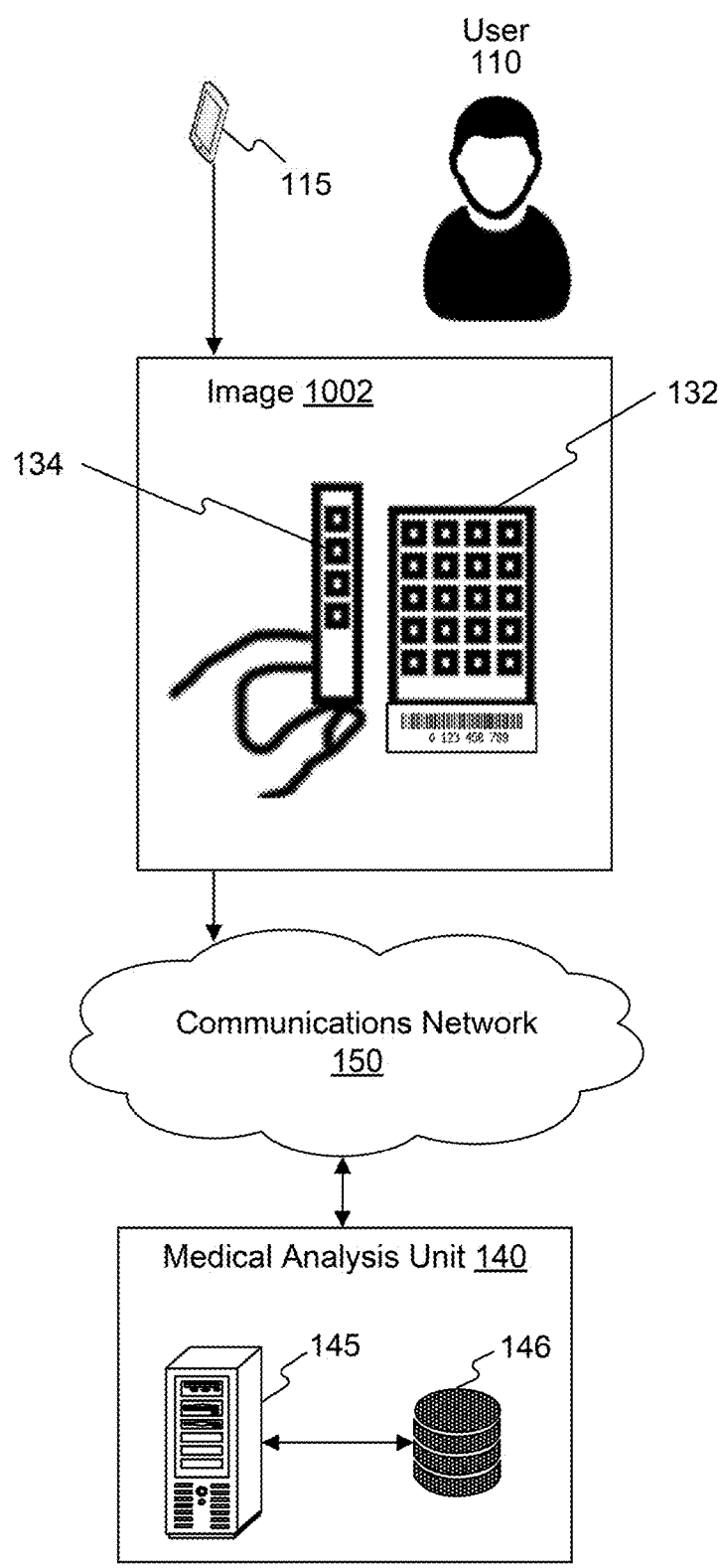
FIG. 10 is a schematic illustration of a color analysis system, consistent with the present disclosure.

FIG. 10 schematically depicts a color analysis system 1000, which may include elements of system 100. In some embodiments, color analysis system 1000 may include a mobile communications device 115 that may communicate with communications network 150, such as by sending image 1002 to communications network 150. Mobile communications device 115 may be operated by a user 110. User 110 may send image 1002 from mobile communications device 115 to communications network 150.

Image 1002 may include a colorized surface 132 (which may be a color board 900 or a portion thereof), and/or an object to be examined 134 (i.e., a test object). In some embodiments, image 1002 may have been captured using an image capturing component of mobile communications device 115. In other embodiments, image 1002 may be captured and/or sent by a device other than mobile communications device 115, such as a desktop computer, special purpose computer, or other computing device. A device that captures or sends image 1002 may be associated with a user 110, a medical caregiver, or entity (e.g., an urgent care center, doctor's office).

Images 1002 received at communications network 150 may be forwarded to a medical analysis unit 140, which may include a server 145 coupled to one or more physical or virtual storage devices such as a database 146. Server 145 and/or database 146 may contain programs, rules, applications, instructions, etc. used to process image 1002 and perform medical analysis on information obtained from image 1002. For example, medical analysis unit 140 may carry out process 1100, described with respect to FIG. 11 below. Although medical analysis unit is illustrated in FIG. 10 as a box including multiple components, all components do not need to reside in the same location.

Figure 11:
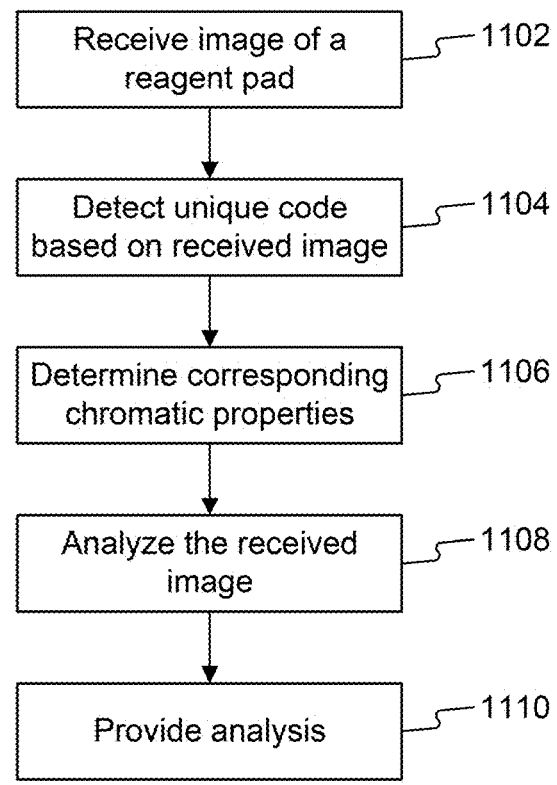
FIG. 11 is a flowchart of a process for analyzing colors, consistent with the present disclosure.

FIG. 11 is a flowchart of an example method 1100 for analyzing colors, executed by a processing device of system 100, such as mobile communications device 115, mobile communications device 125, server 145 (i.e., remote from mobile communications device 115), or communications device 165, according to embodiments of the present disclosure. For purposes of illustration, in the following description, reference is made to certain components of system 100. It will be appreciated, however, that other implementations are possible and that other components may be utilized to implement the exemplary method (including a portion of the exemplary method). It will also be readily appreciated that the illustrated method can be altered to modify the order of steps, delete steps, or further include additional steps. While the steps described below reference certain illustrated structures, it is to be understood that the steps are not limited to any particular structure.

Disclosed embodiments may include receiving from an image sensor associated with a mobile communications device an image of a reagent pad in proximity to a color board having a first colored reference, a second colored reference, a test region on the color board surface configured to receive at least one reagent pad, and a unique code. The receipt may occur within the mobile communications device itself, or remote from the mobile communications device, via a network data transfer. Many examples of mobile communications devices, reagent pads, images, color boards, colored references and unique codes are described herein, and are all intended to be incorporated within this step of receiving an image of a reagent pad.

By way of example, at step 1102, a processing device (e.g., a processing device 202 of a medical analysis unit 140) may receive an image of a reagent pad. In some embodiments, the reagent pad may have been used (for example, liquid, such as urine, may have been deposited on the reagent pad so that a chemical reaction may take place). In some embodiments, the processing device may receive an image of a dipstick (e.g., a dipstick used in place of reagent pad), color board 900, and/or a test object.

At step 1104, the processing device may detect a unique code based on the received image. For example, the processing device may detect that a color board 900 may be in the image, and may detect a unique code 906 on part of the color board 900. In some embodiments, the unique code itself may be visible in the image (e.g., an alphanumeric sequence). In some embodiments, the unique code may not visible from the image itself but may be obtained by the processing device reading information from the image or using a tag sensor associated with the mobile communications device. For example, the processing device may read a QR code from the image, and the QR code may be linked to a unique code (e.g., the QR code may point to a unique code stored in a database, which the processing device may query to receive the unique code).

Disclosed embodiments may also include determining from the unique code specific chromatic properties associated with each of the first colored element and the second colored element. Determining the specific chromatic properties may occur in any one of many ways, including, for example performing a look up in a table or a data structure, which correlates the code with chromatic properties. Alternatively, the code itself may encode the specific chromatic properties.

By way of example, at step 1106, a processing device may determine chromatic properties corresponding to the unique code detected at step 1104. The chromatic properties corresponding to the unique code may be associated with a colorized surface 902, which may be part of the same color board 900 as the detected unique code (or a visual indicator of the unique code). For example, the determined chromatic properties may include hue, value, and/or chroma information for reference elements of a colorized surface 902. These chromatic properties may have been established at a time when the color board 900 or colorized surface 902 was printed, shortly after printing, or a priori. In some embodiments, different sets of chromatic properties may be determined based on the unique code, which may be associated with different reference elements.

In some embodiments, at step 1106, information other than chromatic properties may be determined from the unique code, which may occur before, after, or while determining the chromatic information. This other information may be related to a previous use of a color board 900 (i.e., a color board 900 from which the unique code is read). Such previous use information may include how many times color board 900 was previously used, when a previous use of color board 900 took place, a type of use, a type of analysis provided, etc. For example, a processing device performing process 1100 may read unique code 906 and determine, based on stored data, that a processing device previously read unique code 906 and/or that a type of analysis related to color board 900 was provided (e.g., based on a previously received image of color board 900 having a test object in analysis region 904). In some examples, a color correction function tuned to the particular color board may be obtained based on the unique code. Further, in one example, this color correction function tuned to the particular color board may be used to analyze the image and correct colors in images, for example according to step 1108. In some examples, a color correction function tuned to the particular color board for determining the extent of a chemical reaction on a reagent pad may be obtained based on the unique code. Further, in one example, this function may be used to analyze the image and determine the extent of a chemical reaction on a reagent pad, for example according to step 1108.

The previous use information may be used to determine if color board 900 was used more than a threshold number of times (e.g., three times) and/or if color board 900 was used outside a particular time window (whether color board 900 was used within a week of a first use, whether color board 900 was used within a number of months after its production, etc.). The threshold number of times or particular time window may be based on the unique code, a type of a past usage of the color board 900, patient information, etc. In some embodiments, the threshold number of times or particular time window may be selected by a manufacturer of the color board, a medical provider, a doctor, and/or another entity associated with the color board 900. In some embodiments, a processing device performing process 1100 may proceed to determine chromatic properties, analyze a received image, or perform another part of process 1110 if it determines that a number of previous uses of the color board 900 does not exceed a threshold number of times.

If the processing device performing process 1100 determines that a number of previous uses of the color board 900 exceeds a threshold number of times, it may not perform another step, such as determining chromatic properties, analyzing a received image, returning analysis results, etc. In some embodiments, a processing device may generate a notification based on determining that the number of previous uses exceeds a threshold. For example, mobile communications device 115 may generate and display a notification to inform a user that the color board 900 may not be used again because it has already been used a threshold number of times. As another example, another device, such as server 145, may generate a notification and send it to mobile communications device 115. In some embodiments, a notification may be generated even if a use of a color board 900 does not exceed a threshold number of uses, to display information to a user (a notification of a time window remaining, a number of uses remaining, medical information related to a previous use, etc.). The same or similar actions may be performed based on whether a previous use of the color board 900 was within or outside a particular time window, rather than, or in addition to, whether a previous number of uses exceeded a threshold.

Disclosed embodiments may include using the specific chromatic properties of first colored reference element and the second colored reference element to analyze a depiction of the at least one reagent pad in the image for determining an extent of a chemical reaction on the at least one reagent pad. The specific chromatic properties of the reference elements may be used, as described earlier, to generate a correction factor or other normalization data to account for variations that might occur as the result of a local illumination condition or a camera setting.

By way of example, at step 1108, a processing device may analyze the received image. This analysis may be based on the chromatic properties determined at step 1106 and/or a part (or entirety) of the image received at step 1102. For example, the processing device may compare the determined chromatic properties to chromatic properties of a reagent pad, dipstick, and/or other test object that may be depicted in the received image. In some embodiments, the processing device may normalize a comparison color (a color reference element, a color of a test object, etc.) using the chromatic properties determined at step 1106, for example as described above in relation to methods 700 and 800. Normalizing a comparison color may include removing local illumination effects (i.e., illumination effects distorting chromatic information of reference elements), which may be accomplished in part by using grey reference elements, such as those discussed with respect to FIG. 4B. In some embodiments, normalizing a comparison color may include changing a chromatic property, which may be a chromatic property of a color reference element, a test object, etc.

As part of the analysis, processing device may use specific chromatic properties of colored reference elements to analyze a depiction of a test object (e.g., a reagent pad) in the image for determining an extent of a chemical reaction on the test object. Different sets of chromatic properties may be used to determine different extents of a chemical reaction on the test object. For example, a first set of chromatic properties determined from the unique code may be analyzed relative to a depiction of the test object to determine a first extent of a chemical reaction on the test object. Continuing with this example, a second set of chromatic properties determined from the unique code may be analyzed, in some embodiments together with a depiction of the test object, to determine a second extent of a chemical reaction on the test object, which may differ from the first extent. Any number and combination of chromatic properties may be determined and used to determine an extent of a chemical reaction on a test object.

In some embodiments, the type of analysis performed on the received image may depend on information contained in the unique code. For example, a processing device may determine from reading the unique code that particular chromatic properties, parts of a test object, and/or reference elements should be used for the analysis. As a further example of this aspect, a processing device may determine from reading the unique code that only some portions of a dipstick (i.e. a test object) depicted in an image are relevant to the analysis.

At step 1110, the processing device may provide analysis. In some embodiments, the analysis may include results of the analysis performed at step 1008. For example, the provided analysis may include the extent of a chemical reaction on a test object. In some embodiments, the provided analysis may include information derived from an extent of a chemical reaction on a test object. For example, based on an extent of a chemical reaction on a dipstick, the processing device may determine that an individual (i.e., an individual who has used the dipstick) has a specific disease, nutrient deficiency, medical condition, is healthy, etc. In some embodiments, a confidence level (e.g., 90% certainty, 'low certainty', 'high certainty', etc.) associated with the derived information may also be provided together with the provided analysis. In some embodiments, while several analysis results may have been determined at step 1008, only a subset of these may be provided at step 1110. For example, a type of medical information to be provided may be selected based on the unique code determined at step 1104, which may contain information indicating that the analysis provided should be limited or expanded based on any combination of the color board 900, a geographical region, a production line, a creator of the color board 900, a health care provider, a type of desired medical test (urinalysis to determine pregnancy, urinalysis to determine a bladder infection, a spit test to determine a mouth infection, etc.), attributes of a user of the color board 900, specific chromatic properties, a range of chromatic properties, and the like. The processing device may then provide analysis based on this selected type of medical information and based on a determined extent of a chemical reaction on the test object. Different types of medical information may be provided, either simultaneously or at different points in time. For example, one type of medical information may be provided to a user, while another type may be provided to a medical professional. As another example, one type of medical information may be provided based on a user's geographic region at one time, but at another time the user's geographic region may be different, which may prompt the providing of a second type of medical information. In yet another example, the unique code determined at step 1104 may be used to determine a geographic region of the user, one type of medical information may be provided to a user from a first geographic region, and a second type of medical information may be provided to a user from a second geographic region. In an additional example, the unique code determined at step 1104 may be used to determine a service provider (such as an insurer, a medical care provider, etc.) of the user, one type of medical information may be provided to a user associated with a first service provider, and a second type of medical information may be provided to a user associated with a second service provider.

The analysis provided at step 1110 may be provided to any number of different devices, including, but not limited to, mobile communications device 115, mobile communications device 125, server 145, communications device 165, communications device 175, and/or a computing device of pharmacy 180. For example, data representing the extent of a chemical reaction may be generated at one device (e.g., mobile communications device 115) and may be sent to another device (e.g., a medical entity associated with a user of the mobile communications device, such as a device associated with the user's doctor). This may be done automatically or based upon user interaction at the sending device (e.g., selection of graphical user interfaces that select routing information for the sending of the data).

As part of step 1108, 1110, or another step in process 1100, a billing account may be selected based on the unique code. For example, a unique code may contain patient identification information, which may be linked to a billing account. In some embodiments, a billing account may be selected based on user inputs received at a device, such as mobile communications device 115. Information related to the billing account may be stored on any combination of mobile communications device 115, a database of insurance company 170, and/or any other device of system 100. In some embodiments, the selected billing account may be updated based on the analysis performed on the received image, the analysis provided, the number of times a color board 900 has been used, etc.

Disclosed embodiments may include urinalysis home testing kit. Such a kit may include a plurality of elements to enable testing of urine either at home or in any other environment.

One element in the kit may be a container configured to contain a urine sample. The container may have any form. It may have a fixed cavity size or a variable cavity size. For example, the container may be a collapsible cup or crucible, or any structure capable of holding a fluid.

The kit may also include a dipstick including a plurality of test reagent pads thereon for measuring differing urinary properties. The dipstick may have any shape or form and be made of any material capable of supporting test reagent pads. The reagent pads can be made of any material capable of providing analytic indications, upon exposure to a biological fluid (e.g., urine). Some non-limiting examples of such dipsticks may include dipstick 450, dipstick 500, dipstick 505, dipstick 510, and so forth.

The kit may further include a blot pad for removing excess urine from the dipstick after being dipped in urine, to thereby enable non-distorted image capture of the plurality of reagent pads by an image sensor. The blot pad may include, for example, any suitable absorptive material capable of absorbing urine to an extent the absorption eliminates or significantly reduces distortion in image capture that might otherwise occur if the dipstick is not blotted before image capture.

A colorized surface may also be included in the kit. The colorized surface may include a dipstick placement region. The dipstick placement region may be an area on the colorized surface on which the dipstick may be placed. The dipstick placement region itself need not be colorized, and may be characterized by markings or an outline indicating to a user that the region is reserved for dipstick placement. Some non-limiting examples of such colorized surfaces may include colorized surface 132, color board 900, and so forth.

The colorized surface may include a plurality of colored reference elements greater than a number of the plurality of test reagent pads, for enabling color normalization of the plurality of test reagent pads using the plurality of colored reference elements. These reference elements may be disbursed across the colorized surface to enable through image analysis comparison, effects of local lighting conditions.

Figure 12:
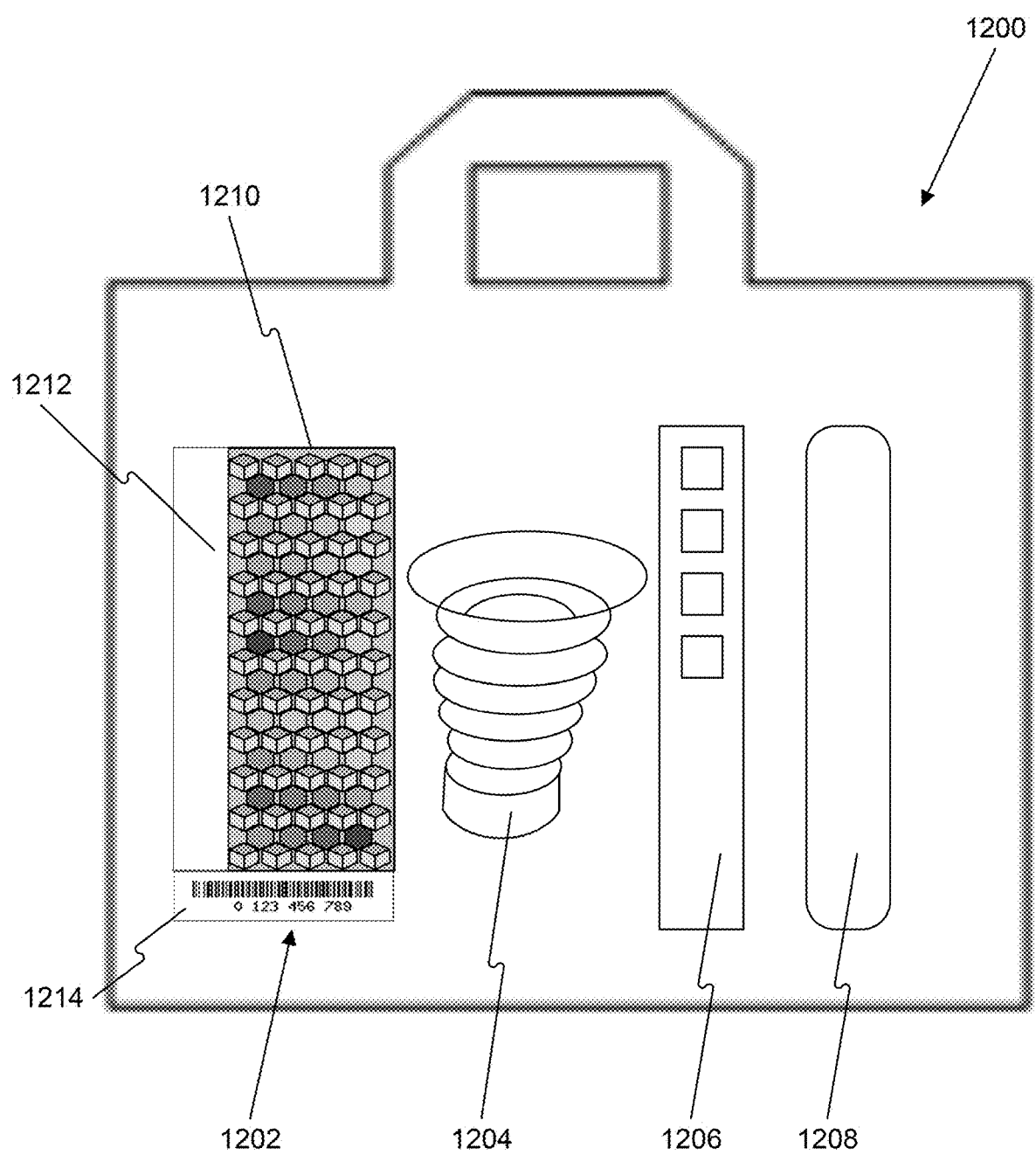
FIG. 12 is an illustration of a urinalysis kit, consistent with the present disclosure.

FIG. 12 depicts a urinalysis kit 1200. Though use in other locations are possible and are within the scope of this disclosure, urinalysis kit 1200 may be designed for use by an individual for a urinalysis test at a home. Moreover, while urinalysis kit 1200 may be described in a context of analyzing urine, other liquids (e.g., biological fluids) and/or objects may also be analyzed using elements and processes described herein.

In this exemplary embodiment, urinalysis kit 1200 contains a color board 1202, which may be used for analyzing a dipstick (e.g., at least one test reagent pad on a dipstick 1206). In some embodiments, color board 1202 may appear the same or similar to color board 900, as described in connection with FIG. 9. For example, color board 1202 may be a surface that may include reference elements on a colorized surface 1210, an analysis region 1212, and/or a unique code 1214, which may be the same as or similar to colorized surface 902, analysis region 904, and unique code 906, respectively. For example, unique code 1214 on color board 1202 may be configured to enable identification of properties of analysis of a test object (e.g., urinalysis performed on a dipstick), consistent with the disclosed embodiments. At least one reference element on color board 1202 may be associated with a test reagent pad (e.g., a test reagent pad on a dipstick 1206). In some embodiments, color board 1202 may appear the same as or similar to colorized surface 132. In some embodiments, at least two reference elements may be associated with a single reagent pad. This may allow for multiple color comparisons for a reagent pad, which may provide for more accurate analysis.

In some embodiments, analysis region 1212 may be configured to receive a dipstick 1206. For example, analysis region 1212 may be based on dipstick 1206 (e.g., is a similar size or shape as dipstick 1206). In some embodiments, a color board 1202 may have a plurality of color reference elements on a first side of an analysis region 1212, and may have another plurality of color reference elements on a second side of the analysis region 1212. The analysis region 1212 may also have a distinct color, shape, texture, etc. to differentiate it (e.g., to an analysis device) from colorized surface 1210 and/or a test object. For example, analysis region 1212 may be of a darker color or a lighter color than dipstick 12016 and/or analysis region 1212. As another example, analysis region 1212 may have a unique border around it. However, as with color board 900, in a broadest sense, this disclosure is not limited to a particular configuration, as a variety of configurations are possible and are within the scope of this disclosure.

Urinalysis kit 1200 may also include a container 1204, which may be configured to contain a urine sample. Container 1204 may be made from plastic, paper, or any material or combinations of materials capable of retaining fluid. In some embodiments, the interior of container 1204 may be coated with an impermeable material. In some embodiments, container 1204 may be transparent or translucent, which may allow a user to see a color of a liquid within container 1204. While container 1204 may take a variety of shapes and sizes, in some embodiments it may have a general profile of a tapered cup, such that it has an opening at its top that is larger than its base. In other embodiments, container 1204 may have an opening that is smaller than its base, which may reduce the risk of spillage. Container 1204 may also include a removable lid, which may be closed by a user to reduce the risks of spillage and/or inadvertent contact with a contained liquid. While container 1204 may be configured (e.g., by having an appropriate size, shape, composition, etc.) to contain any quantity of a liquid or semi-liquid, in some embodiments, container 1204 may be configured to contain between 75 mL and 750 mL of urine. In some embodiments, container 1204 may have a fill line or other indicator on it that indicates a proper amount of liquid for a user to put in the container. The fill line may be sized to correspond to a size of the dipstick, to thereby ensure that when dipped, the liquid covers each reagent pad.

In some embodiments, container 1204 may have an adjustable size, which may be accomplished in a number of ways. For example, container 1204 may have a series of ridges (such as those shown in FIG. 12), which may allow the walls of container 1204 to compress, such as when sufficient force is applied. In this example, force may also be applied to stretch container 1204 back to a larger size. As another example, container 1204 may have a number of alternating flexible and less flexible regions that allow a portion of container 1204 to be collapsed to decrease its size. In some embodiments, urinalysis kit 1200 may also include a funnel to assist a user in depositing a liquid into container 1204. Such a funnel may also be of adjustable size as container 1204 and/or may be made of similar materials.

Urinalysis kit 1200 may also include a dipstick 1206, which may have any number of test reagent pads (shown as exemplary squares on dipstick 1206 in FIG. 12) for measuring differing properties (e.g., urinary properties). In some embodiments, dipstick 1206 may have one or more test reagent pads that measure an albumin to creatinine ratio (i.e., based on the degree of a chemical reaction on and/or in the pad). For example, dipstick 1206 may include a first test reagent pad that measures a first property associated with albumin concentration, and may include a second test reagent pad that measures a second property associated with creatinine concentration. Other test reagent pads may measure other properties, such as a property associated with leucocytes in urine, a property associated with blood in urine, and/or a property associated with nitrite in urine. As yet another example, a test reagent pad may be configured to measure a property associated with a urinary tract infection. Any combination of properties may be measured depending on the number and configuration of test reagent pads on a dipstick 1206.

Different reagent pads may exhibit different colors or shades, depending on the test liquid to which they are exposed. Test reagent pads may be labeled and/or ordered to identify their testing purposes to a user and/or a processing device. For example, a reagent pad may have a label of "albumin concentration test." As another example, the test reagent pads may be ordered based on a predefined order, which may be determined and/or confirmed by a processing device after reading unique code 1214.

Urinalysis kit 1200 may also include a blot pad 1208 for absorbing liquid. In some embodiments, blot pad 1208 may be configured to absorb liquid from any number of test reagent pads on a dipstick 1206 (e.g., after a dipstick 1206 is dipped in urine contained in container 1204). Blot pad 1208 may have an absorption capacity that is based on a size of at least one reagent pad, an absorption capacity of at least one test reagent pad, a type of liquid being used for testing, and/or a number of reagent pads on a dipstick 1206. By way of example, blot pad 1208 may have an absorption capacity of between 0.5 mL to 5 mL. In some embodiments, blot pad 1208 may be attached to a package of urinalysis kit 1200, which may allow for ease of manufacturing. In other embodiments, blot pad 1208 may be attached to color board 1202. As a blot pad 1208 may differ based on a color board 1202 and/or urinalysis kit 1200 with which it is associated, attaching the blot pad 1208 to the color board 1202 or urinalysis kit 1200 may help ensure that the blot pad stays with a corresponding correct color board 1202 or urinalysis kit 1200.

Figure 13:
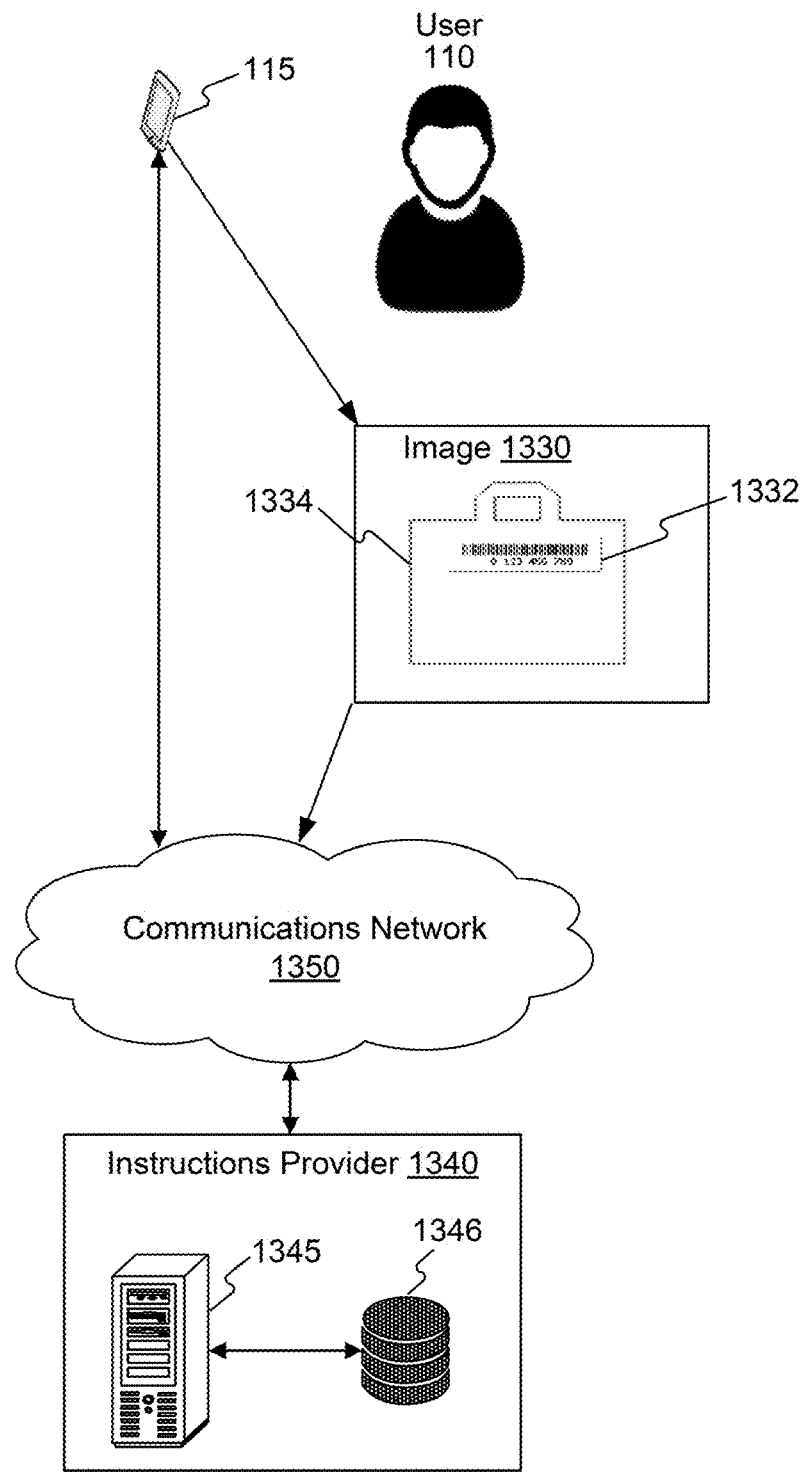
FIG. 13 is a schematic illustration of a urinalysis kit image processing system, consistent with the present disclosure.

FIG. 13 is a schematic illustration of a urinalysis kit image processing system 1300, which may be used to process an image from a device and process a sequence of instructions based on subsequent actions taken at the device. In some embodiments, urinalysis kit image processing system 1300 may be used in connection with a mobile communications device 115 that may communicate with communications network 1350 (which may be identical or similar to communication network 150), such as by sending image 1330 to communications network 1350. Mobile communications device 115 may be operated by a user 110. User 110 may send image 1330 from mobile communications device 115 to communications network 1350.

Image 1330 may include a depiction of at least part of urinalysis kit 1334, which may be an instance of urinalysis kit 1200. Image 1330 may also include a depiction of a visual link 1332, which may be attached to urinalysis kit 1334. Either though detection of unique characteristics of the kit and/or the visual link 1332, image 1330 may be used to confirm the identity of the test being performed. In some embodiments, visual link 1332, which may be the same as or similar to unique code 906, may include any combination of a number, an alphanumeric sequence, a barcode, a QR code, a unique visual pattern, a unique pattern of punches, a unique pattern of embossing, and/or any other visual indicator. Visual link 1332 may be machine-readable, and when read by a processing device, visual link 1332 may prompt certain operations to take place at mobile communications device 115, communications network 1350, and/or other processing devices. For example, visual link 1332, when read by a processing device, may prompt the initiation of process 1400, as will be described later in greater detail.

Visual link 1332 may include encoded information, which may be related to features of unique code 906, including, without limitation, a color board identifier, a geographical region, a production line, a creator of the color board, a health care provider, a type of desired medical test (urinalysis to determine pregnancy, urinalysis to determine a bladder infection, a spit test to determine a mouth infection, etc.), attributes of a user of urinalysis kit 1200 (or of any part of urinalysis kit 1200, of a color board such as color board 900, of a dipstick, etc.), specific chromatic properties, a range of chromatic properties. Any of this information may be encoded directly in visual link 1332, or visual link 1332 may direct a device to any of this information contained in an external location (e.g., a database or other data structure).

In some embodiments, mobile communications device 115 may send image 1330, visual link 1332, and/or information associated with any of visual link 1332, color board 1202, container 1204, dipstick 1206, blot pad 1208, and urinalysis kit 1200 to communications network 1350. In some embodiments, communications network 1350 may send the information received from mobile communications device 115 to instructions provider 1340, which may include a server 1345 and a database 1346. In certain embodiments, instructions provider 1340 may be a medical analysis unit 140 or a healthcare provider 160. Instructions provider 1340 may interpret the information received from mobile communications device 115 and may provide information to mobile communications device 115 in response. For example, instructions provider 1340 may receive information based on visual link 1332, which may be associated with a particular type of desired medical test, and may provide instructions associated with that type of test to mobile communications device 115 in response. In some embodiments, these instructions may be stored at database 1346. As another example, instructions provider 1340 may receive an image 1330 from mobile communications device 115 that has at least one unreadable portion and in response may send a notification to mobile communications device 115 that prompts a user 110 to capture a new image 1330 and/or activates an image sensor of mobile communications device 115. Having visual link 1332 attached to a urinalysis kit 1334 may help ensure that instructions for a specific urinalysis kit 1334 are provided (for example, different urinalysis kits 1334 may be configured for different medical tests and therefore may have different associated instructions, identical urinalysis kits may be provided to different users that needs different instructions and/or different medical analysis, and so forth).

A method of this disclosure may be used for guiding a user to utilize a urinalysis home testing kit. The user may be a patient or an individual assisting a patient. The utilization may occur at home, or at any other location.

Consistent with the disclosure, the user may be instructed to collect a urine sample in a container provided in the urinalysis home testing kit. This instruction (as well as all other instructions described herein) may occur through sound, text, video, graphics or a combination of one or more of the forgoing. The manner of instruction and/or the extent of the instruction may vary depending on factors such as the experience of the user with the test. If the system recognizes the user as having performed the test successfully multiple time in the past, shorted instructions may be provided.

The instruction may be provided via a server for storage on a mobile communications device of the user, or may be accessed in real time via a remote server in communication with the mobile communications device via a network.

Consistent with embodiments of the invention, the user may also be instructed to dip a dipstick provided in the urinalysis home testing kit in the urine sample. This instruction may include a time element as over or under exposure of the reagent pad may impact the accuracy of the test. To this end, the instruction may include a mechanism for timing the exposure of the reagent pad to the urine sample.

Also consistent with the disclosure, the user may be instructed to blot the dipstick using a blot pad provided in the urinalysis home testing kit to remove excess urine from a reagent area, and to place the dipstick on a reference surface displaying at least two reference color regions.

Figure 14:
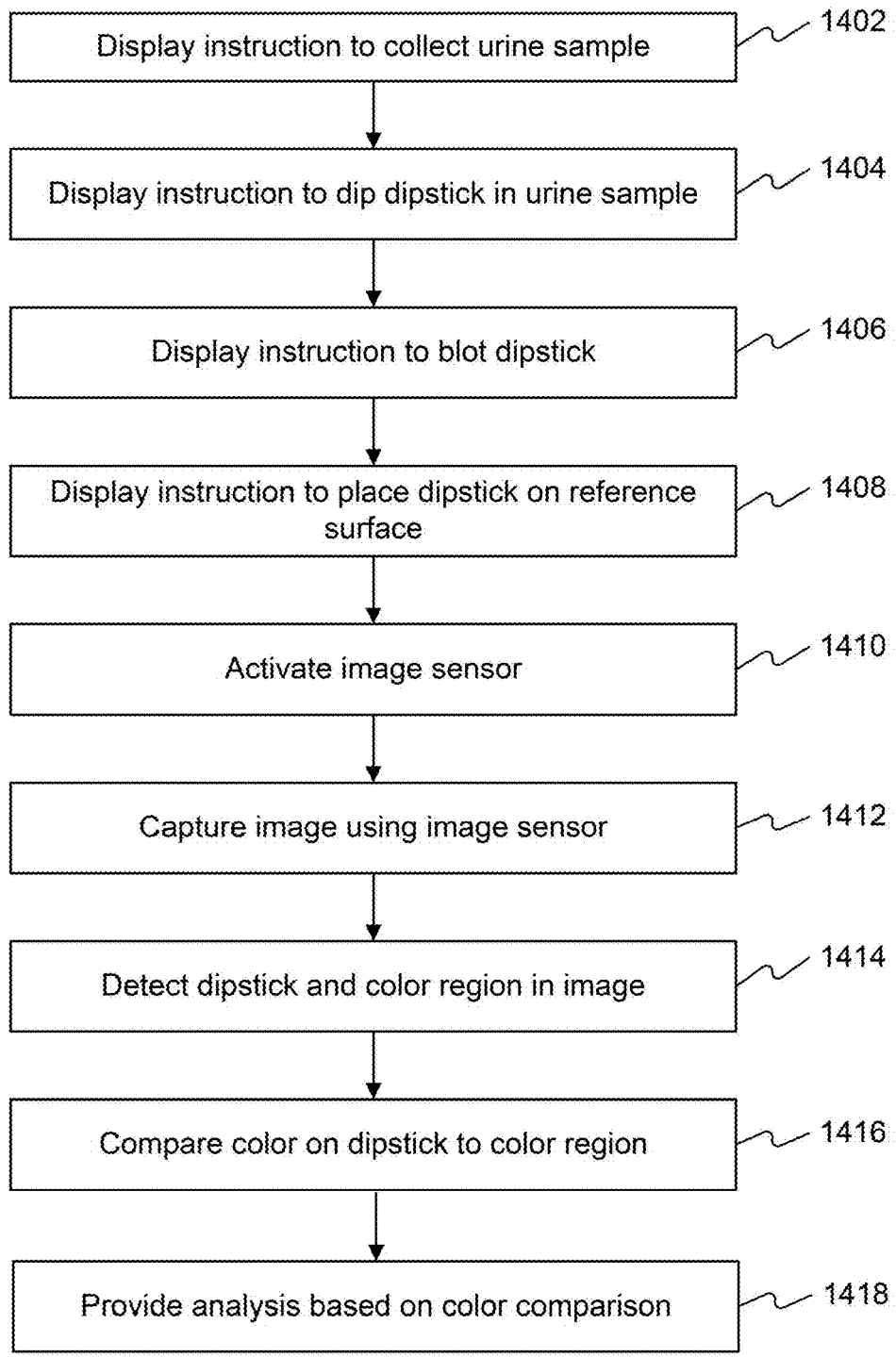
FIG. 14 is a flowchart of a process for collecting and analyzing urinalysis information, consistent with the present disclosure.

In addition, consistent with the present disclosure, the user may be instructed to use an image sensor to capture in a common image a depiction of the blotted dipstick and the at least two reference color regions, in order to use the at least two reference color regions as a guide to providing a test result through interpretation of the blotted dipstick relative to the at least two reference color regions. The image capture may occur on the same mobile communications device as used to present the instruction to the user. The instructions may involve a timer to ensure that the image capture occurs within a prescribed time beginning with exposure of the reagents to the urine sample. By way of non-limiting example, FIG. 14 depicts a process for collecting and analyzing urinalysis information, which may be performed by any combination of processing devices, such as mobile communications device 115, server 1345, etc., consistent with the present disclosure. Any of the instructions described herein may comprise text, an image, an animation, and/or a graphical user interface (GUI). In some embodiments, instructions may be displayed with selectable buttons, sliders, and/or other interactive graphical elements. At any step in process 1400 (e.g., after an action of one of the steps has been performed), a processing device may cause a display of a confirmation button, and may not proceed to another step in process 1400 until a selection input is detected at the confirmation button (e.g., a user 110 selects the button at a mobile communication device 115). The processing device may be remote from the mobile communications device 115. For example, the processing device may be part of a remote server that through a networked connection causes instructions to be displayed in real time. Or the same processing device may cause the instructions to be transmitted to the mobile communications device to be stored for later display. Alternatively, the processing device could be part of the mobile communications device itself.

At step 1402, a processing device may cause a display of an instruction instructing a user 110 to collect a urine sample. In some embodiments, this instruction may instruct the user 110 to collect a urine sample in a container 1204 that is part of a urinalysis kit 1200. In some embodiments, this instruction may include a particular amount of urine to be deposited (10 mL, ¾ of the capacity of the container 1204, etc.), a minimal required amount, a maximal required amount, and so forth. In some embodiments, an image sensor may capture an image of container 1204 and a processing device may determine, based on an analysis of the image, whether the proper amount of liquid is in the container 1204. For example, a machine learning model may be trained using training examples to determine an amount of liquids in container 1204 from images, and the trained machine learning model may be used to analyze the image and determine the amount of liquids in container 1204.

Further, the determined amount may be compared with a set of requirements (e.g., a threshold defined in memory accessible to a processing device) to determine whether the proper amount of liquid is in the container 1204. A training example may include an image of a liquid in a container 1204 together with an indicator of the amount of liquids in container 1204, a portion of an image, color information associated with an image, and/or any other data capable of training a machine to determine an amount of liquid in a container.

At step 1404, a processing device may cause a display of an instruction to dip a dipstick 1206 in a urine sample, which may be contained in container 1204. Dipstick 1206 may be part of a urinalysis kit 1200. In some embodiments, this instruction may include a desired dipping motion and/or a desired amount of time that dipstick 1206 should be held within the urine sample before withdrawing it. A processing device may also display a timer to a user 110 that indicates an amount of time remaining that the user 110 should keep the dipstick 1206 in the urine sample.

At step 1406, a processing device may cause a display of an instruction to blot a dipstick 1206 on a blot pad 1208, such as to remove excess urine from a reagent area of the dipstick 1206. Blot pad 1208 may be part of a urinalysis kit 1200. This instruction may include a degree of pressure to be exerted between the dipstick 1206 and the blot pad 1208, an amount of time the dipstick 1206 should be held to the blot pad 1208, a number of times the dipstick 1206 should be tapped to the blot pad 1208, an indication of a side of dipstick 1206 to face blot pad 1208, etc.

At step 1408, a processing device may cause a display of an instruction to place the dipstick 1206 on analysis region 1212. Analysis region 1212 may be part of a color board 1202, which may be part of a urinalysis kit 1200. This instruction may include information regarding a proper orientation of the dipstick 1206 relative to the analysis region 1212. Analysis region 1212 may have a colorized surface 1210 next to it, which may depict any number of color reference elements. In some embodiments, colorized surface 1210 may have at least two reference elements. For example, colorized surface 1210 may have at least two reference elements per reagent pad on a dipstick 1206, which may allow for multiple color comparisons of a reagent pad, which may improvement analysis. In some embodiments, analysis region 1212 may be in between two portions of surface 1210 such that reference elements are located on opposing sides of the analysis region 1212.

At step 1410, an image sensor of a processing device may be activated. The image sensor may be a camera of a mobile communications device 115, an imaging device connected to a computer, or any other imager capable of capturing an image. Upon activation, the processing device either directly or through transmitted instructions, may cause an image captured by the image sensor to be analyzed. The image may also be displayed. The processing device either directly or through previously transmitted instructions, may cause information to be overlaid on the displayed image, which may guide a user 110 to capture an image of desirable quality (having proper lighting, a proper orientation of an object for analysis, etc.). For example, the processing device may cause an overlay of a colored outline (e.g., a bounding box) of a color board 1202, an analysis region 1212, a dipstick 1206, etc. onto a live image seen by the image sensor. As another example, the processing device may cause a notification to a user regarding image quality to be displayed, such as an indication that the lighting is insufficient, the orientation is incorrect, etc. In some embodiments, the processing device may determine, such as based on a current image viewed by the image sensor, a current illumination of an object in the image (color board 1202, an analysis region 1212, a dipstick 1206, etc.). Based on the current illumination, processing device may directly or indirectly determine that a currently viewed image is not desirable for analysis, and may cause the issuance of a prompt to the user 110 to take an action to adjust the illumination of the image (move the image sensor and object to be imaged to a different location, adjust the lighting in a surrounding environment, rotate a dipstick 1206 relative to an analysis region 1212, etc.). In some embodiments, the processing device may cause automatic actions to adjust characteristics of the image to make it more desirable for analysis. For example, the processing device may cause adjustment to the exposure, contrast, focus, and/or other photographic settings to improve the quality of the image for analysis. Graphical user elements may be provided to a user to make these adjustments manually. In some embodiments, these actions to improve image quality may take place at the same device capturing the image, which may, for example, conserve processing resources of remote analysis system (e.g., medical analysis unit 140) and increase the quality of images sent to such a remote analysis system. In some embodiments, the instruction may include instructing a user to use a mobile communications device 115 to capture an image of the blotted dipstick 1206 next to the colorized surface 1210, and may also instruct this image to be captured prior to expiration of an image capture time window.

At step 1412, an image may be captured by an image sensor. This image may be captured with the image sensor that was activated at step 1410. In some embodiments, this image may be captured in response to a user action (e.g., a user selects a graphical user interface element at a mobile communications device 115). In some embodiments, the image may be captured after the processing device has determined that a currently viewed image of an image sensor is of desirable quality for analysis. In this manner, images of poor quality may be excluded from capturing and sending to a processing device (e.g., medical analysis unit 140) for analysis, which may save bandwidth and processing resources. The desirable quality may be determined by any combination of thresholds associated with local illumination, resolution, contrast, a number of detected objects for analysis (a dipstick 1206, a reagent pad, a reference element, etc.), an orientation of a detected object for analysis, an angle of the image, a distance of an object in the image from an image sensor, etc. In some embodiments, the processing device that captured the image may send it to another device for processing and/or analysis (i.e., performing a combination of steps 1414, 1416, and 1418). In some embodiments, processing device may prevent a user 110 from capturing an image before the beginning of a time window. The time window may be based on determinations made at a processing device. For example, based on instructions from a remote processor, mobile communications device 115 may detect a selection of a confirmation button indicating that a user 110 has finished blotting a dipstick 1206, and the time window may begin after a particular amount of time has passed since the finishing of the blotting. In another example, mobile communications device 115 may detect a selection of a confirmation button indicating that a user 110 has finished dipping dipstick 1206, and the time window may begin after the particular amount of time has passed since a finishing of the dipping. In an additional example, mobile communications device 115 may instruct user 110 to being dipping dipstick 1206, and the time window may begin after a particular amount of time has passed since the instruction to dip dipstick 1206 was provided. In another example, mobile communications device 115 may analyze a video feed depicting handling of dipstick 1206 to identify an occurrence of a particular event in the handling of dipstick 1206 (such as a beginning of dipping of dipstick 1206, a finishing dipping of dipstick 1206, a finishing of blotting dipstick 1206 on a blot pad, etc.), and the time window may begin after a particular amount of time has passed since the identified occurrence of a particular event. As yet another example, mobile communications device 115 may begin the time window after it has determined that a currently viewed image of an image sensor is of desirable quality for analysis. In some embodiments, if instructions provided by a processing device determines that a captured image is not suitable for analysis, but the time window has not yet expired, a user may be instructed to capture another image. Instructions provided by a processing device may also prevent a user 110 from capturing an image after the time window has passed. In some embodiments, a processing device may cause a notice to be provided to a user that an image capture time window is about to end (e.g., by displaying the notice at a display of mobile communications device 115).

At step 1414, an image of a dipstick (e.g., 1206) may be captured together with a color region. The color region may include reference elements on a colorized surface, such as colorized surface 1210. In some embodiments, the processing device may cause the detection of at least one reagent pad and at least one color reference element, which may be associated with an analysis test for the at least one reagent pad. In some examples, a detected element (dipstick 1206, color reference element, reagent pad, row of color reference elements, etc.) may be tagged with an identifier for use in analysis. For example, a color reference element may be tagged with an identifier indicating it is associated with a test for a creatinine concentration of a reagent pad (which may have its own identifier). In some examples, elements, such as color reference elements and reagent pads, may be identified based on their relative position within other objects, such as the relative position of a color reference element within a color board or the relative position of a reagent pad on a dipstick, for example as described above. In some embodiments, elements such as color reference elements and reagent pads may be identified based on their relative position with respect to other elements, such as position markers 474 and 475. In some embodiments, the detection may be based on the distinct color, shape, texture, etc. of analysis region 1212, discussed with respect to FIG. 12. In some examples, an identity of an element, such as color reference elements and reagent pads, may be verified based on the appearance of the element. For example, an element, such as a color reference element or a reagent pad, may be associated with a range of valid colors, valid shapes, and/or valid textures, and the appearance of the element in the image may be analyzed to determine whether the color, shape, and/or texture of the element is within the range of valid colors, valid shapes, and/or valid textures. In one example, in response to a determination that the color, shape, and/or texture of the element is not within the range of valid colors, valid shapes, and/or valid textures, one or more additional steps or actions involving the kit make occur, such as the color board and/or the dipstick may be forgone, and in some cases, an error notification may be provided. For example, the system may forgo providing medical information based on the kit, the color board and/or the dipstick in response to the determination that the color, shape, and/or texture of the element is not within the range of valid colors, valid shapes, and/or valid textures, and may provide the medical information in response to a the determination that the color and/or texture of the element is within the range of valid colors and/or valid textures.

In some embodiments, step 1414 may further include analyzing the image to determine whether a dipstick is a valid dipstick. For example, a dipstick may be an unauthorized dipstick, may include a different number of reagent pads than required, may include different types of reagent pads than required, may include the reagent pads in a different order than required, may be unsuitable for a particular medical analysis, and so forth. In one example, a machine learning model may be trained using training examples to determine whether dipsticks are valid from images of dipsticks, and the trained machine learning model may be used to analyze the image and determine whether the dipstick is a valid dipstick for the process. Such training examples may include an image of a dipstick together with an indicator of whether the dipstick is a valid dipstick, a portion of an image, color information associated with an image, and/or any other data capable of training a machine to determine whether a dipstick in an image is valid, consistent with the disclosed embodiments. In some examples, in response to a determination that the dipstick is invalid, one or more additional steps or actions involving the kit may occur, such as the color board and/or the dipstick may be forgone, and in some cases, an error notification may be provided. For example, the system may forgo providing medical information based on the kit, the color board and/or the dipstick in response to the determination that the dipstick is invalid, and may provide the medical information in response to the determination that the dipstick is valid.

In some embodiments, step 1414 may further include analyzing the image to determine whether a color board is a valid color board for the process. For example, a color board may be an unauthorized color board, may include a different number of color reference elements than required, may include different types of color reference elements than required, may include the color reference elements in a different arrangement than required, may be unsuitable for a particular medical analysis, and so forth. In one example, a machine learning model may be trained using training examples to determine whether color boards are valid from images of color boards, and the trained machine learning model may be used to analyze the image and determine whether the color board is a valid color board for the process. Such training examples may include an image of a color board, together with a label indicating whether the color board is a valid color board, a portion of an image, color information associated with an image, and/or any other data capable of training a machine to determine whether a color board in an image is valid, consistent with the disclosed embodiments. In some examples, in response to a determination that the color board is invalid, one or more additional steps or actions involving the kit may occur, such as the color board and/or the dipstick may be forgone, and in some cases, an error notification may be provided. For example, the system may forgo providing medical information based on the kit, the color board and/or the dipstick in response to the determination that the color board is invalid, and may provide the medical information in response to the determination that the color board is valid.

At step 1416, a color on dipstick 1206 may be compared to a color region, such as one or more elements on a colorized surface 1210. For example, a processing device may cause a comparison of a color of a reagent pad on dipstick 1206 to a color of one or more reference elements in the image captured at step 1412. As another example, a color of a reagent pad on dipstick 1206 may be compared to at least one chromatic property (e.g., a chromatic property determined according to process 1100). In some embodiments, a color comparison result may be generated after at least one color comparison is made.

At step 1418, an analysis may be provided, based on the color comparison performed at step 1416. In some embodiments, the analysis may be performed at one device, such as a server 145, and provided to another device, such as a mobile communications device 115. The analysis may include information related to the comparison performed at step 1416. For example, the analysis may include a similarity percentage between a color on dipstick 1206 and a color region, which may be based on the comparison. The analysis may also include information detailing a number of tests performed using dipstick 1206 (e.g., a test for determining an albumin concentration) and/or results associated with one or more of those tests. In some embodiments, the analysis may include analysis derived from the color comparison performed at step 1416. For example, a processing device may determine, based on any combination of any number of color comparisons, that at least one color comparison indicates a result for a particular condition (pregnancy, a bladder infection, a mouth infection, a nutrient deficiency, etc.). Such a result may have an associated degree of likelihood (e.g., 70% chance of pregnancy), which may be based on a degree of similarity between a chromatic property of a color of a reagent pad and a reference element. In some embodiments, analysis results may be inconclusive. For example, dipstick 1206 may not have been blotted sufficiently to produce reliable analysis results, dipstick 1206 may not have been properly dipped, etc. In some embodiments, when analysis results are inconclusive, a processing device may display an instruction. For example, a processing device may display an instruction instructing a user to reblot the dipstick 1206 or blot a new dipstick 1206. As another example, a processing device may display an instruction instructing a user to recapture an image of dipstick 1206.

According to one aspect of the disclosed embodiments, systems, methods, and computer readable media are set forth that allow for the automatic updating of a patient electronic medical record (EMR) with results from an image analysis. Such systems, methods, and computer readable media may utilize at least one processor. As used herein, the term "at least one processor" refers to any structure or combinations of structures capable of performing logic operations on data, regardless of whether such structure(s) are collocated or disbursed. For example, the at least one processor may include a processor of processing device 202, a processor within a mobile communications device (e.g., mobile communications devices 115 and 125), a processor within a server (e.g., server 145) remote from the mobile communications device, and so forth. In another example, such processors may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing device may include at least one processor configured to perform functions of the disclosed methods such as a microprocessor manufactured by Intel™. The processing device may include a single core or multiple core processors executing parallel processes simultaneously. In one example, the processing device may be a single core processor configured with virtual processing technologies. The processing device may implement virtual machine technologies or other technologies to provide the ability to execute, control, run, manipulate, store, etc., multiple software processes, applications, programs, etc. In another example, the processing device may include a multiple-core processor arrangement (e.g., dual, quad core, etc.) configured to provide parallel processing functionalities to allow a device associated with the processing device to execute multiple processes simultaneously.

The at least one processor may include any structure capable of performing logic operations on data. The at least one processor can embodied in any form, such as a personal computer, laptop computer, desktop computer, tablet computer, notebooks, mobile phone, a terminal, a kiosk, PDA, a cloud-based computing device, local or remote server(s) smart phone, smart device or any other system allowing for processing of information. By way of one example of an embodiment of this disclosure, in FIG. 18, processor 1801 is disclosed, exemplary operations of which are described later in greater detail.

According to one aspect of this disclosure, the at least one processor may be configured to generate a token for a specific patient in need of a medical test. The token may be any means to secure information being transmitted from one location to another. For example, the token may be a key, an identifier, a code, or any other data that aids in authentication of a transaction or transmission. The transmission may take place over a personal area network, local area network, wide area network, global network, the Internet, communications network 150, or any wired or wireless communication path. The token may be randomly generated or generated based on an algorithm or series of algorithms. A database, or token vault, may store the relationship between a sensitive value and the token.

In one example, the token may be generated for a person in need of a medical test. A specific patient may be any person in need of a medical test. A medical test may be a urinalysis, a saliva analysis, a stool analysis, a blood analysis, sweat analysis, or any test that involves the measurement of a physical, chemical or biological component from a patient. In another example, the token may be generated for a particular test ordered by a particular medical care giver to a particular patient.

In one aspect, the at least one processor may be configured to transmit the token to a mobile communications device of a specific patient, such as mobile communications device 115. The mobile communications device may be capable of allowing communication between a patient and the system. A mobile communication device may take the form of a phone, a smart phone, a smart watch, a tablet, a laptop, a personal computer, a PDA, smart glasses, or any device which may allow for communication between a patient and the system. The transmitting may take place over any wired or wireless connection, for example over communications network 150.

Figure 18:
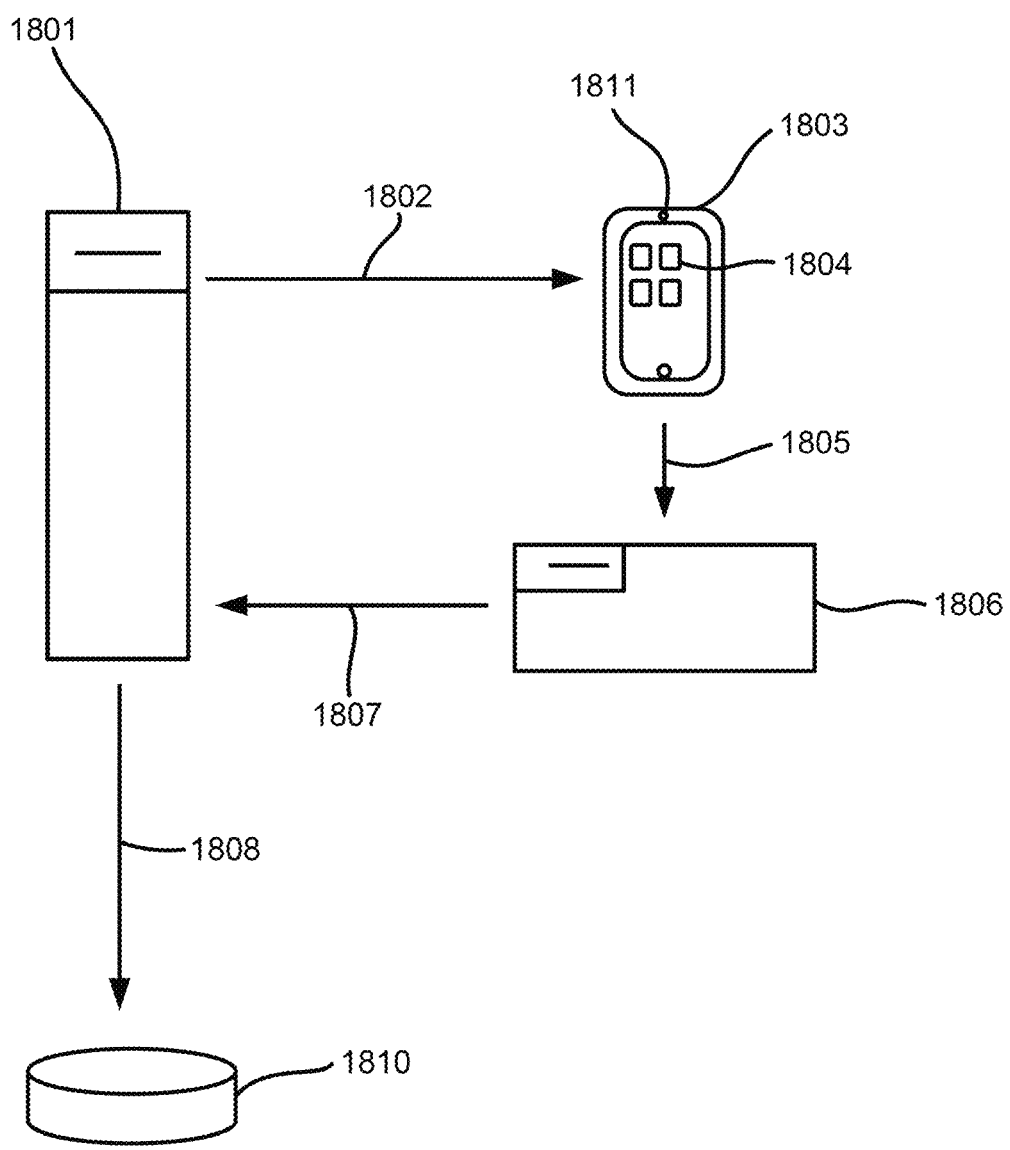
FIG. 18 is a schematic diagram illustrating one aspect of the system for integrating results of image-based analysis with electronic medical records, in accordance with disclosed embodiments.

By way of one example with reference to FIG. 18, the token may be transmitted to a mobile communications device 1803. For example, mobile communications device 1803 may be identical or similar to mobile communications devices 115 and 125 described above. The mobile communications device 1803 is illustrated with an app 1804 for aiding a patient. An example of communication (such as a token-based communication) between the mobile communication device 1803 and a remote server 1806, is shown at step 1805. In one example, in step 1805 the mobile communication device 1803 may provide and/or transmit the token, or information based on the token, to remote server 1806. Further, in some examples, in step 1805 the mobile communication device 1803 may provide and/or transmit image-related information (discussed later in greater detail) to remote server 1806. For example, in step 1805, the image-related information may be provided in a way that associates it with the token, or with the information based on the token. In communication 1807 between remote server 1806 and processor 1801, verification may occur, confirming that transmitted image-related information (discussed later in greater detail) is associated with the specific patient. In one example, in communication 1807, remote server 1806 may provide and/or transmit the token, or information based on the token, to processor 1801. Further, in some examples, in communication 1807, remote server 1806 may provide and/or transmit image-related information (discussed later in greater detail) to processor 1801. For example, in communication 1807, the image-related information may be provided in a way that associates it with the token, or with the information based on the token. In communication 1808 from processor 1801 and database 1810, an updating of an electronic medical record may occur in database 1810, for example based on the token and/or the image-related information. In some examples, communication 1808 may occur directly from remote server 1806 to database 1810.

In one aspect, the at least one processor may enable a communication session (such as a token-based communications session) to take place between a mobile communications device of a specific patient (such as mobile communication device 1803) and at least one remove server (such as remote server 1806). The remote server may include a single server or one of a plurality of servers. The remote server may take the form of one or more cloud-based devices. The at least one remote server may be associated with at least one of a healthcare provider, an agent of a healthcare provider, a private party, a clearinghouse, a government agency, or any party having an interest in the managing of health-related data or electronic medical records. In some examples, processor 1801 may be part of remote server 1806, while in other examples processor 1801 may be separate from remote server 1806. In one example, remote server 1806 may be similar or identical to server 145.

Disclosed embodiments may involve a communications session that includes transmission from the mobile communications device of image-related information obtained via an image sensor associated with the mobile communications device. A communications session may include any one-way or multi-way transmission or group of transmissions that involves the conveyance of information. In exemplary disclosed embodiments, the transmission may relate to one or more images. For example, the information may be derived from an image sensor that may include any device capable of detecting and converting optical signals in the near-infrared, infrared, visible and/or ultraviolet spectrums into electrical signals. Such sensors may be embodied in, for example, in the mobile communications device itself, or may be embodied in a device associated with a mobile communications device. By way of example, an image sensor 1811 (e.g., embedded camera, image sensor 226, etc.) in mobile communications device 1803, may be used to transmit image-related information in the transmission. The image-related information may be the image itself, a subset of the image, or information derived from the image or a portion thereof. In some examples, in communications session may associate the transmitted image-related information with the token, or with information based on the token.

In some exemplary disclosed embodiments, the image-related information may reflect a resulting color of a chemical reaction between a biological substance and a reagent. The biological substance may be any biological material, such as, but not limited to, urine, mucus, sweat, breast milk, stool, interstitial fluid, secretions, or any other biological material that is capable of causing a reagent to change color. The reagent may vary depending on the desired reaction, as each differing biological substance may have differing reactions with differing reagents. While reactions with reagents may be part of image-related information in some aspects of this disclosure, in other embodiments, as is discussed in other portions of this disclosure, the image-related information may be associated with an image that does not involve a reaction with a reagent.

In some disclosed embodiments, the at least one processor may be configured to verify or determine, based on the token or information based on the token, that the image-related information is associated with the specific patient. The token may be, for example, a series of bits that can be verified by the receiver as having originated with an authorized transmitter. The token, may take the form of a kind of security key, password, passphrase, automatically generated code, digital signature, biometric data, or any other form of data capable of enabling a receiver to verify that it is receiving information from a verified sender. For example, verification may be performed by comparing a token submitted or transmitted by a patient in conjunction with transmission with a token generated by the system. In some examples, the token or information based on the token may identify a particular patient and/or a particular medical care giver and/or a particular medical test and/or a particular medical test kit (such as particular urinalysis test 1200). For example, the token or information based on the token may include an index to an entry (e.g., in a data structure and/or a database) that comprises the identifying information, may encode the identifying information, and so forth. Further, in some examples, the at least one processor may be configured to determine, using the token or information based on the token, the identity of the particular patient and/or of the particular medical care giver and/or of the particular medical test and/or of the particular medical test kit (such as particular urinalysis test 1200). In some examples, the at least one processor may be configured to verify that the identified particular patient and/or particular medical care giver and/or particular medical test and/or particular medical test kit is compatible with the image-related information. For example, the at least one processor may verify that the image-related information is based on a type of medical test kit that matches the type of the identified particular medical test kit. In another example, the at least one processor may verify that the image-related information includes information that matches the type of the identified particular medical test. In some examples, in response to a failure to verify that the identified particular patient and/or particular medical care giver and/or particular medical test and/or particular medical test kit is compatible with the image-related information and/or to a determination that the identified particular patient and/or particular medical care giver and/or particular medical test and/or particular medical test kit is incompatible with the image-related information, the at least one processor may forgo one or more actions (such as one additional steps) and/or forgo a particular update to an EMR.

Figure 19A:
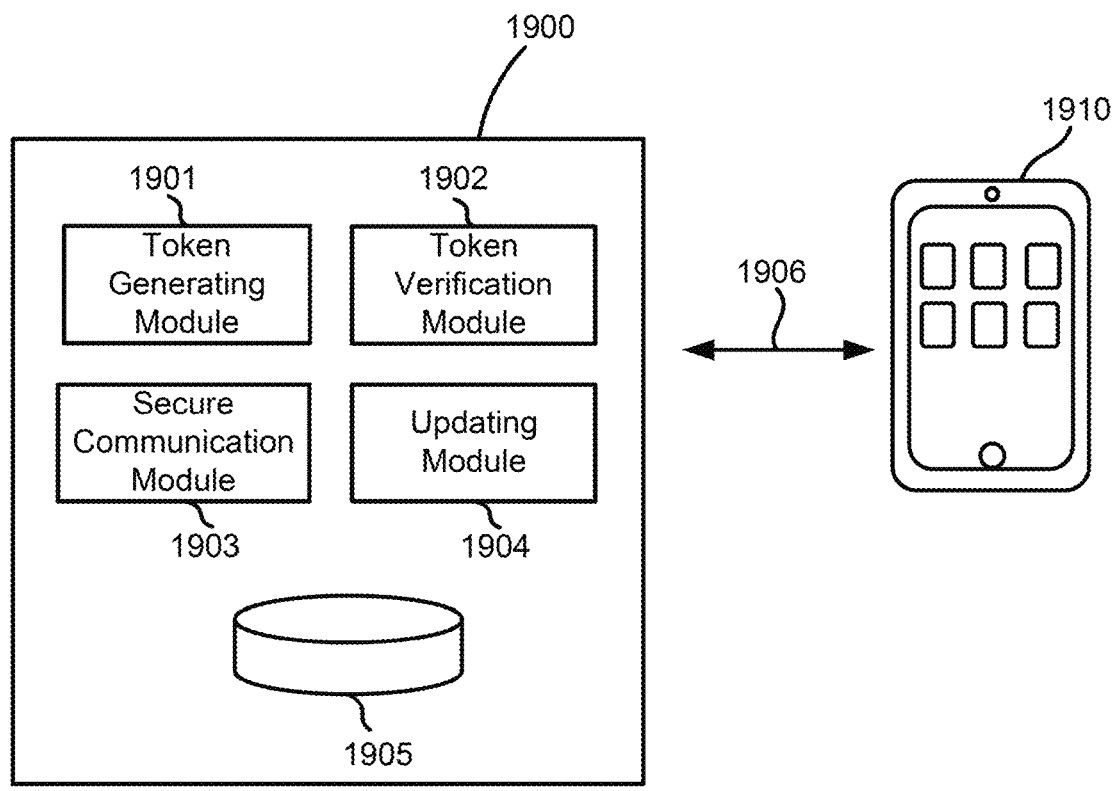
FIGS. 19A and 19B are schematic diagrams illustrating various configurations for the system of FIG. 18.
Figure 19B:
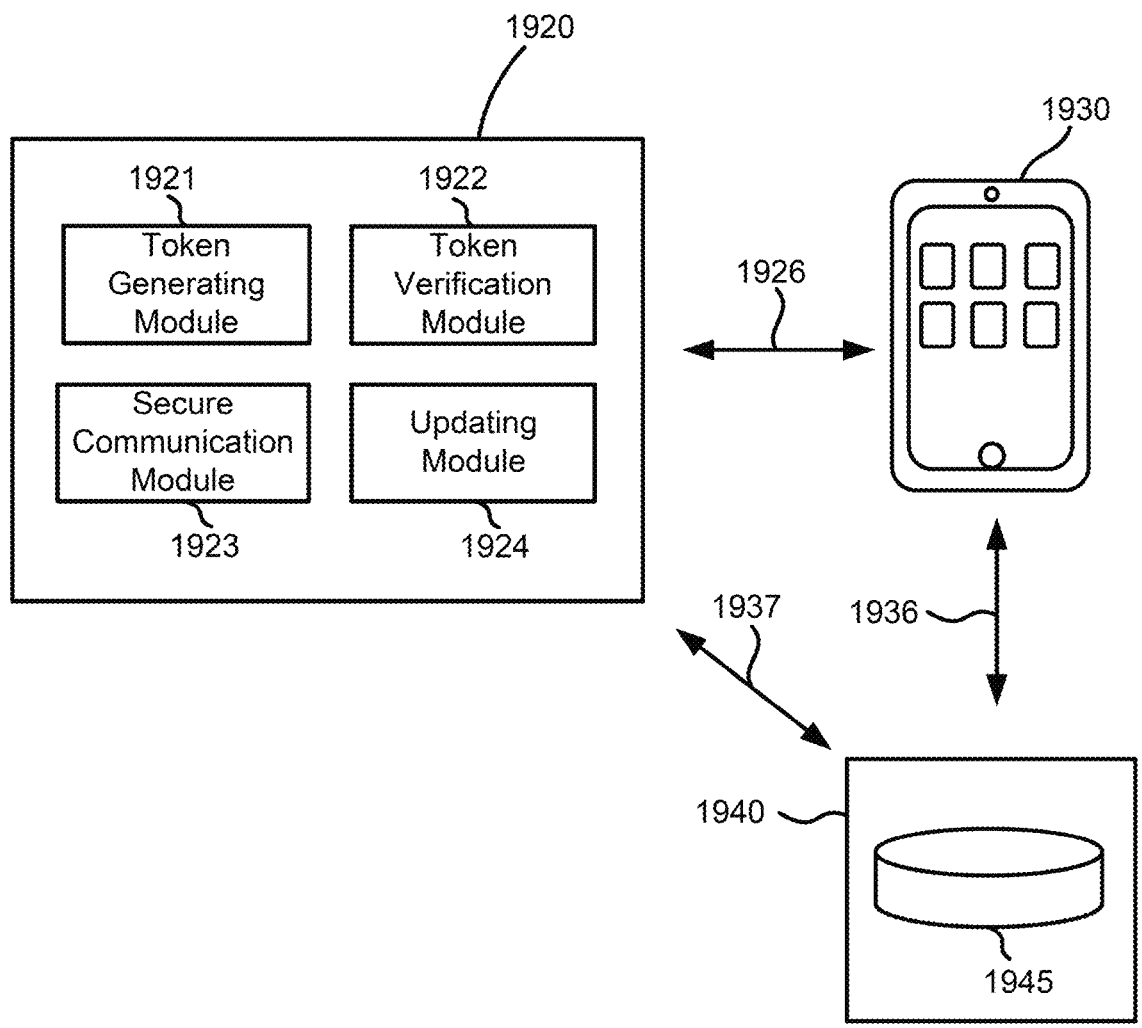

FIGS. 19A and 19B illustrate various configurations of a system consistent with some embodiments of the disclosure. FIG. 19A illustrates a configuration where the server 1900 includes a token generating module 1901, a token verification module 1902, a secure communication module 1903, an updating module 1904, and an electronic medical record database 1905. In this configuration, server 1900 communicates with a mobile communications device 1910, for example as described above. Each module may comprise software, hardware or any combination of software and hardware in order to achieve the desired function of the module. For example, mobile communications device 1910 may be identical or similar to mobile communications device 1803, to mobile communications devices 115 and 125, and so forth. For example, server 1900 may include one or more of processor 1801, remote server 1806, server 145, and so forth. Token generating module 1901 may generate a token which may be used by the secure communication module 1903 in a communication session (such as a token-based communication session) 1906 between the mobile communications device 1910 and the server 1900. In communication session 1906, server 1900 may transmit the token to mobile communications device 1910, and a user may transmit image-related information to the server 1900, for example together with the token. In another example, the token may be provided to mobile communications device 1910 in a different way, for example the token may be provided to mobile communications device 1910 through a visual code included in a medical test equipment (such as visual link 1332 in urinalysis test 1200, unique code 1214 on color board 1202, unique code 906 on color board 900, unique code 515, and so forth), the at least one processer may be configured to determine the token from an analysis of an image of the visual code, and the token may be transmitted from mobile communications device 1910 in association with image-related information to the server 1900.

In a first example, the image-related information may include an image of a dipstick 450 adjacent or near a colorized surface 132. In such an example, after placing the dipstick 450 in a biological fluid, the user places the dipstick 450 on colorized surface 132 as shown in FIG. 4B, and utilizes mobile communications device 1910 to capture an image of colorized surface 132 and dipstick 450. The image may then be transmitted to server 1900, where the token verification module 1902 verifies that the image is associated with the user. The server 1900 may perform an analysis of the image and calculate a test result. Updating module 1904 may then update a personal electronic record found in EMR database 1905 for the user showing the test result. It is noted that mobile communications device 1910 may also (or alternatively) perform an image analysis and transmit a result of the analysis to server 1900. In such an alternative situation, a token may be used to verify that the transmitted analysis originates with the appropriate patient.

In a second example, the image-related information may reflect characteristics of different segments of at least one skin feature or tissue feature. A skin feature or tissue feature may include a growth, a mark, a scar, an injury or any blemish or element on a skin surface which may be indicative of a medical condition. Other types of image-related information for tissue other than skin may relate to the tongue, throat, genitalia, finger or toe nails, or other non-skin tissue (collectively referred to herein generically as "skin features"). By way of example, a user may place a colorized surface near to or adjacent a skin feature and capture an image of the skin feature and the colorized surface. The image may then be transmitted to server 1900, where the token verification module 1902 verifies that the image is associated with the user. The server 1900 may perform an analysis of the image and updating module 1904 may then update a personal electronic record found in EMR database 1905 with the result of the analysis. As in other embodiments, the mobile communications device 1910 may alternatively perform an image analysis and transmit a result of the analysis to server 1900.

FIG. 19B shows an alternate arrangement. As shown in FIG. 19B, server 1920 may be separate from a provider server 1940 containing EMR database 1945. The server 1920 may include a token generating module 1921, a token verification module 1922, a secure communication module 1923, and an updating module 1924. In this configuration, server 1920 may communicate via channel 1926 with a mobile communications device 1930 and may communicate via channel 1937 with provider server 1940. Additionally, provider server 1940 may directly communicate via channel 1936 with mobile communications device 1930. Each module may comprise software, hardware or any combination of software and hardware in order to achieve the desired function of the module. Token generating module 1921 may generate a token which may be used by the secure communication module 1923 in a communication session (such as a token-based communication session) via channel 1926 between the mobile communications device 1930, server 1920 and provider server 1940. In communication session via channel 1926, a user may transmit image-related information to the server 1920. As used herein, the term "channel" refers to any pathway or combination of pathways that enable communication of information. For example, a channel may include a single leg, or a combination of discrete wireless legs of one or more wireless networks, wired networks (with or without interposed servers or other equipment). Communication via channel 1926 may be similar or identical to communication session 1906 described above.

As alternatively illustrated in FIG. 19B, updating module 1924 may update a personal electronic record found in EMR database 1945 for the user showing the test result. EMR database 1945 may be updated via mobile communications device 1930 as via communication channel 1936 or by updating module 1924 of server 1920 via communication channel 1937.

It is understood that token generating module 1921, token verification module 1922, secure connection module 1923 and updating module 1924 may be incorporated into server 1920, mobile communications device 1930, provider server 1940, or a combination thereof as desired. For instance, token generating module 1921, token verification module 1922, secure connection module 1923 and updating module may be incorporated into mobile communications device 1930. Such a configuration may allow for directly updating of a user's electronic medical record from a secure mobile communications device 1930. Of course, so long as verification is enabled in some way, verification may occur with structures other than those in the provided examples.

In one aspect, the at least one processor may be configured to update a personal electronic medical record of the specific patient with a test result reflective of the verified image-related information. Updating a personal record may include the addition of any information related to the verified image-related information. For example, a personal electronic record may be updated to include a test result such as an analyte concentration, images received from the mobile communications device, the result of a test (e.g., positive or negative), a result of a urinalysis, a result of a medical test performed using process 700, a result of a medical test performed using process 800, a result of a medical test performed using process 1100, a result of urinalysis performed using process 1400, a result of process 1700, or any other information capable of being obtained from an image, metadata thereof, or other image-related information. The electronic medical record may be stored in a local database or memory, remote database or memory, or a plurality of local or remote databases or memory.

Figure 20:
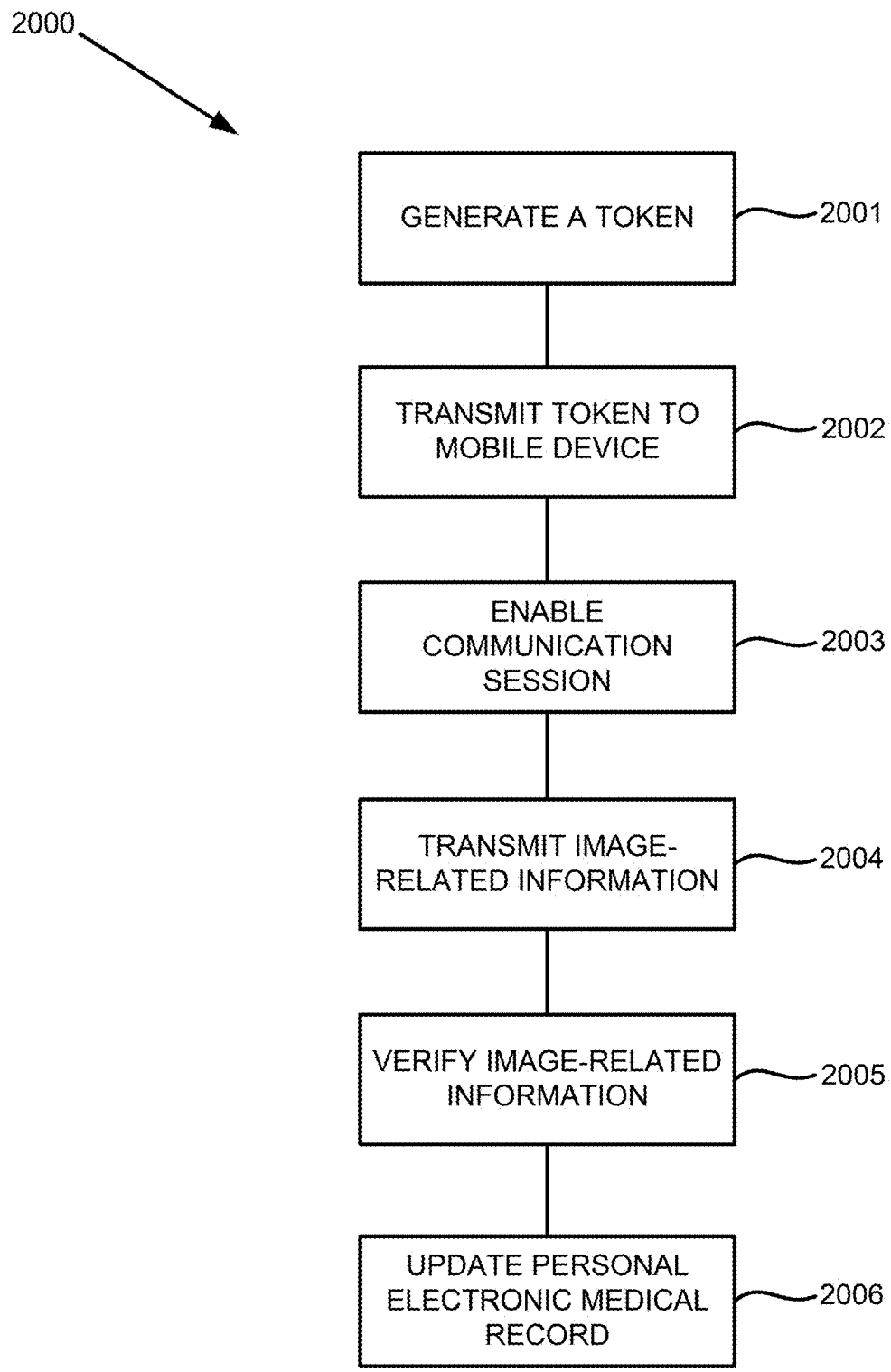
FIG. 20 is a flow chart illustrating a process of integrating results of image-based analysis with electronic medical records, in accordance with disclosed embodiments.

A method of securely updating personal electronic medical records 2000 in accordance with one aspect of the invention is illustrated in FIG. 20. The method may be capable of being carried out by at least one processor or plurality of processors configured to carry out the desired steps. A non-transitory computer readable medium may contain instructions that when executed by the at least one processor cause the at least one processor to perform a method, such as method 2000 illustrated in FIG. 20. The processor or processors may be local, remote, part of the cloud, or any combination thereof. A token may be generated in step 2001 for a specific patient in need of a medical test. The token may be indicative of an authorization for an image-based medical test for the specific patient, and the at least one processor that generates the token may be part of at least one remote server. The at least one remote server may be associated with at least one of a healthcare provider and/or an agent of the healthcare provider. The at least one remote server may be located within a healthcare institution such as a hospital or doctor's office. The at least one remote server may be associated with a clearinghouse that manages health related information.

In step 2002, the token may be transmitted to a mobile communications device of the specific patient. This may ensure that only the specific patient is able to update information related to the medical test, however in other embodiments, other authorized entities may additionally be provided with access. A communications session (such as a token-based communications session) may be enabled in step 2003. The communications session (such as the token-based communication session) may include sending a link from a healthcare provider to the mobile communications device associated with the specific patient after obtaining an indication that the specific patient needs the medical test. The link may be sent over any wired or wireless communication channel and may take the form of an email, SMS or text message, or any other form allowing for delivery of a link to a user. Enabling a token-based communication session may include sending an identifying detail of a patient to a remote server after obtaining an indication that the specific patient needs the medical test. An identifying detail may include a username, a phone number, an email, a physical address, a birthdate, photo, biometric parameter, or any detail associated with a patient which can be used to identify a specific patient. Alternatively, a test kit may include a unique code that serves as a token for enabling a verified communication session.

A communications session (such as a token-based communications session) may include causing a mobile communications device of the specific patient to provide guidance to the specific patient on how to successfully complete the medical test. Such guidance may include presenting directions on a display of a mobile communications device for one or a plurality of different medical tests. The directions may be given in the form of text, audio, animation, still images, or any combination thereof. Additionally, the directions may be given in the form of audible prompts. The directions may include interactive features capable of responding to prompts or questions presented by the patient. The guidance may include instructions to carry out a desired medical test. Such tests may include the sampling or testing of a biological fluid such as urine, saliva, blood, interstitial fluid or stool. The guidance may include instructions to do one or at least two of: opening a medical kit, expanding a collapsed measuring cup, dipping a dipstick, blotting the dipstick, placing the dipstick on a colorized test surface, capturing an image of a dipstick on a colorized test surface, recapturing the image of the dipstick on the colorized test surface, guidance on how to prick a finger for blood sampling, instructions to expose a reagent to a biological fluid and to capture an image of the exposed reagent within a predefined time window, or any information which may be beneficial in directing a patient to perform a testing procedure.

Once an image is obtained with a mobile communications device of a skin surface, a colorized surface, a reagent pad, or a combination thereof, the image-related information may be transmitted from the mobile communications device at step 2004. The image-related information may be transmitted to a local processing device, a memory, a server, a remote server or one or more cloud devices. At step 2005, the image-related information may be verified, for example based on the generated token, to be image-related information associated with the specific patient. (The order of image receipt and verification is not necessarily critical. For example, the communications session may be verified in advance of image receipt, in conjunction with image receipt, or after image receipt.) Once verification has taken place, an update to a personal electronic medical record of the specific patient takes place at step 2006. Updating the electronic medical record may include the transmission and/or storage of information relating to the test. Such information may include one or more test results, the transmitted image, data derived from the transmitted image, an analysis, or any combination thereof.

In some embodiments, a token-based communications session may include any communications session that enables the association of image-related information (for example, image-related information originating from a mobile communication device) with a particular patient (for example in a server that receives the image-related information) using a token configured to enable such association. In some examples, such token may be generated by the server, or by a device other than the mobile communication device. Further, in some examples, such association of image-related information and particular patient may be used, for example by the server, to update an EMR of the particular patient based on the image-related information. In one example, the token-based communications session may include a transmission of the token with the image-related information, for example from the mobile communication device to the server, while in another example, the token-based communications session may include a transmission of the image-related information in a way that enables an association of the image-related information with the token, without necessarily transmitting the token, for example by transmitting the image-related information in a communication channel associated with the token, by transmitting information indicative of the token with the image-related information, and so forth. In one example, the mobile communication device may receive the token, while in other examples the mobile communication device may never receive the token.

Consistent with some embodiments of the disclosure, a home testing kit may be distributed to a plurality of individuals with preexisting conditions, or to individuals that may be at risk for developing a certain medical condition, as part of a preventative health care program, or as directed by a healthcare professional. In one example, weight, diet, lifestyle, hereditary traits, geographic location, age, sex, and socioeconomic status may be factors that indicate an individual is more likely to develop a certain medical condition. The at least one processor may be configured to determine that a specific patient needs (or might benefit from) a medical test, and in response to that determination, trigger the sending of a home testing kit to the specific patient. The processor may analyze or query a database of one or more risk factors, patient characteristics, or other medical or patient-related information to make a determination that a patient should be sent one or more home testing kits. Additionally, the at least one processor may query a database of patients and initiate the sending of different types of medical tests to one, or a plurality of individuals randomly, at predetermined periods of time, or when prompted by an administrator or health care professional.

Once a medical test is delivered to a specific patient, the at least one processor may be configured to send reminders to the specific patient when the transmission of image-related information is not received within a selected time period after the home testing kit was sent. By reminding the patient, an increase in patient compliance may be achieved. The reminder may be sent to the mobile communications device associated with the patient, and may take the form of a visual reminder such as a text, email, animation or image; an audible reminder such as a beep, tone, or voicemail; a tactile reminder such as a vibration, or any combination thereof. The selected time period may be a predetermined time period for all patients, but may also be individually configured to a specific patient. Criteria such as a patient's age, past behavior of a patient (i.e. whether or not a patient has previously complied or not complied with a home health test), health provider, geographical region, type of medical test, and so forth may be used to develop a reminder type specific to an individual. A neural network or self-learning system may be used to develop reminders that achieve the greatest patient compliance for performing a home test and submitting image-related information.

The system may utilize a result from a medical test to create a prompt for a medical professional. The system may send a notification to a medical professional to bring attention to the medical professional about a result of a medical test. Such a notification may be useful to direct the attention of a medical professional to a result that deviates substantially from a norm. The at least one processor may be configured to cause a generation of a medical prescription for treating the specific patient based on the test result reflective of the verified image-related information. The prescription may then be sent to a medical professional for authorization. Once a specific patient has been associated with a test result, generating a medical prescription may be used as a notification to the medical professional that the test result has been received. A medical prescription may include a prescription for one or more drugs, vitamins, supplements, therapy, or any recommendation from a health professional based on the test result.

In one aspect, the medical test may be used to determine a parameter from a chemical reaction between a biological fluid and a test reagent. The color of the test reagent following the chemical reaction indicates a concentration or level of a measured parameter. The biological fluid may be blood, saliva, urine, mucus, sweat, breast milk, stool, interstitial fluid, secretion, or any other biological fluid. A dipstick, included as part of the home testing kit, may include more than one reagent. A plurality of test reagents may be positioned along the length of the dipstick for measuring differing biological fluid properties, analytes, or parameters. During the testing procedure, once the chemical reactions between the reagents and the parameters have completed, the dipstick is positioned proximate or adjacent to a colorized test surface. An image of the dipstick with corresponding reagents and the colorized test surface may be obtained. The transmitted image-related information may include an image of at least one test reagent adjacent a colorized test surface. The system may be configured to analyze an image prior to transmission. The transmitted image-related information may include data derived from image analysis of at least one test reagent adjacent a colorized test surface. Image analysis may include any type of analysis of an image, a portion of the image, or image-related information. If the medical test includes urinalysis, the transmitted image-related information may reflect resulting colors of multiple chemical reactions between a biological fluid and a plurality of test reagents for measuring differing urinary properties. The properties may include physical or chemical properties of the urine. Also, concentrations or amounts of various analytes, markers, compounds or components found in the urine may be detected. If the medical test includes saliva testing or salivaomics, the transmitted image-related information reflects resulting colors of multiple chemical reactions between a biological fluid and a plurality of test reagents for measuring differing saliva properties that may be used to screen for or diagnose numerous conditions and disease states, including Cushing's disease, anovulation, HIV, cancer, parasites, hypogonadism, allergies, circadian rhythms shifts, and any other condition capable of detection through saliva. The properties may include physical or chemical properties of the saliva. Also, concentrations or amounts of various analytes, markers, compounds or components found in the saliva may be detected. If the medical test includes stool analysis, the transmitted image-related information reflects resulting colors of multiple chemical reactions between a biological secretion and a plurality of test reagents for measuring differing stool properties that may provide indicators of bleeding, lactose intolerance, the presence of an infection, Steatorrhea, pancreatitis, or any other condition detectable via stool analysis. The properties may include physical or chemical properties of the stool. Also, concentration or amounts of various analytes, markers, compounds or components found in the stool may be detected.

In another aspect of the invention, the image-related information may reflect characteristics of different segments of at least one skin feature. The at least one skin feature may include one or a plurality of a skin mark, such as a mole, nevi, tumor, scar, freckle, blemish, cut, scrape, or any imageable feature on a skin surface, and the transmitted image-related information may be indicative of a change in visual characteristic of the skin mark. A visual characteristic may include a size, shape, color or any characteristic that is observable or capable of being seen or captured with an image sensor. Any feature that may be captured on an image may be a visual characteristic. A user may capture an image of skin feature with a mobile communications device and transmit the image to a remote server for analysis. The image may include image-related information. The transmitted image-related information may be data derived from image analysis of an image of the at least one skin feature being positioned adjacent a colorized test surface. The data may include any information related to an analysis of the image or a portion thereof. The skin feature may be positioned proximate or adjacent a colorized test surface when the image is captured such that the transmitted image-related information is an image of the at least one skin feature adjacent to a colorized test surface. Alternatively, an image of the skin feature may be compared to a separate image of a colorized test surface. The system utilizes the different colored portions of the colorized test surface to aid in an analysis of the skin feature. For example, the system may normalize colors of the skin feature in the image base on the colors of the colorized test surface in the image. Additionally, the system may measure skin features based on the measurements of the colorized test surface in the image. The colorized test surface may be used as a reference for a plurality of different analyses performed by the system. The system may perform an analysis based on a single image or a series of images over time. For example, the system may conclude a wound is infected by analyzing a single image and the associated image-related information. Alternatively, the system may analyze a series of images and the corresponding image-related information of a skin feature, and determine based on a change in the skin feature over time that the skin feature may be pre-cancerous or cancerous, that a wound is not healing properly, or that some other potential abnormality exists. The at least one skin feature may include at least a part of a wound and the transmitted image-related information may be indicative of healing progress of the wound. As mentioned above, this analysis may be performed over a period of time or a series of images. The colorized test surface recorded concurrently with each image in a series may be used by the system to account for changes in color of the wound during the healing process. Additionally, such a determination may be made against a benchmark image.

In another aspect, a non-transitory computer readable medium is disclosed for enabling automatic update of an electronic medical record via a patient's mobile communications device as discussed above, the computer readable medium containing instructions that when executed by at least one processor cause the at least one processor to perform a method. The method may include causing an electronic transmission of a token to the mobile communication device of the patient for use by a medical image capture application on the mobile communications device. A medical image capture application may include a program, software or code that operates on the mobile communication device. The method may include enabling via the medical image capture application, the patient to capture a medical image using a camera of the mobile communications device. The medical image may include an image of a testing kit, a portion of the testing kit, a skin feature, a biological fluid, a reagent, a plurality of reagents, or a combination thereof. The method may include enabling via the medical image capture application, processing of the image to generate medical data and to transmit the medical data along with the token, for verifying an identity of the patient. The method may include receiving the medical data and the token. The method may include verifying an identity of the patient using the token. Following identity verification, the method may include automatically populating an electronic medical record of the patient with the medical data.

Disclosed embodiments may involve receiving a first image of a plurality of adjacent wounds in proximity to a form of colorized surface having colored reference elements thereon, wherein each wound has multiple segments of differing colors. By their nature, wounds are not completely uniform and therefore exhibit segments having differing colors. In some instances, there are significant differences between wound segments and in some instances color variations of segments may be in the same family of colors. Colorized elements may be provided on a colorized surface to serve as references for analyzing wound segment colors.

Figure 15A:
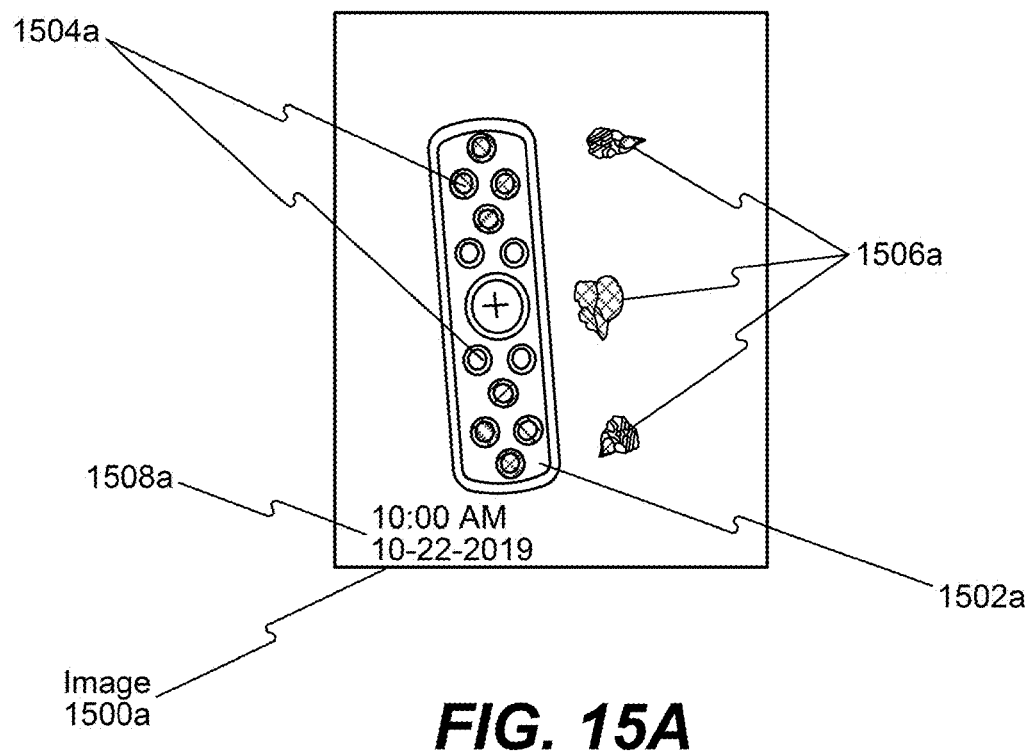
FIGS. 15A and 15B are illustrations of images of wounds and a color comparison surface, consistent with the present disclosure.

The colorized surface may take on any form in any shape or size, so long as the surface serves the intended analysis function. One example of a form of colorized surface is illustrated in FIG. 15A, where, on colorized surface 1502a, circular elements 1504a and 1504b exhibit differing colors. The form of colorized surface 1502a is illustrated as somewhat rectangular, however, this is only an example. It can be of any shape, size or material, so long as it achieves the function of serving as a source of color reference elements for a wound.

When patients have multiple wounds adjacent one another, distinguishing the wounds from each other and tracking their healing process can pose challenges. Disclosed embodiments enable the tracking of multiple wounds to provide feedback on the healing progress of each wound. To this end, disclosed embodiments may involve a first image of a plurality of adjacent wounds, which in some embodiments may be in proximity to a form of colorized surface.

Similarly, disclosed embodiments may involve receiving a second image of the plurality of wounds, for example in proximity to a form of colorized surface, to determine second colors of the plurality of wounds, wherein capture of the second image occurs at least one day after capture of the first image. The second image may be similar to the first image, but taken at least a day later. In the second image, the form of colorized surface may be the same instance of colorized surface as appeared in the first image; may be a duplicate of the colorized surface used in the first image, or may differ from the colorized surface in the first image, either in form or substance. In addition, the colorized surface in the second image may be placed in substantially a same location as in the first image, or may be placed in a different location. In some examples, only one of the first image and second image may include a depiction of a form of colorized surface, both the first image and second image may include a depiction of a form of colorized surface, both the first image and second image may include no depiction of a form of colorized surface, and so forth. In some examples, any one of the first image and second image may include any number of colorized surfaces (such as no colorized surfaces, one colorized surface, two colorized surfaces, three colorized surfaces, more than three colorized surfaces, and so forth).

Figure 15B:
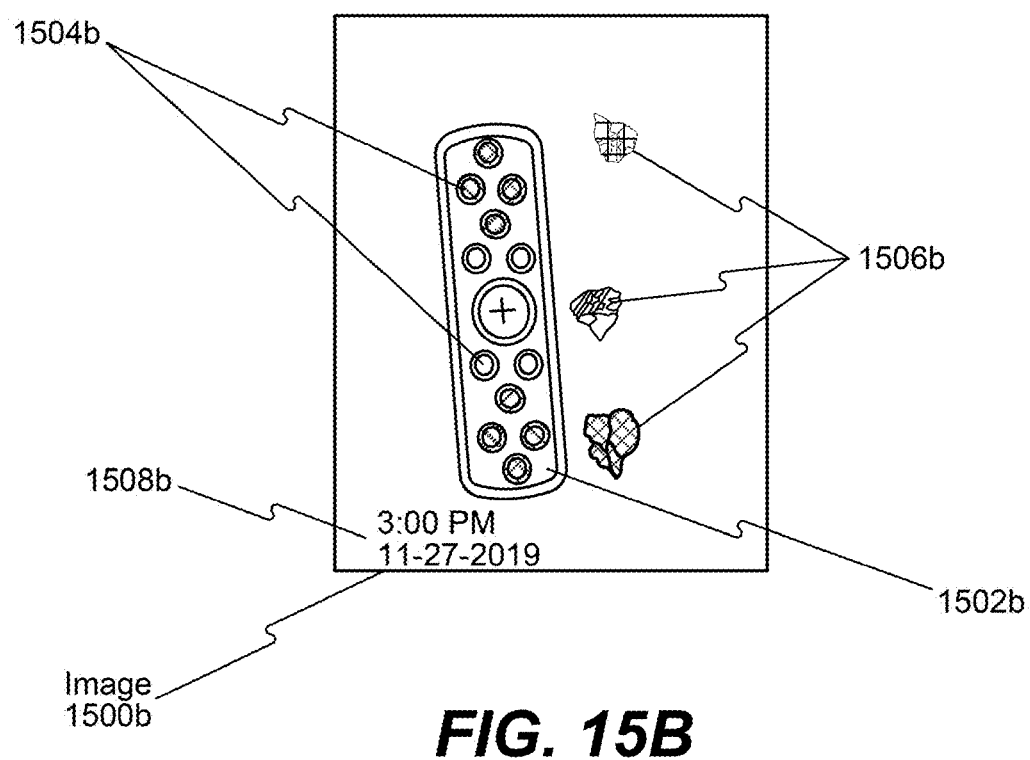

By way of one example, FIGS. 15A and 15B depict sequential images of a wound progression together with a color comparison surface. In particular, FIG. 15A illustrates image 1500a captured five days before the image of the same wounds in image 1500b of FIG. 15B. Image 1500a and/or image 1500b may have been captured by a device that may have an image sensor (or that may be otherwise associated with an image sensor), such as, for example, mobile communications device 115 or server 145. In some embodiments, image 1500a and/or image 1500b may have been captured, sent, received, etc. as part of an image analysis process, such as process 1700, described with respect to FIG. 17. In some examples, both image 1500a and image 1500b may have been captured by the same device, while in other examples, image 1500a and image 1500b may have been captured by different devices that may have different capturing capabilities and/or settings. In some examples, both image 1500a and image 1500b may have been captured using identical or substantially similar capturing parameters, while in other examples image 1500a and image 1500b may have been captured using different capturing parameters (for example, using different exposure time, different shutter speed, different aperture, different ISO, different lens, different illumination, different viewing angle, different frame rate, different resolution, and so forth).

As respectively illustrated in FIGS. 15A and 15B, image 1500a may include a colorized surface 1502a and image 1500b may include a colorized surface 1502b, either or both of which may be similar to an instance of colorized surface 132, for example as illustrated in FIG. 4A. However, any number of colorized surfaces may be included in an image. Colorized surface 1502a may depict at least one reference element 1504a and colorized surface 1502b may depict at least one reference element 1504b. Colorized surface 1502a and/or colorized surface 1502b may be configured for placing on human skin. In some examples, colorized surface 1502a and/or colorized surface 1502b may include any number of positioning markers (for example, no positioning marker, one positioning marker, two positioning markers, three positioning markers, more than three positioning markers, and so forth), such as positioning marker 410. Such positioning markers may be configure to enable detection of a position of a colorized surface by image analysis, to enable determination of an orientation of a colorized surface by image analysis, to enable identification through image analysis of portions of the colorized surface (such as reference elements) that may be based on their position with relation to the positioning markers, to enable measurement of a curvature of the colorized surface (for example due to an attachment of the colorized surface to the skin) through image analysis, and so forth. For example, colorized surface 1502a and/or colorized surface 1502b may be made of any combination of plastic, paper, paint, temporary tattoo, film, or any other material displaying a colorized surface. Colorized surface 1502a and/or colorized surface 1502b may also include an adhesive material, which may be on a back side of colorized surface 1502a and/or 1502b. In some embodiments, colorized surface 1502a and/or colorized surface 1502b may be made of a flexible material, which may allow the colorized surface to conform to contours of a surface (i.e., a portion of skin of a user) on which the colorized surface is configured to be placed and/or adhered. Colorized surface 1502a and/or colorized surface 1502b may be printed or otherwise generated using any suitable process.

As previously mentioned, the versions of colorized surfaces in the first image and the second image may differ. By way of example, in some embodiments, a printed form of colorized surface 1502a and/or colorized surface 1502b may be of a version that corresponds to a stage of healing progress of a wound. Thus, a version of colorized surface 1502a in image 1500a may differ from a version of colorized surface 1502b in image 1500b. In some disclosed embodiments, the form of colorized surface is a printed form and a same version of the printed form appears in both the first image and the second image. Thus, a version of colorized surface 1502a in image 1500a may be the same as a version of colorized surface 1502b in image 1500b (i.e., the same version of a printed form may appear in both image 1500a and image 1500b). In some embodiments, image 1500a and/or image 1500b may not include any colorized surface.

Reference elements 1504a and/or 1504b may be colorized for comparison to at least one wound. In some embodiments, the number, color, spacing, shape, orientation, placement, etc. of reference elements 1504a and/or 1504b may be based a characteristic of a user, including a characteristic of a wound of the user. For example, reference elements 1504a and/or 1504b may have any combination of a number, color, spacing, shape, orientation, placement, etc. based on a user's wound being a burn wound, a bite wound from a particular animal, an abrasion, a laceration, etc. As another example, reference elements 1504a and/or 1504b may have a number, color, spacing, shape, orientation, placement, etc. based on a user's skin pigmentation, a user's age, a user's gender, a medical condition of a user, etc. In some embodiments, reference elements 1504a and/or 1504b may be based on a stage of healing progress of a wound. Reference elements 1504a and/or 1504b may have specific chromatic properties associated with them (for example, the chromatic properties discussed regarding FIGS. 1A, 9, and 11).

As shown in FIGS. 15A and 15B, image 1500a and image 1500b may include wounds 1506a, 1506b, and 1506c, which may be in proximity to a form of a colorized surface. However, these wounds are merely exemplary, and any number of wounds may be in an image (such as no wound, a single wound, two wounds, three wounds, more than three wounds, and so forth). Also, while respective wounds in images 1500a and 1500b correspond with each other, embodiments may exist where a wound appears in one image, but does not appear in another image (for example, image 1500a may include a depiction of a wound that do not appear in image 1500b, image 1500b may include a depiction of a wound that does not appear in image 1500a, both image 1500a and image 1500b may include a depiction of the same wound, any combination of the above, and so forth). The number of the wounds in one image (such as image 1500a) may be identical to the number of the wounds in another image (such as image 1500b), may be different than the number of the wounds in another image (such as image 1500b), may be lower than the number of the wounds in another image (such as image 1500b), may be higher than the number of the wounds in another image (such as image 1500b), and so forth. Due to the time lapse between image 1500a and 1500b, the appearance of wounds 1506a, 1506b, and 1506c may likely differ between the two images, as is illustrated. Healthy human skin may or may not separate one wound from another in image 1500a and/or image 1500b. In some embodiments, wounds may be of similar or different types, such as a burn wound caused by heat, a chemical burn wound, a bite wound from a particular animal, an abrasion, a laceration, a wound resulting from surgery, etc. Wounds may also be associated with a particular stage of healing. In some embodiments, a wound may have any number of segments that have different visual appearances (e.g., color, color gradient, combination of colors, reflectiveness). These segments may be differentiated and detected by a device that processes an image of a wound, consistent with the disclosed embodiments.

In some embodiments, image 1500a and 1500b may each bear a timestamp 1508a and 1508b, respectively. The timestamp may be visual, as illustrated, and/or may be contained within metadata. A timestamp may correspond to a time and/or date at which an image was captured by an image processing device or may correspond to a time and/or date at which an image was sent or received by a device. In some embodiments, multiple timestamps may be included with an image (e.g., to indicate a time at which an image was captured, when it was sent to a device, when it was processed, when it was viewed, and so forth). A timestamp may be included with an image in a variety of ways. For example, a timestamp may be superimposed onto the image itself (e.g., as shown in FIG. 15). In some embodiments, a timestamp may also be embedded in an image.

In some embodiments, image 1500a and/or image 1500b may also include metadata (not shown). Such metadata may include, without limitation, a device identifier (e.g., based on a MAC address, IP address, port number, serial number, etc. of a processing device), user identification information (a name, address, phone number, social security number, insurance number, username, medical test number, etc.), patient information, a medical condition, a wound type, information associated with a medical professional (e.g., name of a primary care physician or wound specialist), a country of residence of the user, and/or a timestamp.

Disclosed embodiments may involve using the colored reference elements in the first image to determine first colors of the plurality of wounds, wherein during determination of the first colors, the colored reference elements may be used to correct for local illumination conditions. For example, one or more of the colored reference elements in the first image may be compared with image segments containing the wounds, to determine one or more colors of each wound. More than one colored reference may be used in order to account for local illumination conditions. That is, due to shading, non-uniform lighting, glare, or any other condition, wound colors may be misperceived by the image sensor. Similar misperceptions are likely to occur when processing the colored reference elements. Since the colored reference elements are known in advance (or can be determined by comparison to other colored reference elements), one or more correction factors can be applied to the images of the wounds, so that accurate wound colors can be determined, for example as described above.

Similarly, disclosed embodiments may involve using the colored reference elements in the second image to determine second colors of the plurality of wounds, wherein during determination of the second colors, the colored reference elements may be used to correct for local illumination conditions. The explanation in the previous paragraph with regard to the first image applies equally to the second image.

Disclosed embodiments may involve using the reference elements and/or the positioning markers in an image (such as the first image and/or the second image) to estimate length, size, depth, and/or volume associated with a wound. For example, known length and/or size of the reference elements and/or the positioning markers may be used to estimate a distance from the image sensor, the estimated distance of the reference elements and/or the positioning markers from the image sensor may be used to estimate the distance of at least part of the wound from the image sensor, and the estimated distance of at least part of the wound from the image sensor may be used to estimate length, size, depth, and/or volume associated with wound based on the length and/or size of at least a portion of the wound in pixels in the image. For example, it may be estimated that the distance of the wound from the image sensor is the same as the distance of the reference elements and/or the positioning markers from the image sensors. In another example, a curvature of the skin may be estimated, for example based on the positioning markers and/or on relations between distances of objects within the colorized surface, and the curvature may be used together with the estimated distance of the reference elements and/or the positioning markers from the image sensor to estimate the distance of at least part of the wound from the image sensor. In some examples, a correction factor may be calculated based on a relation between the known length and/or size of objects and the length and/or size of the objects on the colorized surface in pixels, and the correction factor may be used in order to transform the length and/or size of a portion of the wound in pixels in the image to real measurements, for example by multiplying the length and/or size in pixels by the correction factors. In some examples, a machine learning model may be trained using training examples to estimate length, size, depth, and/or volume of skin features (such as wounds, portions of wounds, etc.) from images of the skin features and colorized surfaces, and the trained machine learning model may be used to analyze the image (such as image 1500a and/or image 1500b) and estimate the length, size, depth, and/or volume of a skin feature. Such training examples may include an image of a wound with a colorized surface together with an indicator of a measurement of the wound and/or of a particular portion of the wound, a portion of an image, color information associated with an image, and/or any other data capable of training a machine to estimate the length, size, depth, and/or volume of a skin feature.

Figure 16:
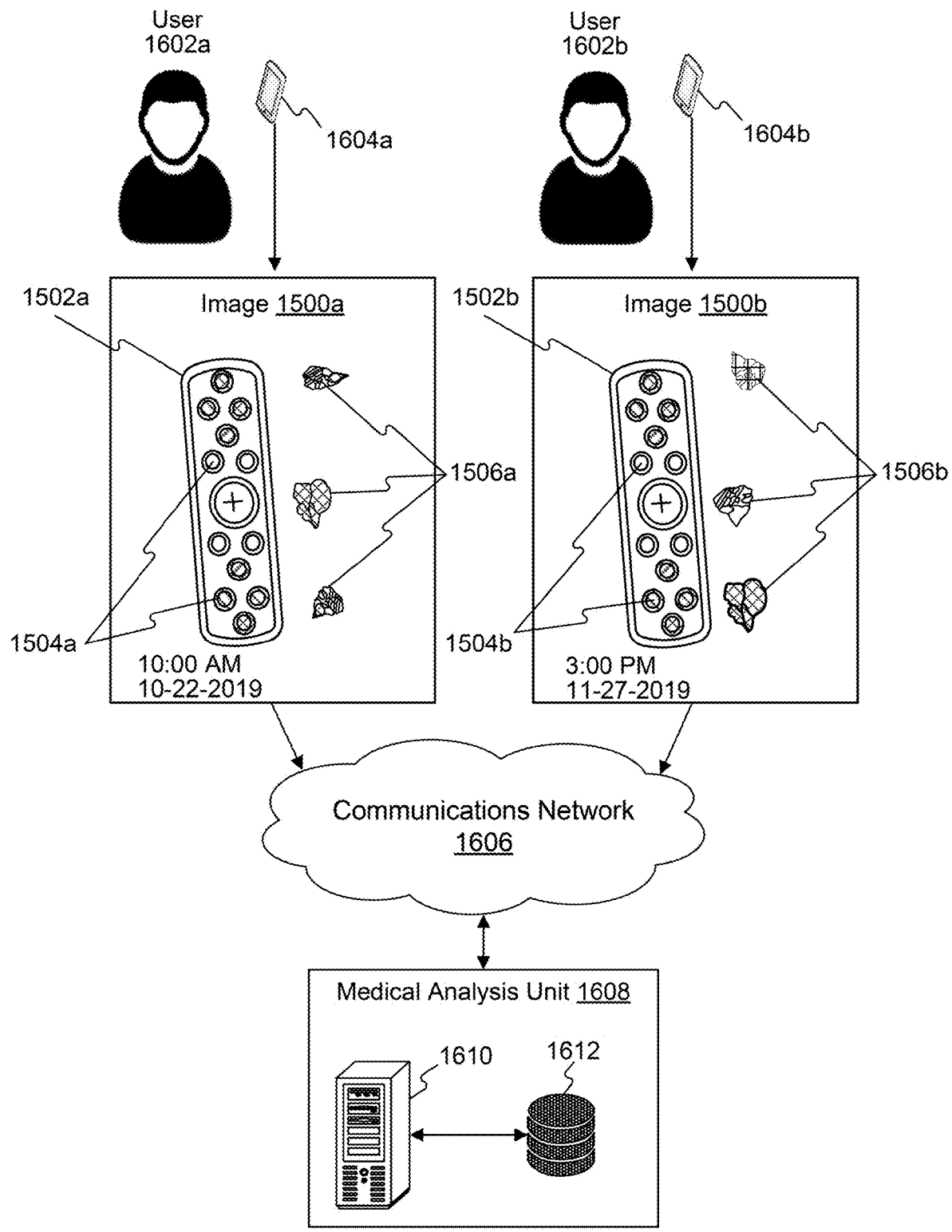
FIG. 16 is a depiction of an image processing system for analyzing wound images, consistent with the present disclosure.

By way of one example, FIG. 16 depicts a schematic illustration of a wound image analysis processing system 1600, which may be used to process an image from a device and process a sequence of instructions based on subsequent actions taken at the device. In some embodiments, wound image analysis processing system 1600 may involve the use of a mobile communications device 1604a (e.g., a smartphone) that may communicate with communications network 1606, such as by sending image 1500a to communications network 1606. Mobile communications device 1604a may be operated by a user 1602a. User 1602a may send image 1500a from mobile communications device 1604a to communications network 1606. In another example, mobile communications device 1604b may analyze image 1500b to generate image-related information based on image 1500b, and may send the generated image-related information based on image 1500b to communications network 1606. In some embodiments, image 1500b may also be sent to communications network 1606, such as by mobile communications device 1604b (e.g., a tablet) which may be operated by a user 1602b. In another example, mobile communications device 1604a may analyze image 1500a to generate image-related information based on image 1500a, and may send the generated image-related information based on image 1500a to communications network 1606. Images 1500a and 1500b may be captured, processed, and/or sent by the same mobile communications device, or different mobile communications devices, as illustrated in FIG. 16. Images 1500a and 1500b may be captured, processed, and/or sent by the same user, or by different users, as illustrated in FIG. 16. Image 1500a and/or image 1500b may include metadata, such as the metadata discussed with respect to FIG. 15.

Image 1500a and/or image 1500b and/or image-related information received at communications network 1606 may be forwarded to a medical analysis unit 1608. Medical analysis unit 1608 may include a server 1610, which may be coupled to one or more physical or virtual storage devices such as a database 1612. Server 1610 and/or database 1612 may contain programs, rules, applications, instructions, etc. used to process image 1500a, image 1500b and/or image-related information and perform medical analysis on information obtained from image 1500a and/or image 1500b. For example, medical analysis unit 1608 may carry out process 1700, described with respect to FIG. 17 below.

Figure 17:
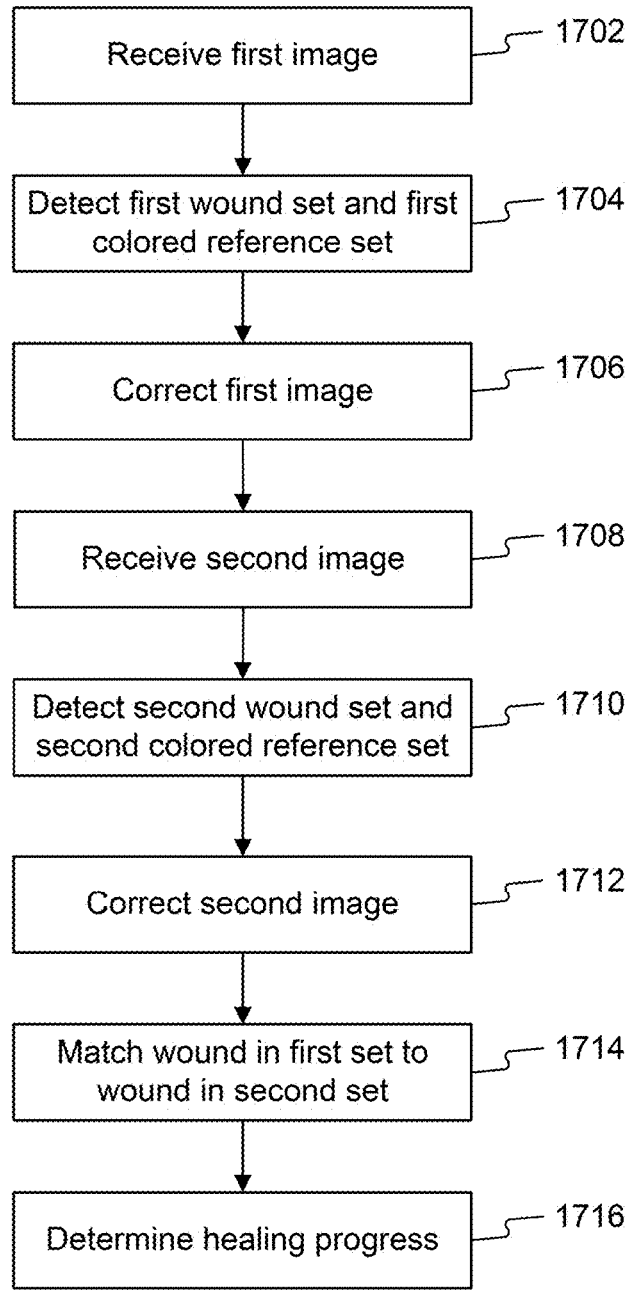
FIG. 17 is a flowchart of a process for analyzing an image of a wound, consistent with the present disclosure.

FIG. 17 depicts a process 1700 for analyzing an image of a wound, which may be performed by any combination of processing devices. Any of the instructions described herein may include text, an image, an animation, and/or a graphical user interface (GUI). In some embodiments, instructions may be displayed with selectable buttons, sliders, and/or other interactive graphical elements. By way of example only, at any step in process 1700 (e.g., after an action of one of the steps has been performed), a processing device may display a confirmation button, and may not proceed to another step in process 1700 until a selection input is detected at the confirmation button.

Disclosed embodiments may include receiving a first image of a plurality of adjacent wounds, for example in proximity to a form of colorized surface having colored reference elements thereon. As discussed, each wound may have multiple segments of differing colors. Other disclosed embodiments may include receiving a first image of a plurality of adjacent wounds. In step 1702, a first image and/or image-related information based on the first image may be received. The first image and/or the image-related information based on the first image may be received at a processor, regardless of where the processor is located. At step 1704, a first set of wounds may be detected. Further, in some examples, at step 1704 a first colored reference set may be detected. The colored reference set may be any set of color references uses to ascertain wound colors. In step 1706, the colors in the first image may be corrected. Specifically, due to local illumination conditions, the image sensor may misperceive actual wound colors. However, since the colored reference elements are captured in the same first image as the wounds and the colored reference elements are of known colors, if the colored reference elements are misperceived, the extent of the misperception can be determined, and an appropriate correction factor may be applied to wound colors in the first image, for example as described above. In some examples, step 1706 may be excluded from process 1700.

Similarly, in step 1708, a second image and/or image-related information based on the second image may be received, at a later time. The later time may be as short as a day later, and can be multiple days later or even longer. The second image may be captured by the same or a different image sensor that captured the first image. In much the same way as the wound set and colored reference set were detected in the first image, in step 1710 the second wound set and/or colored reference elements may be detected and in step 1712 the second image may be corrected. In some examples, step 1712 may be excluded from process 1700.

Next, in step 1714, a comparison may take place to match wounds in the first image with wounds in the second image. Due to progression of the wounds (such as healing) or other changes that may have occurred during the time lapse from the capture of the first image to capture of the second image, the shape, tissue composition, and/or color of one or more of the wounds may have changed. Therefore, image analysis may use location, relative size, distinct features, or other characteristics to match wounds in the second image with wounds in the first image. It is to be understood that herein any reference to a healing of a wound (such as healing progress, level of healing, etc.) may also refer to a worsening in the condition of the wound.

After the wounds are matched in step 1714, in step 1716, detected changes from the first wound to the second wound may be used to assess the wound progression and determine healing progress. By way of example only, one or more of changes in dimensions of the wound, changes in composition of tissue type within the wound, changes to the peri-wound skin, changes in surface features, changes in color, changes in texture, and/or changes in other characteristics may be used to determine the progress of wound healing.

While it is to be understood that the steps of process 1700 is not limited to the specific structures disclosed herein, structures disclosed herein (and other alternative structures) may be used to perform process 1700. By way of example, at step 1702, processing device (e.g., a server 1610) may receive an image. This image may be an image 1500a, which may have been captured using an image sensor of a device (e.g., mobile communications device 1604a). This image may include a plurality of wounds, which may or may not be in proximity to a form of colorized surface, as described with respect to FIG. 15.

At step 1704, a processing device, which may be different from the processing device receiving the image at step 1702 (e.g., an image analysis unit connected to communications network 1606), may detect a first wound set (e.g., a wound or plurality of wounds) and/or may detect a first colored reference set (e.g., colorized surface 1502a). In some embodiments, a first wound set and/or a colored reference set may be detected based on portions of human skin separating wounds or separating a wound from a colored reference set. A first wound set may also be detected based on a comparison of the colorized reference elements to chromatic information of the wound set. In other embodiments, such as those where no form of a colorized surface is in the image, a first wound set may be detected based on analyzing the chromatic information, contrast with human skin, orientation, shape, etc. of the wound set. For example, a processing device may compare the received image to other images of wounds stored in a database (e.g., database 1612), and/or may apply an image analysis algorithm to the received image, where the algorithm contains parameters related to chromatic properties, size of regions (e.g., a wound region, skin region, etc.), etc. In some embodiments, the processing device may determine a set of colors, orientation, shape, chromatic information, etc. of the first wound set. In some examples, a machine learning model may be trained using training examples to detect wounds in images, and the trained machine learning model may be used to analyze the image and detect the first wound set. Such image may include any number of colorized surfaces, including no colorized surface, one colorized surface, two colorized surfaces, more than two colorized surfaces, and so forth. Such training examples may include an image of wounds with no colorized surface together with labels indicating the wounds in the image and/or the locations of the wounds in the image, a portion of an image, color information associated with an image, and/or any other data capable of training a machine to detect wounds and wound information. Another example of such training example may include an image of wounds with one or more colorized surfaces, together with labels indicating the wounds in the image and/or the locations of the wounds in the image. In some examples, an artificial neural network (such as deep neural network, convolutional neural network, etc.) may be configured (for example, manually, using machine learning methods, by combining other artificial neural networks, etc.) to detect wounds in images, and the artificial neural network may be used to analyze the image and detect the first wound set.

In disclosed embodiments, during determination of the first colors, the colored reference elements may be used to correct for local illumination conditions. By way of example, at step 1706, a processing device may correct the first image. In some embodiments, the processing device may use the first colored reference set in the image to determine local illumination conditions. The processing device may also determine chromatic properties of the first reference set, which it may do by directly analyzing the image itself, and/or by examining data containing chromatic property information of the first reference set. This data may be included within metadata of the image, or may be accessed by reading a machine-readable code (e.g., a scannable code attached to a reference set, which may be an instance of unique code 906). Based on the determined local illumination conditions, chromatic properties, and/or based on capturing parameters, the processing device may correct the image. Image correction may physically occur to an image, or it may simply occur through calculations without a physical alteration of the image. Some disclosed embodiments may include using the colored reference elements to determine the local illumination conditions and separately rectifying colors of the multiple segments of each wound based on the local illumination conditions. In some examples, step 1706 may be excluded from process 1700.

Continuing with the above implementation example, at step 1708, a processing device (e.g., a server 1610) may receive a second image. This image may be an image 1500*b*, which may have been captured using any image sensor, such as a camera associated with the smart phone 1604*a*, or, as illustrated, a tablet 1604*b*. As with image 1500*a*, image 1500*b* may include a plurality of wounds and a colorized surface, as described with respect to FIG. 15. In some embodiments, the second image may have been captured by an image sensor and/or received at the processing device at a threshold amount of time after a first image is captured and/or received (e.g., the second image is captured at least one day after a first image is captured).

Continuing with the implementation example, at step 1710, a processing device, which may be different from the processing device receiving the image at step 1708 (e.g., an image analysis unit connected to communications network 1606), may detect a second wound set (e.g., a wound or plurality of wounds) and/or a first colored reference set (e.g., colorized surface 1502*b*). For example, the second image may be analyzed and the second set of wounds may be detected in a similar fashion to the techniques described with respect to step 1704, the first image and the first set of wounds above. In some embodiments, a second wound set and/or a colored reference set may be detected based on portions of human skin separating wounds or separating a wound from a colored reference set. A second wound set may also be detected based on a comparison of the colorized reference elements to chromatic information of the wound set. In some embodiments, the processing device may determine a set of colors, orientation, shape, chromatic information, etc. of the second wound set.

Then, at step 1712, a processing device may correct the second image. This correction may be accomplished according to any combination of actions described above in connection with correction of the first image. For example, processing device may determine local illumination properties of the image, and may correct the image based on those properties. Continuing with this example, if the light quality causes a specific misperception of the known color reference elements, then the correction necessary for the color reference elements may be applied to a wound, thereby correcting a wound color. Some examples of techniques for such correction of the image are described above. In some examples, step 1712 may be excluded from process 1700.

At step 1714, a processing device may match at least one wound in the first wound set (e.g., a wound set in image 1500*a*) to at least one wound in the second wound set (e.g., a wound set in image 1500*b*). In some examples, a machine learning model may be trained using training examples to match wounds from pairs of wound sets, and the trained machine learning model may be used to analyze the first wound set and the second wound set to match at least one wound in the first wound set to at least one wound in the second wound set. An example of such training example may include a pair of wound sets, together with a matching of wounds between the two wound sets. For example, such wound set may include properties of the wounds, such as dimensions, tissue composition, relative position, appearance (for example, an image of the wound), etc., and the machine learning model may analyze these properties. In some examples, a machine learning model may be trained using training examples to match wounds from pairs of images, and the trained machine learning model may be used to analyze the first image (such as image 1500*a*) and the second image (such as image 1500*b*) to match at least one wound in the first image to at least one wound in the second image. Such training examples may include a pair of images, together with a matching of wounds between the two images, a portion of an image or portions of multiple images, color information associated with an image, and/or any other data capable of training a machine to match wounds.

In some embodiments, matching the wounds may include predicting an expected appearance of a wound (e.g., predicting an expected color, size, etc. of a wound in an image taken later in time than a first image). Disclosed embodiments may include determining a time difference between the first image and the second image. For example, predicting an expected appearance of a wound may involve determining a time difference between a capture time of a first image and a capture time of a second image, which may be accomplished by determining a time lapse between image capture. For example, a processing device may determine when an image was captured by reading a timestamp 1508*a*, and/or timestamp 1508*b*. In embodiments where a timestamp is superimposed on an image, the processing device may use optical character recognition to read the timestamp. In other embodiments, such as when a timestamp is embedded into an image or attached to it within metadata, the processing device may extract it from those sources. In some disclosed embodiments, the time difference between the first image and the second image may be determined automatically using metadata associated with the second image. For example, a processing device may determine the time difference automatically using metadata associated with the second image. In some disclosed embodiments, the time difference between the first image and the second image may be determined automatically by comparing metadata associated with the first image and metadata associated with the second image. This may be accomplished by a processing device.

Based on a time difference between images of a wound set, a processing device may determine an expected appearance of at least one wound. For example, data may be maintained in a data structure that maps a healing process of a wound based on wound characteristics. Alternatively, learning algorithms may be applied to a repository of wound images to identify wounds that most closely correspond to the first image, and thereby predict how the current wound is expected to heal over time. Since the time lapse is known for the first and second image, based on how other similar wounds of others have healed over time, the system can determine if the wound healing is progressing as expected, or if there appears to be an abnormality. Such progress may be based on any combination of a change in color of the wound, a reduction in size of the wound, a change in the shape of the wound, a change in the color of an outline of the wound, a change in the tissue composition of the wound, and/or non-wound-related characteristics, such as a patient's age, gender, health, genetics, skin type, or any other non-wound-related characteristic that might correlate to wound healing.

Disclosed embodiments may include predicting an expected appearance of each of the plurality of wounds in the second image based on the determined time difference and/or using the predicted expected appearance for matching each of the plurality of wounds in the second image to the plurality of wounds in the first image. By way of example, after a processing device has predicted the expected appearance of a wound in a second image, the processing device may use the predicted expected appearance to match at least one wound in a first image to at least one wound in the second image (e.g., matching each of a plurality of wounds in the second image to wounds of a plurality in the first image). In disclosed embodiments, the predicted expected appearance may be based on a type of each of the plurality of wounds. For example, a laceration is different in type from a burn, and therefore, the healing process for the wounds would be expected to be different. Indeed, there are many different types of wounds, ranging from chemical burns, sunburns, lacerations, abrasions, contusions, hematomas, punctures, and avulsions. Each has its own wound healing profile.

In some embodiments, the predicted expected appearance may be based not only on the type of a wound but also on its extent. For example, larger or deeper wounds would be expected to have a different healing process than small or shallower wounds.

In some cases, a wound may split into two or more wounds over time, and two or more wounds may be joint together into one wound over time. In some embodiments, a processing device may match two or more wounds in the first wound set (e.g., a wound set in image 1500*a*) to a single wound in the second wound set (e.g., a wound set in image 1500*b*), and/or may match a single wound in the first wound set (e.g., a wound set in image 1500*a*) to a plurality of wounds in the second wound set (e.g., a wound set in image 1500*b*). For example, two or more wounds in the first image (e.g. in image 1500*a*) may be joined together into a first wound in the second image (e.g. in image 1500*b*), and step 1714 may include matching the first wound in the second image to the two or more wounds in the first image. In another example, a first wound in the first image (e.g. in image 1500*a*) may split into two or more wounds in the second image (e.g. in image 1500*b*), and step 1714 may include matching the two or more wounds in the second image to the first wound in the first image. In some examples, a machine learning model may be trained using training examples to match a plurality of wounds in a one wound set with a single wound in another wound set, and the trained machine learning model may be used to analyze the first wound set and the second wound set to match a plurality of wounds in a first wound set with a single wound in a second wound set and/or to match a single wound in a first wound set with a plurality of wounds in a second wound set. Such training examples may include a pair of wound sets together with a matching of a plurality of wounds in one wound set with a single wound in the other wound set, a portion of an image or portions of multiple images, color information associated with an image, and/or any other data capable of training a machine to estimate. For example, such wound set may include properties of the wounds, such as dimensions, tissue composition, relative position, appearance (for example, an image of the wound), etc., and the machine learning model may analyze these properties. In some examples, a machine learning model may be trained using training examples to match a plurality of wounds in a one image with a single wound in another image, and the trained machine learning model may be used to analyze the first image (such as image 1500*a*) and the second image (such as image 1500*b*) to match a plurality of wounds in a first image with a single wound in a second image and/or to match a single wound in a first image with a plurality of wounds in a second image. An example of such training example may include a pair of images, together with a matching of a plurality of wounds in one image with a single wound in the other image.

Disclosed embodiments may include determining an indicator of the healing progress for each of the plurality of wounds based on changes between the first image and the second image. An indicator may be any displayed measure of wound progress, whether represented graphically, pictorially, textually, or otherwise. An indicator may provide a notification that a wound is healing faster or slower than expected; may advise of an expected time remaining until substantial healing is complete; may provide a pictorial or video time lapse indication of healing progress; may provide a warning of slow progress or regression or may include any other indicator that provides a sense of healing progress. In some embodiments, the predicted expected appearance may be based on image comparison with a repository of wound images, and a healing progress indicator may be provided for each of the plurality of wounds determined from previous images. In some embodiments, a healing progress indicator may also be used to update medical records. For example, a processing device may update personal electronic medical records with at least one healing progress indicator for a wound, which may be part of a plurality of wounds. Some disclosed embodiments may include updating personal electronic medical records with the indicator of the healing progress for each of the plurality of wounds.

In some embodiments, a processing device may use wound signatures to match a wound in one set to a wound in another set. A wound signature may include any unique characteristic that may distinguish one wound from another. Disclosed embodiments may include determining a wound signature based on visual appearance of the multiple segments for each of the plurality of wounds. In some embodiments, at least one wound signature may be based on at least one visual appearance of a segment of a wound. In yet other embodiments, multiple visual appearances of multiple segments of a wound may be used. In other words, a wound signature may encompass a combination of segments of a wound that uniquely differentiates it from other wounds (either uniquely from all wounds in the same image, or uniquely from all possible wounds). For example, a wound may have a particular combination of segments having different appearances (based on colors, shapes, sizes, tissue type, etc.) Disclosed embodiments may include using the wound signature for matching each of the plurality of wounds in the second image to the each of the plurality of wounds in the first image. For example, a combination of segments may form a wound signature, which a processing device may use to match each of a plurality of wounds in a second image to the each of the plurality of wounds in a first image. For example, a wound signature may be determined based on color distribution of multiple segments for each of a plurality of wounds. In some embodiments, a wound signature may be associated with ratios between areas of the multiple segments. In some embodiments, an auto-encoder may be used to generate wound signature of an image of a wound. Such auto-encoder may include a deep neural network trained using images of wounds.

Wound signatures may also be updated over time, which may improve accuracy of wound-matching. Disclosed embodiments may include updating the wound signature for each of the plurality of wounds based on visual appearance of the multiple segments as depicted in the second image.

For example, in some embodiments, a wound signature from a first image may be updated for at least one wound based on at least one visual appearance of at least one segment of a wound as depicted in a second image. While two images are discussed in this example, any number of images may be used to create accurate wound signatures. Moreover, while portions of the description refer to a first image and a second image, this disclosure contemplates that additional images may be captured and used to track wound healing progress over time.

At step 1716, a processing device may determine healing progress of at least one wound, which may be based on a change in appearance of the at least one wound between two images. For example, after matching one wound of a plurality of wounds in a first image to a wound in a plurality of wounds in a second image, the processing device may determine that a combination of color, dimensions, shape, tissue combination, condition of the peri-wound skin, etc., has changed with respect to the wound. These changes may be associated with a particular level of healing progress. For example, a processing device may determine that a size of a matched wound has shrunk and/or that a hue, value, and/or intensity of at least a segment of the wound has changed. Based on that determination, the processing device may establish that the wound has healing to a certain point of healing progression (75% fully healed, healing faster than expected, wound is infected, healing has stagnated, etc.) In some examples, a machine learning model may be trained using training examples to determine levels of healing progresses from pairs of images of a wound, and the machine learning model may be used to analyze the depiction of the wound in the first image and the depiction of the wound in the second image to determine the level of healing progress of the wound. An example of such training example may include a pair of images of a wound, together with a label indicating the level of healing progress of the wound. In some examples, a machine learning model may be trained using training examples to determine levels of healing progresses from pairs of image-related information records, and the trained machine learning model may be used to analyze image-related information based on the first image (such as image 1500*a*) and image-related information based on the second image (such as image 1500*b*) determine the level of healing progress of the wound. Such training examples may include a pair of image-related information records, together with a label indicating the level of healing progress of the wound, a portion of an image, color information associated with an image, and/or any other data capable of training a machine to determine a level of healing progress of a wound.

Disclosed embodiments may include using the first captured image, the second captured image, and additional captured images to create a video stream illustrating the healing progress for each of the plurality of wounds. By way of example, a processing device may generate a video illustrating healing progress of at least one wound. A first image of a wound, a second image of a wound, and possibly additional images, may be used to generate the video. Some embodiments may include generating artificial images as frames between the captured image frames in the generated video. These artificial images may be estimates of how the wound changed between capture of the first image and capture of the second image. The artificial images may enable a video playback where the first image morphs into the second image. Some embodiments may include using the colorized surface in the captured images to adjust at least one of orientation of the plurality of wounds and colors of the plurality of wounds in the video. For example, a processing device may use the chromatic information of the colorized surface to determine chromatic information of a plurality of wounds, which it may use to determine relative orientations and/or positions of wounds, which it may in turn use to adjust an orientation of a wound, or, in some cases, an orientation of the entire image. In addition, misperceptions of color by image capture device due to local lighting conditions, can be corrected in either video playback or in still images. Thus, a patient's medical record may include color-corrected video or images.

Disclosed embodiments may include determining that the healing progress of at least one of the plurality of wounds is below a healing threshold and/or generating a treatment suggestion for improving healing of the at least one wound. By way of example, a healing threshold may comprise a combination of chromatic properties, shape, size, and/or other attributes expected for at least one segment of a wound.

Based on the determination of the healing progress being below a threshold, the processing device may generate and/or provide recommended treatment steps (i.e., suggestions) to a user (e.g., user 1602*a*, user 1602*b*, etc.), who may be the patient or who may be a healthcare professional. For example, the processing device may recommend the application of a particular antibiotic to a wound, reduction of exposure of a wound to sunlight, increasing the amount of a particular nutrient in a user's diet, etc.

Aspects of this disclosure may relate to a method for updating an electronic medical record based on patient generated image data. Some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using may differing instrumentalities.

Consistent with disclosed embodiments, a method may involve physically providing to a patient a test kit. A test kit, as used herein, may include any materials configured to determining a characteristic of a patient. For example, a test kit may contain material to enable one or more of monitoring, measuring, analyzing, or capturing of information reflective of a characteristic of a patient. The test kit may be physically provided to the patient. Physical provisioning of the test kit may occur in many differing ways. For example, a healthcare provider or an agent of a healthcare provider might transmit the test kit to the patient by post, private carrier, or by physically delivering the test kit to a location of the patient, be it at home, office, hospital, or any other location where the patient may be located. Alternatively, the test kit may be provided by inviting the patient to a location where the test kit may be picked up, or by providing the test kit to the patient during a scheduled or unscheduled appointment, such as with a doctor, at a clinic, or in any other facility where the patient may be located. Alternatively, providing the test kit to the patient may involve the use of an intermediary, such as a caregiver or agent of the patient (i.e., providing the test kit to an intermediary, constitutes providing the test kit to the patient, consistent with usage herein), a delivery service, and so forth. Thus, for purposes of this disclosure, a test kit is provided to a patient if the test kit is conveyed directly to the patient, or if it is provided to an agent of the patient, to enable the test kit to be used with the patient.

While a test kit may be provided in a single package or other conveyance, the test kit may also be provided in a hybrid manner in that elements of the kit may be provided at different times and/or through differing channels. For example, an electronic element of a kit may be transmitted electronically to the patient while a physical component may be transmitted physically. The manner of transmission may not be critical, so long as the patient is enabled to receive the test kit.

Some aspects of this disclosure may involve sending to the patient a verification code. A verification code may be physical and/or electronic, and may be any mechanism that enables a receiver to verify that received information originates from an intended source. Although referred to in the singular, a verification code may have multiple components, and may include more than one step, form or level of authorization. The code might be visual, in the form of a bar code, a QR code, or any other graphical form of code. The code may also be alphanumeric. Alternatively, the code could be fully electronic to enable verification between multiple pieces of electronics without direct user involvement. Thus, the code may be contained within a physical package sent to the patient, or could be electronically transmitted to and/or between a device associated with the patient and another entity.

The verification code may be sent to a patient via any communication channel such as an email, text or SMS message, phone call, mail, visual message, audible message, or any other communication channel. The verification code may be electronically transmitted to the mobile communications device. The transmission of the verification code may take place over any wired or wireless communication channel. For instance, the code may be transmitted over a PAN, LAN, WLAN, CAN, MAN, WAN, SAN, POLAN, EPN, VPN, cellular network, or any combination thereof or any other network capable of information transmission.

If physically provided with the test kit, the verification code may be printed on the kit packaging or within the kit, or may be indirectly provided in the kit, such as by providing an address of an electronic link through which the verification code may be obtained or electronically accessed. Thus, the code may be included with written instructions of the kit, as an image within the kit, on a separate item in the kit, or through any other electronic or physical means. The verification code may be machine readable.

Embodiments of the disclosure may also involve providing instructions to the patient to access, via a mobile communications device, an application for using the mobile communications device to capture a medical image. Instructions may be provided through one or more of printed instructions in the kit, by providing a link to the patient (or an agent of the patient) to electronically access the instructions, by providing the instructions through an app resident on a mobile communications device on the patient side, or on a server side, remote from the patient side, or through any other medium or channel that provides instructions for conducting a test. Again, reference to access by the patient alternatively includes providing access to one or more of the patient or an agent (e.g., assistant or administrator) associated with the patient.

As previously discussed, the mobile communications device can be any device with communications capabilities that enables transmission of image-related information. The mobile communications device may be enabled to capture a medical image. A medical image can be any image used for medical purposes. For example, it can be an image of a reaction to a particular test, a biological response, an anatomical image, or an image of a wound or a condition. Other examples of medical images are described above. A device may be enabled to capture a medical image if it includes an integrated image sensor, or if it has the capability to pair with a device that includes an image sensor. For example, a mobile phone or tablet may integrate an image sensor with a transmission component. Alternatively, a non-networked camera paired with a PC or other networked device may serve as a mobile communications device. In another example, a wearable device may include a camera and a transmission component.

Embodiments consistent with this disclosure may also involve enabling analysis of image-related data to determine an insufficiency of the image for medical examination. Enabling analysis may involve providing an app to the mobile communications device to perform image analysis on the mobile communications itself. Alternatively or in addition, the medical image may be transmitted via a network to a remote location where the analysis may take place. Thus, enabling analysis may involve one or more of providing an app that examines the medical image, enabling transmission of the medical image to a location where the examination may take place, or undertaking the medical image examination. The image-related data for examination may include the image itself, a subset of the image, or data derived from the image. Data derived from the image may include, for example, information about local illumination conditions, contrast, clarity, subject matter, or any other image characteristic or image-related information that may enable a determination of whether the image is sufficient for its intended purpose. If the image-related data is determined to be inadequate for its intended purpose, it may be deemed "insufficient." For example, a machine learning model may be trained using training examples to determine whether image-related data is sufficient for a particular purpose, and the trained machine learning model may be used to analyze the image-related data to determine whether it is sufficient for the intended purpose. An example of such training example may include image-related together with a label indicating whether the image-related data is sufficient for a particular purpose.

The extent and type of analysis may depend on a nature of an associated test. At a minimum, the analysis may be used to determine whether the image is sufficient for accomplishing the purposes of the particular test (e.g., determining whether the image contains sufficient information to enable meaningful medical examination).

Embodiments consistent with the disclosure may involve enabling display on the mobile communications device of a message indicative of the insufficiency of the image. Specifically, if the image fails to meet an acceptable standard for medical analysis, a message may be displayed, via the mobile communications device indicating the insufficiency. The message may be visual and/or audible. For example, the message may simply indicate that the image was insufficient, and/or it may direct a user to retake the image. As used herein, a message may be considered displayed on a device if the message is either visually or audibly presented via the device.

Embodiments of the disclosure may also involve, in response to the display of the message indicative of the insufficiency of the image, receiving a new image from the patient. The new image may be an attempt by the patient or an agent of the patient to provide an image that is of a level acceptable for medical examination. As with the original image, the new image may contain all or part of a captured image, or may contain data characterizing the actual captured image, each of which is considered a receipt of a new image, for purposes of this disclosure. The new image may be received in the same or different manner from the original image. If the analysis occurs locally, the image, or information characterizing the image may be received by a local processor. If the analysis occurs remotely, the new image or information characterizing the new image may be received via a network transmission.

Embodiments consistent with this disclosure may involve receiving the verification code from the patient. The verification code, in any of the forms described earlier, may be received by an app locally associated with a mobile communications device or may be received remotely on a server or other equipment. Regardless of how or where received, the verification code may serve to confirm that the new image originated from an intended source (e.g., the patient or an agent associated with the patient). In this way, the verification code may be used to verify that the new image was received from the patient.

Consistent with this disclosure, embodiments may involve, for example upon verification, automatically sending a notification to a healthcare provider for updating an electronic medical record of the patient with data associated with the new image. The notification may include one or more of a computer readable message or a machine readable message. For example, the notification may include computer readable patient identifying information together with either the new image itself, a portion of the image itself, data characterizing the new image, and/or data based on an analysis of the new image (any and all of which is considered a new image for purposes of this disclosure). The notification may be in a form that enables a recipient system to automatically update the patient's medical record with the new image, or which enables the record to be updated with limited human intervention (e.g., a human verification prior to update.) Alternatively, the notification may include human readable data, identifying the patient and enabling a human (such as an agent of a healthcare provider or insurance company) to update an electronic medical record. In another example, the notification may be sent to a healthcare provider together with information based on the verification code, and the verification may occur at the healthcare provider using the received information based on the verification code. Further, after the healthcare provider successfully verified (using the received information based on the verification code) that the notification includes information received from the patient, the healthcare provider may update an electronic medical record of the patient based on the received data.

Figure 21:
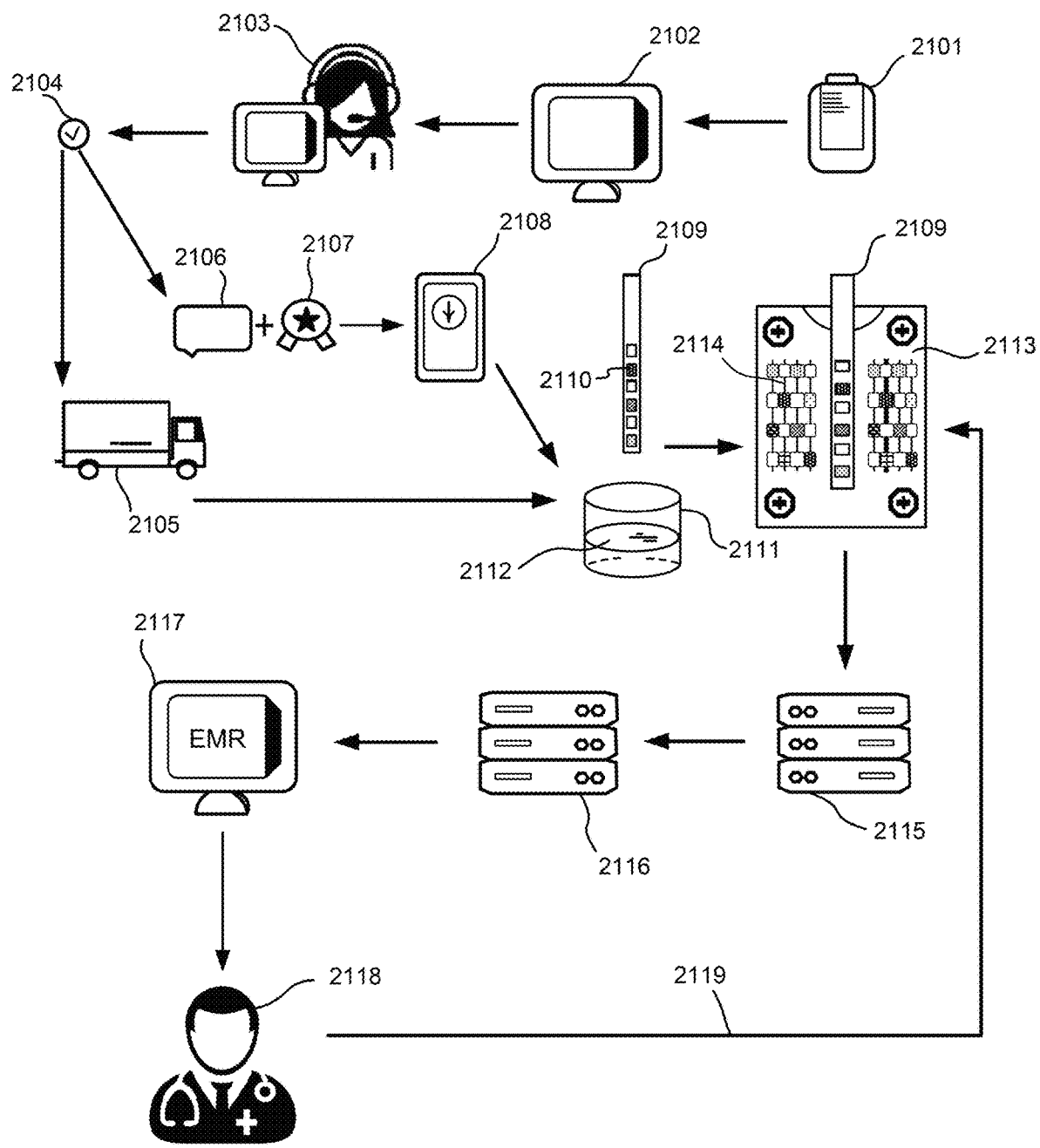
FIG. 21 illustrates a schematic representation of a method for updating an electronic medical record (EMR) based on patient generated image data, consistent with some exemplary aspects of one embodiment of the disclosure.

While the features previously described are not limited to a particular structure or additional steps, by way of example only, FIG. 21 is a schematic illustration of a method for updating an electronic medical record (EMR) based on patient generated image data. A list of eligible patients 2101 and details of the eligible patients may be uploaded into a patient portal 2102. A local modality team 2103 may be charged with a task of confirming that patient consent is received 2104, in accordance with either policy or law. In some instances, policy or law may not require consent, and if not, this step may be omitted. Next, a medical test kit may be delivered to the patient, as represented by node 2105. Simultaneously, before, or after, a verification code may be sent to the patient. The verification code may take the form of one or more of a text, an SMS message 2106, a token 2107, or any other electronic or physical mechanism for authenticating a transmission. The patient may download an application onto their corresponding mobile communications device 2108. As previously described, the mobile communications device may take the form of a phone, mobile phone, smart phone, smart watch, smart glasses, tablet, laptop, personal computer, PDA, or any device or combination of devices that may allow for communication between a patient and the system (such as mobile communications device 115, mobile communications device 1604a, mobile communications device 1803, mobile communications device 2200, and so forth). The application may guide a patient through the medical testing procedure.

The medical test kit delivered to the patient may be configured for monitoring, measuring, analyzing, or capturing information reflective of a characteristic of a patient. For example, if used for chemically analyzing a biological material, the test kit may include a container configured to contain, for example, a biological fluid; a dipstick including a plurality of test reagent pads thereon for measuring differing properties of the biological fluid; and a colorized surface including a dipstick placement region in proximity to a plurality of colored reference elements. For example, a medical test kit may include a dipstick 2109. The dipstick 2109 may include one or a plurality of reagent pads 2110. The one or plurality of reagent pads 2110 may be configured to change color when in contact with a specific analyte, characteristic or parameter. The reagent pads 2110 may include, for example, a plurality of different reagents to react with different analytes, components, characteristics, parameters, etc. found within biological fluid. Biological fluid may include sweat, urine, blood, stool, breast milk, saliva, interstitial fluid, or any other biological fluid or sample. The medical test kit may also include a container or receptacle 2111 and colorized surface 2113. The colorized surface 2113 may include a dipstick placement region in proximity to a plurality of colored reference elements 2114. The container or receptacle 2111 may be of any size, shape, or construction suitable for receiving or containing a desired biological fluid 2112. The medical test kit may also include additional components to aid in the collection of a biological fluid. For example, an additional component may include a needle, lancet, or other means to allow for the piercing or puncturing of a skin surface in order to collect a blood sample. One example of such medical test kit may include urinalysis kit 1200 described above.

Test reagent pads 2110 may be configured for measuring differing properties of the biological fluid. For example, if associated with a urine test, the dipstick may include a first test reagent pad for measuring a first property associated with albumin concentration and a second test reagent pad for measuring a second property associated with creatinine concentration. Other examples of dipsticks and/or reagent pads are described above. A plurality of reagent pads may be configured to measure a plurality of different analytes, concentrations, components, compounds, etc. as desired. Moreover, a first reagent pad may be configured to react with a first biological fluid, and a second reagent pad may be configured to react with a second biological fluid. The dipstick may include at least two of: a first test reagent pad for measuring a first property associated with leucocytes in urine, a second test reagent pad for measuring a second property associated with blood in urine, a third test reagent pad for measuring a third property associated with nitrite in urine, a fourth test reagent pad for measuring a property associated with a urinary tract infection, and a fifth test reagent pad for measuring a property associated with white blood cells in urine. It is understood that the test kit may include any number of test reagent pads 2110 and may be configured for measuring a plurality of different analytes, parameters, or characteristics of a biological fluid, or a plurality of biological fluids.

The application associated with the mobile communications device 2108 may guide the patient through the medical test procedure. One example of such application may include app 1804. In other example, such application may implement all or parts of process 700, of process 800, of process 1400, of process 1700, of process 2000, and so forth. In some examples, the application may prompt a patient to fill receptacle 2111 with a biological fluid 2112 such as urine. It is noted however, that other biological fluids may be used with various medical test kits. For example, test kits may be designed for measuring an analyte, concentration, property, parameter, characteristic or other feature associated with blood, urine, saliva, sweat, stool, interstitial fluid or any other biological fluid or sample. The application may then direct the patient to blot the dipstick 2109 and place it adjacent to colorized surface 2113. Thereafter, the instructions may guide the user to use mobile communications device 2108 to capture an image of the dipstick 2109 and colorized surface 2113. An analysis of image-related data associated with the image may be performed to determine insufficiency of the image for medical examination. For example, the image may not include the entire colorized surface 2113 or entire dipstick 2109, the image may include a glare or other local lighting deficiency rendering some or all of the image obscured, blurry, lacking sufficient contrast, or otherwise failing to capture sufficient information to enable completion of the test. In the event that a determination has been made of insufficiency, the display on the mobile communications device may display a message indicative of the insufficiency of the image. The user may then be instructed to recapture the image (e.g., provide a new image).

When a sufficient image has been captured by the mobile communications device 2108, the image and corresponding image-related data may be uploaded to the server 2115. The image-related data may include at least one of image clarity, image illumination, and a time of capture of the medical image. Image-related data may also include geographic information, weather information, pixel information, camera or image sensor information, an analysis of the image or a portion thereof, compression data, data related to transmitting the image, or any other data or information related to the medical image or capturing of the medical image. Server 2115 may include software and/or hardware to allow for analysis of the image or image-related data to generate a test result. The test result may then be then transmitted to server 2116. Servers 2115 and 2116 may be one or more of a plurality of remote or local servers, or one or more of a plurality of cloud-based servers. Server 2116 may be associated with a healthcare provider or healthcare professional. Server 2116 may also include an electronic medical record for the patient which may be updated to include the test result. The updated electronic medical record 2117 may be displayed for healthcare professional 2118. Healthcare professional 2118 may review medical record 2117 and test result. After review, the healthcare professional 2118 may issue a follow up test 2119.

Figure 22A:
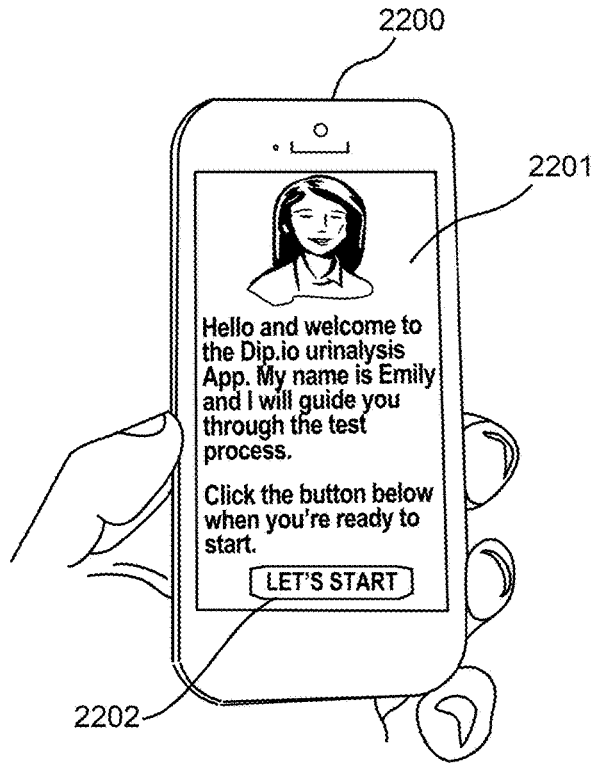
FIGS. 22A-22D illustrate an example user interface in accordance with one exemplary aspect of one embodiment of the disclosure.
Figure 22B:
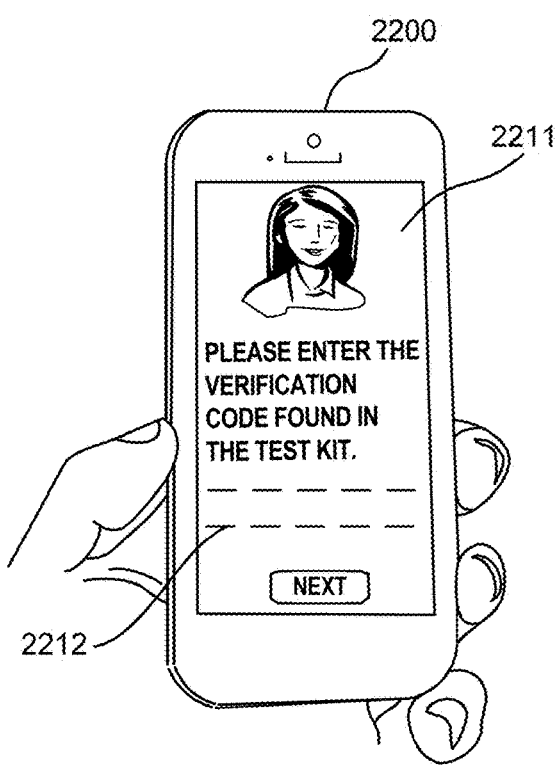

FIG. 22A shows an example mobile communications device 2200. Mobile communications device 2200 may include an application to help guide the patient through the medical testing procedure. Some examples of mobile communications device 2200 may include any one of mobile communications device 115, mobile communications device 1604a, mobile communications device 1803, a smartphone, a tablet, a wearable computer, and so forth. As illustrated, on display 2201 of mobile communications device 2200, an introductory message may be provided to the patient. To begin a medical testing procedure, the patient may be prompted to press the "Let's Start" button 2202. As illustrated in FIG. 22B, the mobile communications device 2200 may prompt the patient to enter a verification code in field 2212. This ensures for secure communication between a specific patient, or agent of the patient, and one or more end users. Alternatively, the application could instruct the user to scan a code provided in the test kit or separately sent to the user.

Figure 22C:
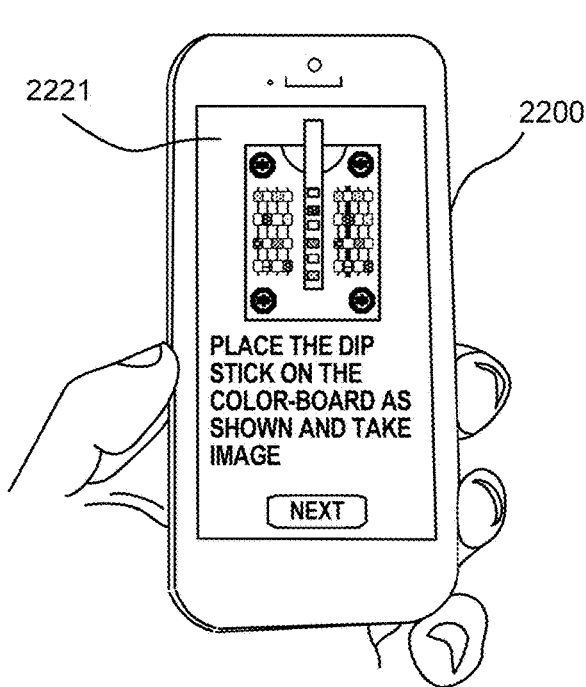
Figure 22D:

By way of an example, as shown in FIG. 22C, the application may cause instructions to appear on display 2221 for undertaking a medical test. For example, FIG. 22C may contain graphics illustrating how to place a dipstick on the color-board or colorized surface prior to obtaining an image thereof. Upon successful completion of the testing procedure, display 2231 in FIG. 22D may indicate that the test results have been successfully uploaded to the electronic medical record. The forgoing instruction examples are for illustration purposes only. Step-by-step instructions with many more illustrations, diagrams, animations, images or audible instructions may be provided to carefully guide the user through a testing process.

Figure 23:
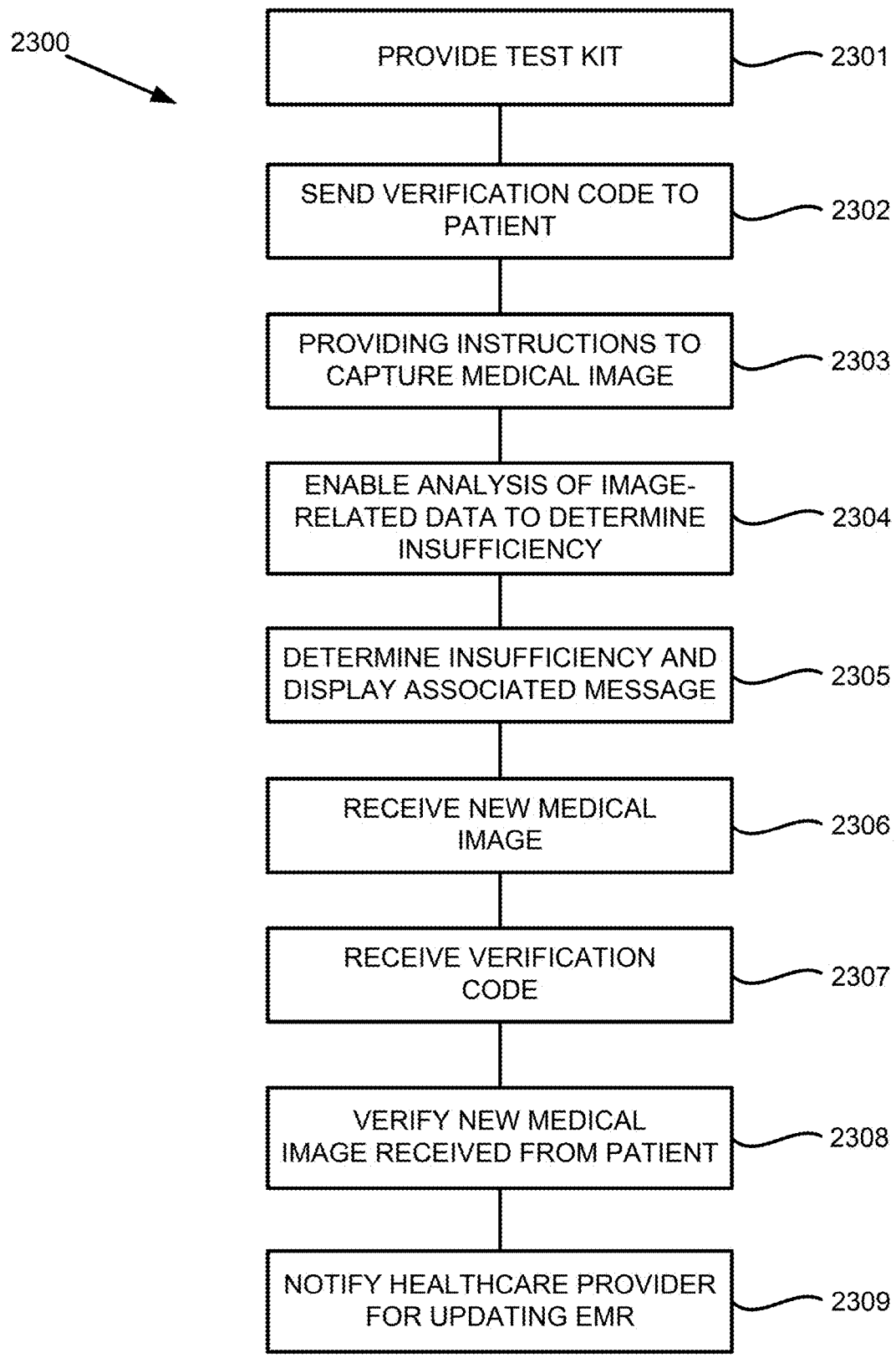
FIG. 23 illustrates a flowchart in accordance with one exemplary aspect of an embodiment of the disclosure.

FIG. 23 illustrates one exemplary method 2300 for updating an electronic medical record based on patient generated data. The method may involve physically providing to a patient a test kit at step 2301. Physically providing a test kit may include any means for allowing a patient to access a test kit, for example as described above. For example, a patient may receive a test kit from a healthcare provider's office, through mail or a delivery service, from a retail location, or any other means allowing for collection of or access to a test kit. Test kits may be delivered to a specific patient at recurring intervals, when instructed by a healthcare provider or insurance provider, or when requested by the patient. Additionally, test kits may be delivered to one or more patients as the result of a health preventative program.

Once a patient is in custody of a test kit, instructions may be provided to the patient to capture a medical image. An application associated with a mobile communications device may assist the patient in capturing the medical image of, for example, medical test results. Some examples of such instructions are described above. In some examples, the instructions may include guidance on how to perform the medical test using materials provided in the test kit. This may occur through an application running on the mobile communications device or otherwise accessible through the mobile communications device that may provide directions, instructions or steps of performing the medical test. The directions, instructions or steps may be visually presented to the patient in the form of text, images, videos, or animations. Additionally, the directions, instructions or steps may be presented audibly to a patient in the form of speech, sound bites, or other prompts. Additionally, the application may include an interactive feature which may respond to a prompt or question of the patient. The instructions provided to the patient may include one or more, or at least two of opening the test kit, expanding a collapsed measuring cup, dipping a dipstick, blotting the dipstick, placing the dipstick on a colorized test surface; capturing an image of the dipstick on the colorized test surface, and recapturing the image of the dipstick on the colorized test surface. The instructions provided to the patient may be sequential and the instructions may include directing a user to complete at least one activity during a predefined time window after completion of a previous activity. For example, the instructions may direct the patient to place the dipstick in the biological fluid for a specified time period (such as a time period between 50 to 65 seconds), and may then instruct the patient that an image of the dipstick needs to be captured at a specified time window (for example, between 2 minutes to 3 minutes after the dipstick is placed on a colorized test surface, between 2 minutes to 3 minutes after the dipstick is dipped, between 2 minutes to 3 minutes after the dipstick is blotted, and so forth).

The method may further include sending to the patient a verification code, as depicted in step 2302 of FIG. 23. The order and manner of code transmission may be insignificant in that it could be physically transmitted to the patient with the test kit or transmitted electronically to the patient before, after, or simultaneously with physical transmission of the test kit. The verification code may include more than one step or level of authorization, and may take a plurality of forms. As previously discussed, so long as the verification code is able to confirm that transmitted medical information is authentic (e.g., originates from the intended source), the verification code may take any form and may be received in any manner. The verification code may also be used to verify that test kit usage does not exceed a prescribed usage limit. For example, to avoid a reading of contaminated results or results distorted by a test kit's exposure to prior biological materials, each test kit may be designed for limited use (e.g., single use), and the verification code may be used to ensure that no test kit us used beyond its prescribed limit. In such situations, each verification code may be unique to a particular instance of a test kit.

The method of FIG. 23 may include providing instructions to the patient to access, via a mobile communications device, an application for using the mobile communications device to capture a medical image. The instructions may be included as part of the test kit, or may be transmitted to the patient apart from the test kit. The application may direct the user and guide the user through the process of capturing a medical image. For example, the instruction may guide the patient in capturing a medical image at step 2303 using a mobile communications device with an integrated image sensor, or which is otherwise associated with an image sensor. In one aspect, the medical image may include an image of a dipstick and corresponding reagents proximate or adjacent to a surface containing colorized reference elements. In another aspect, the image may include one or more skin features proximate to or near a colorized surface. The medical image may be uploaded or transmitted to an analysis unit. In one aspect, the analysis unit may be a remote server or processor that analyses the medial image and/or image-related data to determine, in a first instance, sufficiency of the image. In another aspect, the analysis unit may be a processor or group of processors located within the mobile communications device. Thus, enabling an analysis of image related data may include providing an application for use by a mobile communications device, or it may involve providing the analysis function through the provision of software running on a remote server. Enabling of analysis may alternatively be accomplished by providing any other structure or functionality where the analysis may occur.

The analysis of image-related data may include determining an insufficiency of the image for medical examination. At step 2304 analysis of image-related data may be enabled. The analysis may include analyzing the image or a portion of the image, comparing the image or a portion of the image to a threshold, or any calculation or measurement that can be used to determine if an image is suitable for medical examination. In one aspect, enabling analysis includes providing the patient with access to the application, either by providing software to the mobile communications device or by enabling the mobile communications device to communicate with a remote server where the analysis occurs. Some examples of an analysis of image-related data are described above.

In step 2305, an insufficiency of the image may be determined for one or more of the reasons previously discussed. Thereafter, the method may enable display of an associated message to the user. The message may include one, or a plurality of messages in one or more of text, graphics, animation, audio, video, etc. The message indicative of the insufficiency of the image may include an explanation of why the image is insufficient and may point out specific features that render the image insufficient. For example, the message may state that the entire colorized surface is not shown, or that the image is too blurry. Alternatively, the message may simply instruct the user to retake the image. Enabling display of the message indicative of the insufficiency of the image may include one or more of sending data to a display in order to cause the message to appear, or may simply involve providing the application that enables such functionality. Enabling display of the message indicative of the insufficiency of the image may also include transmitting data associated with the message to the mobile communications device over a wireless network. Displaying the message may include any visual or audio display. After displaying the message indicative of the insufficiency of the image, modified instructions for capturing the new image may be provided, wherein the instructions may be modified to account for the cause of prior insufficiency of the image. For example, the application may prompt a user to move the dipstick to a new position before capturing a new image, alter the field of view to capture the entire colorized surface, or alter a lighting condition. Additionally, the application may also request the user hold the image sensor steady while capturing an image, or prompt the user to perform other tasks to ensure collection of an image and image-data suitable for analysis.

In step 2306, an exemplary method may include, in response to the display of the message indicative of the insufficiency of the image, receiving a new image from the patient. The new image may similarly be analyzed for sufficiency in much the same way as the original image was analyzed.

At one or more times during the process of FIG. 23, the method may include receiving the verification code from the patient, and using the verification code to verify that the new image was received from the patient. For simplicity of discussion, verification code receipt is illustrated once at step 2307. However, the verification may instead (or additionally) have been conducted earlier in the process, essentially verifying the entire session or appropriate portions thereof. After receiving the verification code, it may be used to verify that the new image was received from the patient. This may occur, for example, by transmitting the code to a remote server that looks up the code and confirms that the code is in fact assigned to the associated patient.

With some medical tests, a time lapse between conducting of the test and image capture may be material. If so, and if the image capture failed to occur within a prescribed time window regulated by the application, a prompt may be displayed to a patient requesting a new image. In one example, the user may be instructed to rerun the complete test before capturing the new image. In other instances, the user may be instructed to resubmit or retransmit previously captured images. An entirely new image may be required when the insufficiency is the result of a portion of the test kit missing from the image, or the image being too noisy or blurry. However, in the event where the image was complete but did not transfer entirely, a resubmission of the same image may be sufficient.

If the image is complete and sufficient, the method may include analyzing the new image, wherein the new image depicts a colorized surface in proximity to a medical analysis region, and the colorized surface enables determining of colors of the medical analysis region. For example, the new image may be analyzed as described above, for example in relation to process 700 and/or process 800 and/or process 1700.

Upon verification that a new image has been received from a patient, a notification may be automatically sent to a healthcare provider in step 2309 for updating an electronic medical record of the patient with data associated with the new image. If the healthcare provider happens to be the entity who received the new image in the first instance, and the healthcare provider also maintains the EMR of the particular patient, then sending the notification may occur internally. If the patient's EMR is maintained by a healthcare provider other than the entity who initially received the updated image, the notification may be sent via a network or any other suitable means to the EMR-maintaining healthcare provider for updating the patient's EMR. The notification may take the form of a notice advising the healthcare provider that new results are available upon request, or the notification may include indicia of the results, including one or more of a conclusion (e.g., positive or negative for a condition), actual numerical results of a test; the image itself, and/or additional information pertinent to the medical record.

In accordance with one aspect of the invention, a non-transitory computer readable medium for updating an electronic medical record based on patient-captured image data may contain instructions that when executed by at least one processor cause the at least one processor to perform a method in accordance with aspects set forth in accordance with FIGS. 21-23 and discussed above.

The method may include accessing a record of a verification code associated with a home testing kit sent to a patient. A unique verification code may be associated with each individual home testing kit, or a plurality of testing kits. The verification code may be recorded in any manner such as in memory or as a hard copy. Memory may include digital or analog memory. Memory may include Random Access Memory (RAM) devices, NOR or NAND flash memory devices, Read Only Memory (ROM) devices, etc. The verification code may be accessed manually, or over any wired or wireless network or communication channel. For instance, accessing may include connecting to a remote server, or may include connection from a mobile communications device over a cellular network.

The method may include receiving a captured medical image of the patient via a wireless network. The medical image of the patient may include a feature or characteristic of the patient, or may include an image of a test kit or portion thereof having been prepared by the patient. A feature or characteristic may include a legion, mole, freckle, scar, injury, burn or other feature or characteristic of a body surface.

The method may include analyzing the medical image to determine an insufficiency of the image for medical examination. The analysis may be performed locally or remotely. For instance, if a patient captures a medical image on a mobile communications device, the mobile communications device may determine if the captured image is sufficient. Additionally, the analysis may be performed remotely if the medical image is transferred to a remote location. The determination of insufficiency may include an analysis of pixels, color, light, whether or not an image includes a complete subject, or any other determination that may indicate an image is unsuitable.

The method may include sending at least one message indicative of the insufficiency of the image, wherein the at least one message includes a guidance to capture a new image. The at least one message may include a text or SMS message, an email, a video, or any other visual display. Additionally, the at least one message may include an audible prompt or sound bite. The at least one message may include a plurality of messages, or a series of messages to aid a patient in capturing a new image.

The method may include wirelessly receiving the new image from the patient along with the verification code. Wirelessly receiving may involve communications over any wireless network or system, such as WIFI, cellular, radio frequency, etc. The verification code may be received from the patient as an SMS or text message, numerical input, image, audio call, email, or via any other type of communication.

The method may include using the verification code to verify that the new image was received from the patient. Upon verification, the method may include automatically sending a notification to a healthcare provider for updating an electronic medical record of the patient with data associated with the new image. The notification may be sent via an automated messaging system, via a phone call, an SMS or text message, an email, or any other method or system to provide notification to a healthcare provider. The notification may include a test result or results associated with a medical test performed by the patient, images or image-data from the medical test, a notification that a test was performed, or any other prompt or message which may be sent to a healthcare provider to indicate an update to an electronic medical record may be performed.

In accordance with one aspect of the invention, a system for updating an electronic medical record based on patient-captured image data is disclosed. The system may be configured to perform methods consistent with aspects set forth in accordance with FIGS. 21-23 and discussed above. The system may include at least one processor. The at least one processor may be any of the devices or combinations of devices described herein. Those devices may be embodied within one or more of a personal computer, laptop computer, desktop computer, tablet computer, notebooks, mobile phone, a terminal, a kiosk, PDA, a cloud-based computing device, a remote server or servers, smart phone, smart watch, smart device, or any other system allowing for processing of information.

In some embodiments, the at least one processor may be located remote from a mobile communications device of a patient and perform functionality based on data received from the mobile communications device of the patient. For example, the processor may be configured to access a record of a verification code associated with a home testing kit sent to a patient. A unique verification code may be associated with each individual home testing kit, or a plurality of home testing kits. For example, each testing kit may have its own unique code that may be assigned to a particular patient. Alternatively, a group of test kits may share a code that may be assigned to a group of individuals receiving a common form of test kit.

The processor may be configured to receive a captured medical image of the patient via a wireless network, as previously discussed. The medical image of the patient may include a feature or characteristic of the patient, or may include an image of a test kit or a portion thereof having been prepared by the patient. A feature or characteristic may include a legion, mole, freckle, scar, injury, burn or other feature or characteristic of a body surface.

The processor may be configured to analyze the medical image to determine an insufficiency of the image for medical examination. Although the analysis may be performed remote from the mobile communications device that sent the medical image, some or all of the analysis may be performed locally on the mobile communications device. For instance, if a patient captures a medical image on a mobile communications device, the mobile communications device may determine if the captured image is sufficient, or at least meets a minimum threshold. Further analysis on a remote server may establish that the image is nevertheless insufficient. The determination of insufficiency may be based on analysis of pixels, color, light, whether or not an image includes a complete subject, or any other determination that may indicate an image is unsuitable.

The processor may be configured to send at least one message indicative of the insufficiency of the image, wherein the at least one message includes a guidance to capture a new image. For example, if the message is sent to the mobile communications device, the patient or agent of the patient may use the mobile communications device to obtain and transfer a new image to the remote processor. The at least one message may include a text or SMS message, an email, a video, or any other visual display. Additionally, the at least one message may include an audible prompt or sound bite. The at least one message may include a plurality of messages, or a series of messages to aid a patient in capturing a new image.

The processor may be configured to wirelessly receive the new image from the patient as well as the verification code. Wirelessly receiving may involve communications over any wireless network or system, such as WIFI, cellular, radio frequency, or any other communication channel as discussed above.

The processor may also be configured to use the verification code to verify that the new image was received from the patient; and upon verification, automatically send a notification to a healthcare provider for updating an electronic medical record of the patient with data associated with the new image, as discussed previously.

Aspects of this disclosure may relate to medical testing, including methods, systems, devices, and computer readable media. For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve receiving from a healthcare provider information identifying a plurality of individuals associated with a first insurance status. A healthcare provider may include any physician, doctor, nurse, surgeon, agent of a physician, hospital, clinic, insurance company, public health consultant, or any individual, group, organization or entity having an interest in healthcare or providing health services. A plurality of individuals may include individuals of the general population, a subset of the population, individuals having a pre-diagnosed or pre-existing condition, or any person or animal that may be in need of a medical test or procedure. Insurance status may include any status based on a diagnosis, an insurance claim, benefits limits, cost or price of coverage, provider information or any status related to health or healthcare. Any information related to health or healthcare may be utilized in determining or identifying an insurance status. For example, insurance coverage limits may differ between the first insurance status and the second insurance status.

Aspects of this disclosure may involve delivering home testing kits to the plurality of individuals. Some examples of such delivery are described above in relation to method 2300. The testing kits, or test kit, may include any number of materials configured to determine a characteristic or feature of an individual. A home testing kit may include elements to enable monitoring, measuring, analyzing, or capturing of information reflective of one or more characteristics or features of a patient. For example, the test kits may allow for the determination of one or more of an analyte, compound, component, composition or property of or found within a biological fluid. The home testing kits may include one or more cups, receptacles or pads configured to hold or extract one or more biological fluids. The kits may include one or more reagents configured to react with one or more analytes, compounds, components, compositions, features or chemicals found within a biological fluid. The reagents may be carried or embodied by one or more of a dipstick, a pad, a sheet, a receptacle, or any means to support or hold a reagent. One additional example of such kit may include urinalysis kit 1200.

Each home testing kit may include a colorized surface including a plurality of colored reference elements. The colorized surface may include one or more colors, hues, shades, shapes, indicia or features that may be used for providing a reference during the use of a test kit. The colorized surface may take any form or shape, and may be made of any material capable of supporting at least one colored reference element, or being printed on to include at least one colored reference element. The colorized surface may also be impregnated with one or more colors, hues, shades, shapes, indicia or features. The reference elements may be applied, impregnated, printed, attached or affixed in any manner.

The term "home testing kit," is intended to be interpreted broadly as a kit that may be used in the home, but also a kit that could be used in other locations such as clinics, doctors' offices, nursing homes, convalescent centers, and other locations where a patient might visit or be located.

Some aspects of this disclosure may involve receiving electronically from mobile communications devices of at least some of the plurality of individuals, medical image information corresponding to a medical analysis region in proximity to the colorized surface. Mobile communications devices may include any device with communications capabilities that enables transmission of image-related information. The mobile communications device may be enabled to transmit a medical image or data related to a medical image. A device may be enabled to capture a medical image if it includes an integrated image sensor, if it has the capability to pair with a device that includes an image sensor, or if it has the ability to otherwise receive medical image information from another source for transmission. For example, a mobile phone or tablet may integrate an image sensor with a transmission component. Alternatively, a non-networked camera paired with a PC or other networked device may serve as a mobile communications device. The electronic transmission may take place over any wired or wireless communication channel and may be performed by any method allowing for moving data or information from one location to another. The transmission may even be performed by the transferring of data with a removable memory from one device to another. A medical image may be any image used for medical purposes. For example, such a medical image may include an image of a reaction to a particular test, an image of a biological response, an anatomical image, or an image of a wound or a condition. Medical image information may include an image or other image-related data, metadata, or information obtainable from a medical image. The medical image information may reflect a reaction or change associated any analyte, characteristic, composition, component, feature, parameter, etc. of any biological fluid. Additionally, the medical image information may reflect information about a skin or body feature, such as a size, shape, color, healing progress, infection, benign, cancerous, pre-cancerous, etc. or any other information obtainable from data, metadata, or information related to an image. A medical analysis region may include any portion of a home testing kit, any portion of a patient, or any other element that may allow for a determination or diagnosis. For example, a medical analysis region may include one or more of a dipstick, a portion of the dipstick including one or more test reagent pads, a skin feature, or skin surface. A medical analysis region may be in proximity to the colorized surface during a portion of the testing procedure. In proximity includes being, near, adjacent, next to, close to, or otherwise being capable of being captured in a medical image via an image sensor. A portion of the test kit may be placed on or around the colorized surface prior to collection of a medical image. Alternatively, a colorized surface may be placed on or around a medical analysis region, such as a skin feature, prior to collection of a medical image.

In another aspect of the invention, the received medical image information may be processed to determine a state of each corresponding medical analysis region. The processing may include any data or information manipulation or analysis that allows for a determination to be made. The processing may take place locally, such as on mobile communications device, or remotely on one or more servers. It is noted that the processing can be performed by any processor having been configured or programmed to perform such an operation. Determining a state of each corresponding medical analysis region may include any determination, analysis, or characterization capable of being obtained from medical image information. For example, analyzing colors, hues, shades, or other visual characteristic of a plurality of reagent pads may allow for a determination of one or more concentrations, levels, or presence of different analytes, characteristics or components found within a biological fluid. In another aspect, determining a state of each corresponding medical analysis region may include defining a skin feature as benign, precancerous, cancerous, infected, scar, healing, or any determination that can be associated with a skin feature. Another aspect of the method may involve, based on the processed medical image information, electronically identifying a group of individuals with medical analysis regions in a differing state of criticality than others of the plurality of individuals. A group of individuals may include one or more individuals. In some examples, the group of individuals may be electronically identified based on results of any one of process 700, process 800, process 1400, process 1700, process 2000, process 2300, and so forth.

Electronically identifying may include any data or information processing, analyzing, or manipulation that can be performed electronically. This may include any digital or analog analysis performed with software, firmware, or hardware, and may also include any transmission or manipulation of a file, data, information, notification, message, or alert over any wired or wireless communication network. A differing state of criticality may be determined by any quantifiable or measurable characteristic or feature from the received medical image information. For example, a determination of the presence or absence of an analyte in a sample may lead to an identification of a differing state of criticality, the presence or absence of a skin feature may lead to an identification of a differing state of criticality, and the indication of compliance, no-compliance, or proper use of the home testing kit may lead to a differing state of criticality. In another aspect, the method may include electronically providing the healthcare provider with information indicating that there is a likelihood that the group of individuals is entitled to a second insurance status different from the first insurance status.

Electronically providing may include the transmission of any message, alert, file, data or information over any wired or wireless communication channel. A second insurance status may differ from the first insurance status in any manner. For example, differing insurance statuses may be based on a degree or level of health, risk, treatment cost, severity of a condition, one or more of the foregoing in combination with other patient specific information such as family medical history, age, preexisting condition, geographical or situational risk factors, or any other information related to the patient. By way of example only, the first insurance status may be associated with individuals who surpass a threshold, and a second insurance status may be associated with individuals who fall below threshold. If test results indicate an elevated risk of kidney failure, for example, such results may trigger a change in insurance status. Test results may cause either a reduction or an increase in insurance status. For example, an individual with a preexisting condition or risk may have an insurance status upgraded if test results suggest a marked improvement in condition or risk level. Alternatively, individuals who show a marked decrease in condition or risk may have their insurance status downgraded. Thus, for example, a first status may indicate a healthy individual, while a second status may be indicative of kidney failure or an increased likelihood of developing kidney failure, and may suggest the individuals entitled to the second insurance status may need more treatment, and thus incur additional healthcare expenses.

Figure 24:
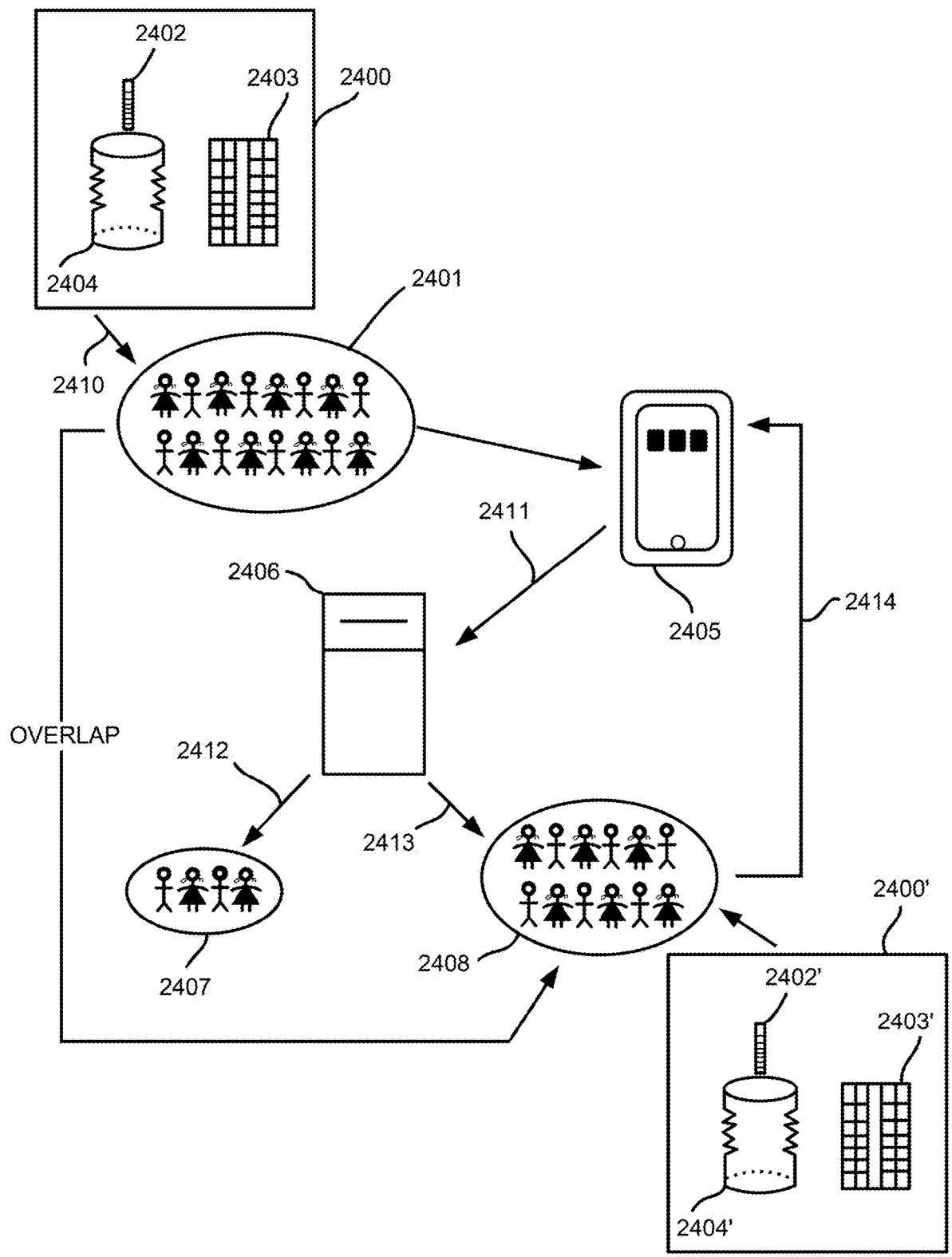
FIG. 24 is a schematic illustration of a method of automatically changing insurance status according to a first exemplary aspect of the disclosure.

While the features previously described are not limited to a particular structure or additional steps, by way of example only, FIG. 24 illustrates one example of a medical testing method that may aid healthcare providers to determine when conditions of a patient or a group of patients deteriorate. FIG. 24 illustrates a plurality of individuals 2401. The plurality of individuals 2401 may be a portion of the general population. The plurality of individuals 2401 may or may not have a pre-existing medical condition. In transmission 2410, the plurality of individuals each receive a home testing kit 2400, which may include a dip stick 2402, colorized surface 2403, and container 2404, among potentially other items. Container 2404 may have an adjustable size configured to contain a biological fluid. The dipstick 2402 may contain a plurality of reagent pads thereon for measuring differing properties of the biological fluid; and the colorized surface 2403 may contain a dipstick placement region and a plurality of colored reference elements greater in number than the plurality of reagent pads. The container 2404 may be adjustable in size from a smaller volume to a larger volume, or may be collapsible. This may be achieved through telescoping, bellows, or another feature. The biological fluid may be urine, sweat, stool, blood, breast milk, interstitial fluid, saliva or any other biological fluid or sample. The plurality of reagent pads may include any number greater than one, and may be configured to react with one or more characteristics, analytes, compounds, compositions, properties, features, etc. of the biological fluid. Moreover, one reagent pad may be configured to reflect a characteristic of a first biological fluid, and a second reagent pad may be configured to reflect a characteristic of a second biological fluid. The colorized surface 2403 may contain a plurality of colored reference elements greater in number than a plurality of reagent pads included on the dipstick 2402. Dipstick placement region may include a recess, a delineated section, a mark, or any feature that may direct a user as to where to place the dipstick.

The test kit may also include instructions for use (or a link to instructions for use). Regardless of the precise contents of the test kit and their intended use, the user might be instructed on how to perform a test, capture an image of an area of interest (e.g., at test strip) adjacent the colorized surface 2403, and to capture an associated image using mobile communications device 2405, such as a mobile phone. Some examples of mobile communications device 2405 may include any one of mobile communications device 115, mobile communications device 1604*a*, mobile communications device 1803, mobile communications device 2200, a smartphone, a tablet, a wearable computer, and so forth.

In the image, the colorized surface may be used to calibrate for local lighting conditions in order to determine rectified reference colors of the medical analysis region. For example, colorized surface 2403 may include a plurality of colored reference elements or other features which allow for calibration of local lighting conditions. This allows for analysis irrespective of local illumination conditions. For example, the method may allow for proper analysis in an overly bright room full of natural light, as well as a dim-lit room having fluorescent lighting. The home testing kits may further include a blot pad (not illustrated) for removing excess biological fluid from the dipstick after being dipped in the biological fluid, to thereby enable non-distorted image capture of the plurality of reagent pads by an image sensor. The blot pad may be formed of any suitable material for removing excess fluid such as cloth, paper, natural or synthetic fibers, porous material, or any other material having an absorbent, hydrophilic or wicking quality. An image sensor may include any sensor capable of detecting and converting optical signals in the near-infrared, infrared, visible, and ultraviolet spectrums into electrical signals.

Medical image information of at least some of the plurality of individuals 2401 may be transmitted via communication channel 2411 from mobile communications device 2405 to processing device 2406. Although a single test kit 2400, single mobile communications device 2405 and single communication channel 2411 are illustrated in FIG. 24, it is to be understood that each of the plurality of individuals 2401 will use a separate test kit and will likely capture the medical image on separate mobile communications devices for transmission to processing device 2406 via separate channels. Thus, the singular illustrations in FIG. 24 are for ease of discussion only and are intended to encompass the plural. Mobile communications devices 2405 may include one or more of a phone, mobile phone, smart phone, smart watch, tablet, laptop computer, personal computer, PDA, or any device which may allow for communication between a patient and the system. Mobile communications devices may include one or more image sensors or may receive information from one or more image sensors. The medical image information may include an image or other image-related data, metadata, or information. In one aspect, the medical image information may reflect a resulting color of a chemical reaction between a biological fluid and the at least one reagent test pad. The color may be any color, and the chemical reaction may take place with any desired analyte, characteristic, composition, component, feature, parameter, etc. of or in the biological fluid. When the biological fluid is urine, the medical image information may reflect an albumin to creatine ratio. The medical image information may reflect a reaction or change associated any analyte, characteristic, composition, component, feature, parameter, etc. of any biological fluid. In another aspect, the medical analysis region includes a skin feature, and the medical image information includes at least one of an image of the skin feature adjacent the colorized surface or data derived from the image of the skin feature adjacent the colorized surface. The skin feature may be one or more of a freckle, mole, cut, scrape, injury, mark, boil, legion, scar, etc. or any feature present on a surface of the skin, or underlying the surface of the skin. The medical image information may reflect information about the skin feature, such as a size, shape, color, healing progress, infection, benign, cancerous, pre-cancerous, etc. or any other information obtainable from data, metadata, or information related to an image.

The medical analysis region may include a portion of the dipstick 2402, including one or more of the reagent pads, a feature of a skin or body surface, or any other feature or element that may be used in conjunction with colorized surface 2403 to perform an analysis. The medical analysis region may include at least one reagent test pad, and the medical image information may include at least one of an image of the at least one reagent test pad adjacent the colorized surface or data derived from the image of the at least one reagent test pad adjacent the colorized surface. The at least one regent test pad may be one of a plurality of reagent test pads configured to react with one or more of an analyte, component, characteristic, property, feature, etc. within or associated with a biological fluid. Adjacent the colorized surface may include being positioned on, in, near, next to, or proximate a colorized surface.

A server or other processing device 2406 may process the received medical image information to determine a state of each corresponding medical analysis region. The server or other processing device 2406 may be a remote server or servers, a cloud-based server or servers, a local processing device such as a computer, CPU, microprocessor, or may be integrated into a mobile communications device 2405. Determining a state of each corresponding medical analysis region may include any determination, analysis, or characterization capable of being obtained from medical image information. For example, analyzing colors, hues, shades, etc. of a plurality of reagent pads may allow for a determination of one or more concentrations, levels, or presence of different analytes, characteristics or components found within a biological fluid. In another aspect, determining a state of each corresponding medical analysis region may include defining a skin feature as benign, precancerous, cancerous, infected, scar, etc. For example, the skin feature may be a mole and a determined state of the skin feature may be indicative of an increased likelihood that the mole is cancerous. Additionally, the skin feature may be a wound and a determined state of the skin feature is indicative of wound healing progress. Such a determinization may be made over a time utilizing a plurality of, or series of images. Moreover, such a determination may be made by comparison to one or more benchmarks or thresholds. The one or more benchmarks or thresholds may be based on research, medical literature, surveys, tests, etc. or based on a specific patient's prior medical image.

A method, system, or computer readable media of this disclosure may include, updating personal electronic medical records of the plurality of individuals with test results associated with the received medical information. In some examples, the received medical information may be based on process 700 and/or process 800 and/or process 1400 and/or process 1700 and/or process 2000 and/or process 2300. The plurality of individuals may include one or more of the plurality of individuals 2401. Test results may include concentrations, levels, characteristics, features, parameters, etc. of one or more components or analytes found within a biological fluid. Test results may also include raw data or other information associated with performing a home test. For example, original transmitted images may be included as test results as well as concentrations of specific compounds, or colors reflecting those concentrations.

Based on the processed medical image information, server or other processing device 2406 may electronically identify a group of individuals with medical analysis regions in a differing state of criticality than others of the plurality of individuals 2401. As illustrated in FIG. 24, a first group of individuals 2407 may be determined to have a medical analysis region in a differing state of criticality than a second group of individuals 2408. For example, a machine learning model may be trained using training examples to determine states of criticality of individuals from medical image information, and the trained machine learning model may be used to analyze the medical image information associated with an individual and determine the state of criticality of the individual. An example of such training examples may include medical image information together with a label indicative of a state of criticality.

A differing state of criticality may be determined by any quantifiable or measurable characteristic or feature from the received medical information. For example, medical image information indicating the presence of blood in urine samples of a portion of the population 2401 may be the basis for identifying a group of individuals with medical analysis regions in a differing state of criticality. Additionally, the presence or absence of a skin feature may lead to an identification of a differing state of criticality. Also, the differing state of criticality may indicate compliance, non-compliance, or proper use of the home testing kit.

A method, system, or computer readable media associated with this disclosure may include storing data associated with past medical image information of the plurality of individuals associated with a first insurance status, and identifying the state of criticality by comparing current medical image information with past medical image information. Data may be stored in one or more databases locally or remotely, on servers or a plurality of servers, on one or more cloud-based devices, ROM, RAM, or any storage device that may allow for querying or analysis of stored data. Medical image information may include one or more images, metadata associated with one or more images, calculations, results, or other information associated with or obtainable from one or more images, or any other information related with one or more medical images.

As illustrated in FIG. 24, the second group of individuals 2408 may be subject to additional testing at a later time (step 2414). These individuals 2408 may overlap with a subgroup of individual from group 2401. Periodically delivering home testing kits 2400' to some of the already tested individuals in group 2401 may enable those who were previously not entitled to an insurance status change (or who were originally subject to a change) to obtain a later revision of insurance status as the result of updated testing. This periodic retesting may be initiated by delivering home testing kits at a predetermined time period, such as annually or bi-annually.

Systems, methods, and computer readable media of this disclosure may include electronically providing the healthcare provider with information indicating that there is a likelihood that the group of individuals 2407 is entitled to a second insurance status different from the first insurance status. Providing the healthcare provider with the information that there is a likelihood that the group of individuals 2407 is entitled to a second insurance status different from the first insurance status may cause an automatic update of the insurance status of the group of individuals 2407. The group of individuals 2407 may include any number of individuals, from a few to a hundred or even many more individuals. The number of individuals in a group may be defined over a predetermined period of time. For example, the number of individuals in a group may increase up to a period of one year or more. In some examples, a machine learning model may be trained using training examples to determine whether individuals are entitled to a particular insurance status from states of criticality of individuals, and the trained machine learning model may be used to analyze a state of criticality of an individual to determine whether the individual is entitled to the particular insurance status (or a likelihood that the individual is entitled to the particular insurance status). An example of such training example may include a state of criticality of an individual together with a label indicating whether the individual is entitled to a particular insurance status (or a likelihood that the individual is entitled to the particular insurance status).

An automatic update of the insurance status may be performed over any wired or wireless communication pathway. An automatic update may alert one or more end users of a change in insurance status of the group of individuals. As illustrated in FIG. 24, a first group of individuals 2407 may be entitled to an insurance status different from an insurance status of the second group of individuals 2408, or different from an initial insurance status. Insurance status may include any status based on a diagnosis, an insurance claim, benefits limits, cost or price of coverage, provider information or any status related to health or healthcare. Coverage limits may differ between the first insurance status and the second insurance status. For example, if it is determined that the first group of individuals 2407 have received results indicating kidney failure or an increased likelihood of developing kidney failure, the second insurance status may suggest the first group of individuals 2407 may need more treatment, and thus incur additional healthcare expenses.

Figure 25:
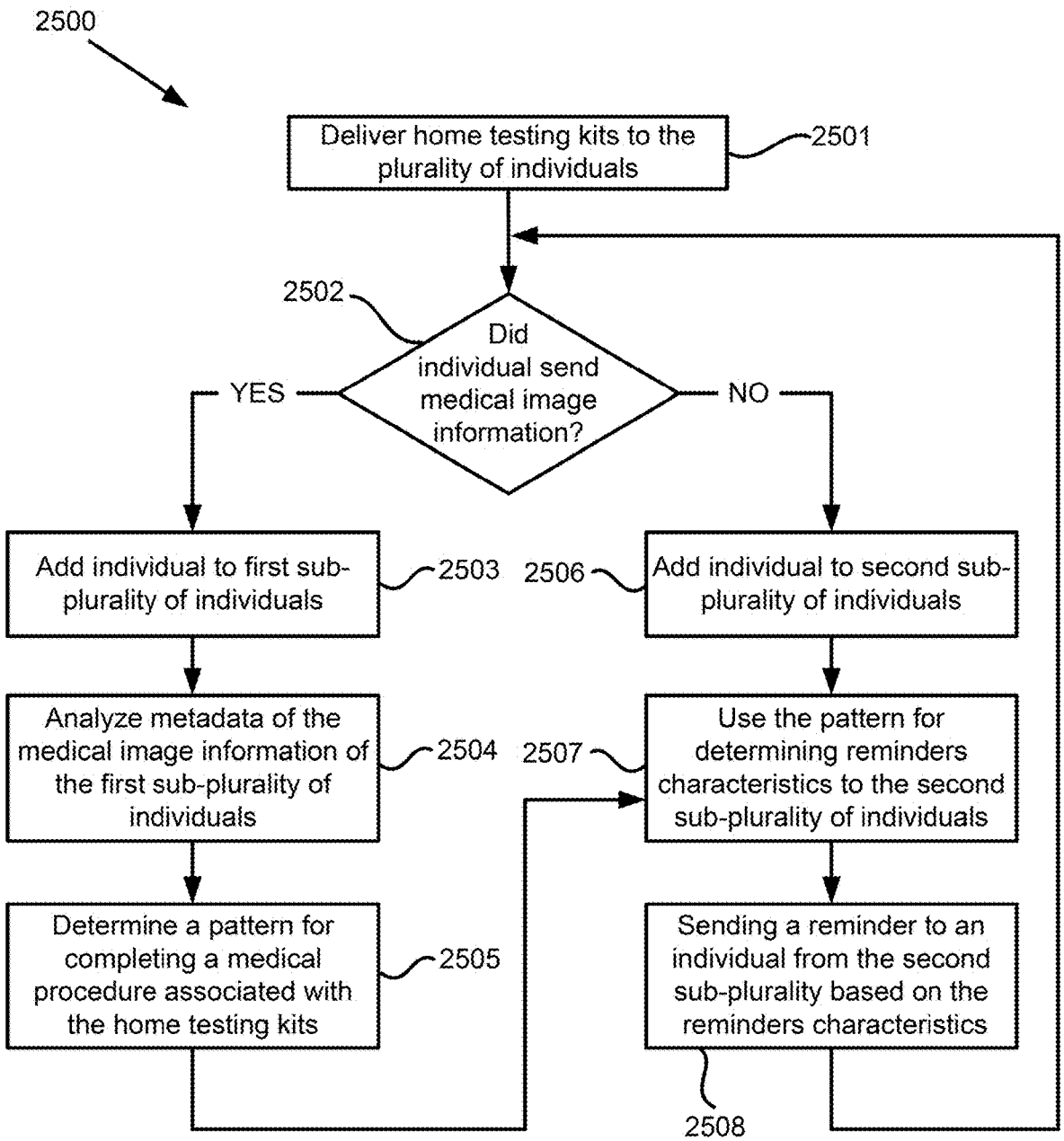
FIG. 25 is a logic flowchart illustrating one exemplary aspect of the disclosure for ensuring compliance among home test takers.

FIG. 25 illustrates an embodiment for increasing compliance among the plurality of individuals receiving a home testing kit. This embodiment may include identifying a first sub-plurality of individuals who transmitted medical image information within a time period; identifying a second sub-plurality of individuals who did not transmit medical image information within the time period; analyzing metadata of the medical image information associated with the first sub-plurality of individuals to determine at least one pattern for completing a medical procedure associated with the home testing kits; and sending a reminder to at least one member from the second sub-plurality of individuals based on the determined at least one pattern. As shown in step 2501, home testing kits may be delivered to a plurality of individuals. Step 2502 includes determining if an individual having received a home testing kit sends medical image information within a predetermined time period. A first sub-plurality of individuals who transmitted medical image information within a time period may be identified at step 2503. A second sub-plurality of individuals who did not transmit medical image information within the time period may be identified at step 2506. Analyzing metadata of the medical image information associated with the first sub-plurality of individuals may be performed at step 2504. The metadata of the medical image information may include times when the medical image information was transmitted, locations from which the medical information was transmitted, and information characterizing individuals such as individuals from the first sub-plurality of individuals. The metadata of the medical image information may additionally include time stamps, weather information, other geographical information, image sensor information, etc. or any other information capable of being obtained from, inferred, or associated with an image. Characterizing information may include age, gender, workplace, income, socio-economic status, race, weight, lifestyle information, etc.

The metadata may include any data or information that may be useful to determine at least one pattern for completing a medical procedure associated with the home testing kit as in step 2505. Patterns may be associated with a day of the week, time of day, time of the month, season, weather, where an individual lives, the age of an individual, work place, or any characteristic that may be analyzed to identify at least one pattern among individuals that complete a medical test. For example, a pattern may associate a subgroup of individuals with particular characteristic that increases and/or decrease the likelihood for completing the medical procedure. In one example, a RANdom SAmple Consensus (RANSAC) algorithm may be used to identify the subgroup of individuals and the particular characteristic. Upon determining a compliance pattern, the pattern may be used for determining reminder characteristics for use with the second sub-plurality of individuals at step 2507, for example by selecting reminder characteristics that increases the likelihood of individuals in the second sub-plurality of individuals to complete the medical procedure according to the determined at least one pattern and/or by avoiding reminder characteristics that decreases the likelihood of individuals in the second sub-plurality of individuals to complete the medical procedure according to the determined at least one pattern. A reminder may then be sent to at least one member from the second sub-plurality of individuals at step 2508 based on the determined at least one pattern and characteristics of the pattern (for example, based on the determined reminder characteristics). The at least one pattern may include one or more patterns. In one aspect, the determined at least one pattern may be an indication that adherent patients tended to comply on a particular weekday, and wherein sending the reminder based on the determined at least one pattern includes timing the reminder to coincide with the particular weekday. For example, in response to a determination that some individuals tend to comply on Fridays, a reminder may be sent to one or more of these individuals on a Friday. Additionally, if the pattern indicates that individuals tend to comply during the evening on Fridays, the reminder may be sent to coincide with a Friday evening. In another aspect, the determined at least one pattern may be an indication that adherent patients tended to comply when presented with a particular message, and wherein sending the reminder based on the determined at least one pattern includes sending the reminder with the particular message. The message may be one or more of a text or SMS message, an email, a letter, a song, a sound bite or clip, an animation, a prompt, a vibration or any other audio, visual, or tactile mode of communication.

Figure 26:
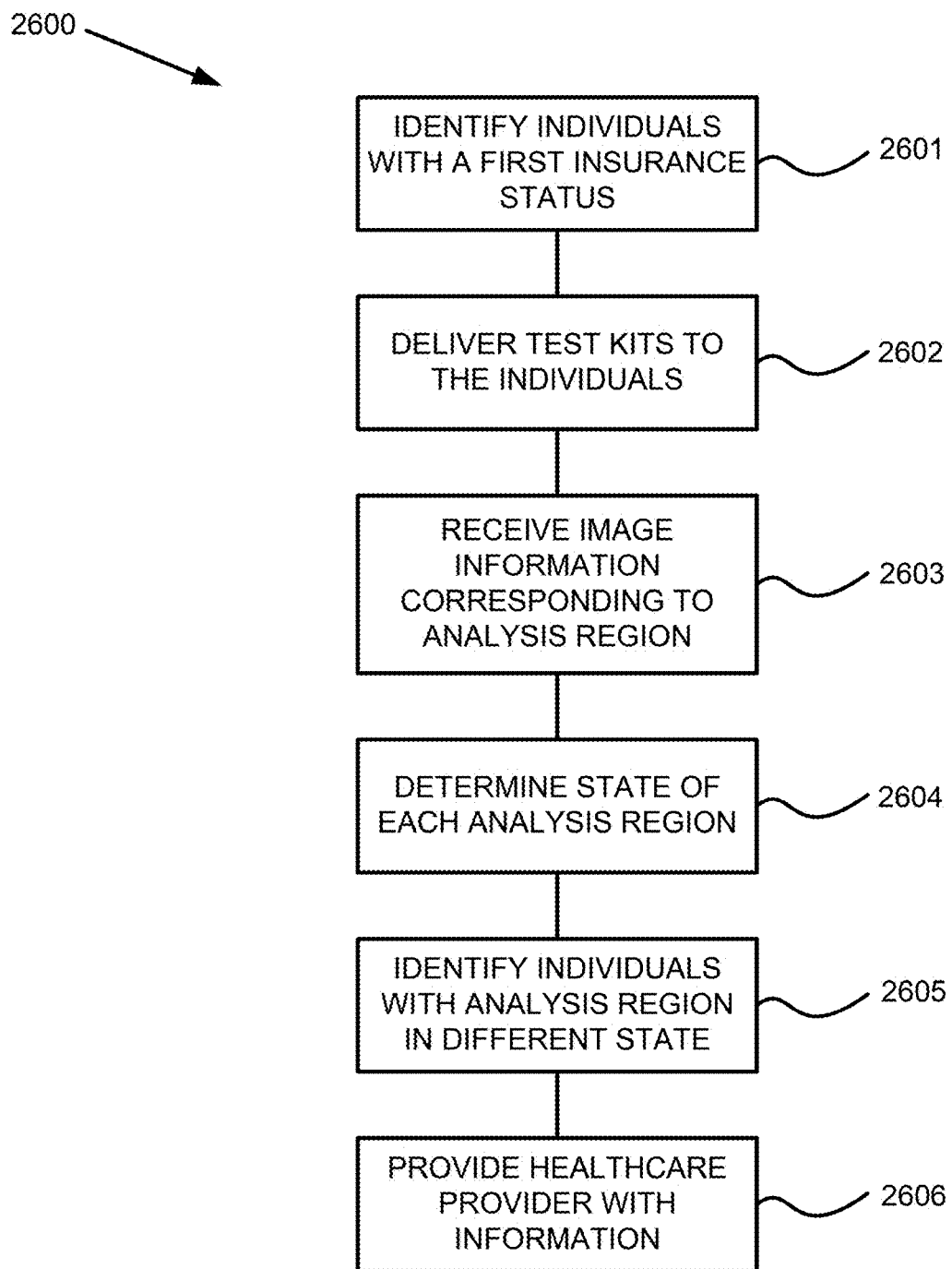
FIG. 26 is a flowchart illustrating another exemplary aspect of the disclosure.

FIG. 26 is a flow chart illustrating a medical testing method 2600 in accordance with the disclosure set forth above. A non-transitory computer readable medium may contain instructions that when executed by a processor cause the processor to perform the medical testing method 2600. The method may include receiving from a healthcare provider information identifying a plurality of individuals associated with a first insurance status. Step 2601 illustrates identifying individuals with a first insurance status. A healthcare provider may include any individual, organization or group of individuals or organizations, as discussed previously. A first insurance status may include any status based on a diagnosis, an insurance claim, benefits limits, cost or price of coverage, provider information or any status related to health or healthcare.

The method may include generating a list of a plurality of individuals to whom home testing kits are to be sent, wherein each home testing kit includes a colorized surface including a plurality of colored reference elements. A list of a plurality of individuals to whom home testing kits have been or are to be sent may be generated and test kits may be delivered to the individuals at step 2602. The plurality of individuals whom receive test kits may include one or more of the individuals having a first insurance status. A list may be generated or populated automatically, manually, or from querying a database, memory, or clearinghouse.

The method may include receiving electronically from mobile communications devices of at least some of the plurality of individuals, medical image information corresponding to a medical analysis region in proximity to the colorized surface. Step 2603 illustrates receiving image information corresponding to the analysis region. The medical image information may be sent or transmitted over any wired or wireless communication channel, over communication network 150, and so forth. The medical information may include an image, a portion of an image, metadata associated with an image or a portion of an image, or any other information or data associated with the medical image. The medical analysis region may include a dipstick, a portion of the dipstick including one or more test reagent pads, a skin feature, skin surface, etc.

The method may further include processing the received medical image information to determine a state of each corresponding medical analysis region. A state of each corresponding medical analysis region may be determined at step 2604. A state of each corresponding medical analysis region may include detecting or analyzing a color, characteristic, property, feature, etc. of an analysis region. The state of each corresponding medical analysis region may additionally include a diagnosis, or may indicate compliance with a medical test. For example, a state of a test reagent may include the diagnosis of a concentration of a specific analyte found in a biological fluid or other sample, or may merely indicate that a test has been performed, indicating patient compliance. For example, the processing of the received medical image information may include any of the analysis techniques described above.

The method may include based on the processed medical images, electronically identifying a group of individuals with medical analysis regions in a differing state of criticality than others of the plurality of individuals. At step 2605, individuals having analysis regions in different states may be identified. Electronically identifying may include any analysis, computation, comparison, etc. capable of being performed by a processor or being transmitted over any wired or wireless communication channel. A group of individuals may include one or more individuals. A differing state of criticality includes any detectable or measurable quality or feature of an analysis region.

The method may additionally include electronically providing the healthcare provider with information indicating that there is a likelihood that the group of individuals is entitled to a second insurance status different from the first insurance status. Electronically providing may include the transmission of a message, alert, file, data, information, etc. over any wired or wireless communication channel. A second insurance status may differ from the first insurance status in any manner. For example, the first insurance status may indicate a healthy individual, while the second status may be indicative of an unhealthy individual, such as, for example, someone at risk of or exhibiting symptoms of kidney failure, and may suggest the individuals entitled to the second insurance status may need more treatment, and thus incur additional healthcare expenses.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, e.g., hard disks or CD ROM, or other forms of RAM or ROM, USB media, DVD, Blu-ray, Ultra HD Blu-ray, or other optical drive media.

Computer programs based on the written description and disclosed methods are within the skills of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The examples are to be construed as non-exclusive. Furthermore, the steps of the disclosed methods may be modified in any manner, including by reordering steps and/or inserting or deleting steps. It is intended, therefore, that the specification and examples be considered as illustrative only.

The invention claimed is:

1. A color board for use in reagent strip testing, the color board comprising:
a color board surface;
a first colored reference element printed on the color board surface;
a second colored reference element printed on the color board surface;
a test region on the color board surface configured to receive at least one reagent pad; and
a unique code on the color board, the code being machine-readable and reflecting encoded information that, when read by a machine, indicates:
specific chromatic properties associated with each of the first colored reference element and the second colored reference element at a time of printing, wherein the encoded information is used by the machine to normalize a comparison color, for determining chromatic properties of the at least one reagent pad; and
at least one analysis to perform on the at least one reagent pad using the determined chromatic properties, thereby enabling sending results of the at least one analysis to an electronic device separate from the machine.

2. The color board of claim 1, wherein the chromatic properties are decipherable from the code.

3. The color board of claim 1, wherein the chromatic properties are determinable by comparing the code with information stored in a data structure.

4. The color board of claim 1, wherein the chromatic properties reflected by the code include at least one of hue, value, and chroma.

5. The color board of claim 1, wherein the chromatic properties reflected by the code include variations in colors of the first colored reference element and the second colored reference element.

6. The color board of claim 1, wherein normalizing a comparison color for determining the chromatic properties of the at least one reagent pad includes removing local illumination effects.

7. The color board of claim 1, wherein the code is configured to enable a machine to later determine at least one detail regarding a single home testing kit associated with the color board, and to execute testing of the at least one reagent pad based on the at least one detail.

8. The color board of claim 1, wherein the code is configured to enable a machine to later determine if the color board was used more than a predefined number of times.

9. The color board of claim 1, wherein the code is configured to enable a machine to later determine if the color board was previously used.

10. The color board of claim 1, wherein the first colored reference element and the second colored reference element share substantially a same color.

11. The color board of claim 10, wherein the first colored reference element and the second colored reference element are arranged on the color board on opposing sides of the test region.

12. The color board of claim 1, wherein the test region is configured to accommodate a reagent pad.

13. The color board of claim 1, wherein the test region is configured to accommodate a dipstick.

14. The color board of claim 1, wherein the test region is configured to accommodate a wound.

15. A non-transitory computer-readable medium containing instructions that when executed by at least one processor, cause the at least one processor to carry out a method for analyzing visible chemical reactions, the method comprising:

receiving, from an image sensor associated with a mobile communications device, an image of a reagent pad in proximity to a color board having: a color board surface, a first colored reference element, a second colored reference element, a test region on the color board surface configured to receive at least one reagent pad, and a machine-readable unique code;

determining from information encoded into the machine-readable unique code:
  specific chromatic properties associated with each of the first colored reference element and the second colored reference element to normalize a comparison color, for determining chromatic properties of the at least one reagent pad; and
  at least one analysis to perform on the at least one reagent pad using the determined chromatic properties, thereby enabling sending results of the at least one analysis to a first electronic device separate from the at least one processor; and using the specific chromatic properties of the first colored reference element and the second colored reference element to analyze a depiction of the at least one reagent pad in the image for determining an extent of a chemical reaction on the at least one reagent pad.

16. The non-transitory computer-readable medium of claim 15, wherein the method further includes:
  in response to first specific chromatic properties determined from the unique code and a first depiction of the at least one reagent pad in the image, determining a first extent of the chemical reaction on the at least one reagent pad; and
  in response to second specific chromatic properties determined from the unique code and the first depiction of the at least one reagent pad in the image, determining a second extent of the chemical reaction on the at least one reagent pad, the second extent differing from the first extent.

17. The non-transitory computer-readable medium of claim 15, wherein the method further includes:
  using the unique code to select a type of medical information to be provided; and
  based on the determined extent of the chemical reaction on the at least one reagent pad, providing medical information of the selected type of medical information.

18. The non-transitory computer-readable medium of claim 15, wherein the method further includes causing the mobile communications device to provide data representing the extent of the chemical reaction.

19. The non-transitory computer-readable medium of claim 15, wherein the method further includes:
  using the unique code to determine whether a number of usages of the color board exceeds a selected threshold;
  in response to a determination that the number of usages of the color board do not exceed the selected threshold, providing first information based on the determined extent of the chemical reaction on the at least one reagent pad; and
  in response to a determination that the number of usages of the color board exceeds the selected threshold, forgoing providing first information.

20. The non-transitory computer-readable medium of claim 15, wherein the method further includes:
  using the unique code to select a billing account; and
  causing an update to the selected billing account.

21. The color board of claim 1, wherein the code further includes additional encoded information indicative of at least one undesired test for the at least one reagent pad not to be provided to the machine that read the code.

22. The color board of claim 1, wherein the unique code is unique to a combination of at least two of: the color board, a geographical region, a production line, a creator of the color board, a health care provider, a type of desired medical test, an attribute of a user of the color board, a chromatic property, or a range of chromatic properties.

23. The color board of claim 1, wherein the encoded information indicates to the machine at least one of:
  the specific chromatic properties of the first and second colored reference elements stored in a database; or
  the first subset of analysis results to provide to the electronic device stored in a database.

24. The non-transitory computer-readable medium of claim 15, wherein the at least one analysis is based on a geographic region of a user of the mobile communications device or the reagent pad; and the method further comprises either:
  providing a first analysis to the first electronic device if the user is from a first geographic region; or
  providing a second analysis to a second electronic device if the user is from a second geographic region.

25. The non-transitory computer-readable medium of claim 15, wherein the at least one analysis is based on a service provider associated with a user of the mobile communications device or the reagent pad; and the method further comprises either:
  providing a first analysis to the first electronic device if the user is associated with a first service provider; or
  providing a second analysis to a second electronic device if the user is associated with a second service provider.

* * * * *